(12) United States Patent
Dengl et al.

(10) Patent No.: US 11,820,816 B2
(45) Date of Patent: *Nov. 21, 2023

(54) ANTI-VEGF ANTIBODIES AND METHODS OF USE

(71) Applicant: Hoffmann-La Roche Inc., Little Falls, NJ (US)

(72) Inventors: Stefan Dengl, Penzberg (DE); Sebastian Fenn, Penzberg (DE); Guy Georges, Penzberg (DE); Joerg Moelleken, Penzberg (DE); Francesca Ros, Penzberg (DE); Esther Koenigsberger, Penzberg (DE)

(73) Assignee: Hoffman-La Roche Inc., Little Falls, NJ (US)

( * ) Notice: Subject to any disclaimer, the term of this patent is extended or adjusted under 35 U.S.C. 154(b) by 194 days.

This patent is subject to a terminal disclaimer.

(21) Appl. No.: 16/912,950

(22) Filed: Jun. 26, 2020

(65) Prior Publication Data

US 2021/0079080 A1 Mar. 18, 2021

Related U.S. Application Data

(63) Continuation of application No. PCT/EP2018/086465, filed on Dec. 21, 2018.

(30) Foreign Application Priority Data

Dec. 29, 2017 (EP) ..................... 17211032

(51) Int. Cl.
*C07K 16/22* (2006.01)
*A61K 39/395* (2006.01)
*G16B 15/00* (2019.01)
*G16C 20/50* (2019.01)

(52) U.S. Cl.
CPC .......... *C07K 16/22* (2013.01); *A61K 39/3955* (2013.01); *G16B 15/00* (2019.02); *G16C 20/50* (2019.02); *C07K 2317/21* (2013.01); *C07K 2317/55* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS 4,816,567 A * 3/1989 Cabilly ................ C07K 16/462
530/867
2014/0079691 A1 3/2014 Mcconnell et al.

FOREIGN PATENT DOCUMENTS

| CA | 2992602 | 3/2017 |
|---|---|---|
| CA | 2802376 A | 12/2022 |
| CN | 103012589 | 7/2014 |
| CN | 101918030 | 10/2015 |
| CN | 102933602 | 8/2016 |
| CN | 104961828 | 3/2019 |
| EP | 3 006 465 A1 | 4/2013 |
| EP | 2 662 388 A1 | 11/2013 |
| EP | 2722055 | 4/2014 |
| WO | 00/64946 A3 | 11/2002 |
| WO | 2012/089176 A1 | 7/2005 |
| WO | 2005/000900 A1 | 1/2006 |
| WO | 2007/054816 A2 | 5/2007 |
| WO | 2008/133706 | 11/2008 |
| WO | 94/10202 A1 | 5/2011 |
| WO | 2009/060198 A1 | 5/2014 |
| WO | 2014/193191 | 12/2014 |
| WO | 98/45331 A2 | 10/2015 |
| WO | 98/45331 A3 | 10/2015 |
| WO | 98/45332 A2 | 10/2015 |
| WO | 2019/129677 | 7/2019 |
| WO | 2019/129679 | 7/2019 |
| WO | 00/35956 A1 | 6/2022 |

OTHER PUBLICATIONS

Doria-Rose and Gordon Joyce, Curr Opin Virol. Author manuscript; available in PMC Apr. 24, 2016; 19 pages total (Year: 2016).*
Aaron Nelson, mAbs 2:1, 77-83; Jan./Feb. 2010 (Year: 2010).*
Aldridge et al., "Vascular endothelial growth factor receptors in osteoclast differentiation and function" Biochemical and Biophysical Research Communications 335:793-798 (2005).
Asahara et al., "Isolation of Putative Progenitor Endothelial Cells for Angiogenesis" Science 275( SUPPL 5302):964-966 (1997).
Berkman et al., "Expression of the vascular permeability factor/vascular endothelial growth factor gene in central nervous system neoplasms" J. Clin. Invest 91:153-159 (Jan. 1993).
Borgstrom et al., "Complete Inhibition of Angiogenesis and Growth of Microtumors by Anti-Vascular Endothelial Growth Factor Neutralizing Antibody: Novel Concerts of Angiostatic Therapy from Intravital Videomicrocopy" Cancer Research 56:4032-4039 (1996).
Brekken et al., "Selective inhibition of vascular endothelial growth factor (VEGF) receptor 2 (KDR/Flk-1) activity by a monoclonal anti-VEGF antibody blocks tumor growth in mice" Cancer Res. 60:5117-5124 (2000).
Brown et al., "Expression of vascular permeability factor (vascular endothelial growth factor) and its receptors in breast cancer" Human Pathol. 26(1):86-91 (1995).
Brown et al., "Expression of vascular permeability factor (vascular endothelial growth factor) and its receptors in adenocarcinomas of the gastrointestinal tract" Cancer Res. 53:4727-4735 (Oct. 1, 1993).
Carmeliet et al., "Abnormal blood vessel development and lethality in embryos lacking a single VEGF allele" Nature 380:435-439 (Apr. 4, 1996).
Dvorak et al., "Vascular permeability factor/vascular endothelial growth factor, microvascular hyperpermeability, and angiogenesis" Am. J. Pathol. 146(5):1029-1039 (May 1995).
Ferrara and Davis-Smyth, "The Biology of Vascular Endothelial Growth Factor" Endocr. Rev. 18(1):4-25 (1997).
Ferrara et al., "Heterozygous embryonic lethality induced by targeted inactivation of the VEGF gene" Nature 380:439-442 (Apr. 4, 1996).

(Continued)

*Primary Examiner* — Christina M Borgeest

(57) ABSTRACT

The present invention relates to anti-VEGF antibodies and methods of their production and their use.

9 Claims, 14 Drawing Sheets

Specification includes a Sequence Listing.

(56) References Cited

OTHER PUBLICATIONS

Fidler et al., "Molecular determinants of angiogenesis in cancer metastasis" Cancer J. Sci. Am. [4(1):S58-66 ( 1998).
Folkman and Shing, "Angiogenesis" J. Biol. Chem. 267(16):10931-10934 (Jun. 5, 1992).
Garner et al., Pathobiology of Ocular Disease. A Dynamic Approach "Vascular Diseases" Garner, A., Klintworth GK Eds., 2nd edition, NY:Marcel Dekker,:1625-1710 ( 1994).
Holash et al., "VEGF-Trap: A Vegf blocker with potent antitumor effects" PNAS 99(17):11393-11398 (2002).
International Preliminary Report on Patentability for PCT/EP2018/086465 dated Jun. 30, 2020.
International Search Report for PCT/EP2018/086465 dated Apr. 8, 2019.
Jia et al., "Protein asparagine deamidation prediction based on structures with machine learning methods" PLOS One 12(7 SUPPL e0181347):1-17 (Jul. 21, 2017).
Kim et al., "Inhibition of Vascular Endothelial Growth Factor-Induced Angiogenesis Suppresses Tumour Growth in Vivo" Nature 362:841-844 ( 1993).
Klagsbrun, et al., "Regulators of Antiogenesis" Ann. Rev. Physiol. 53:217-239 (Dec. 30, 1991).
Leung et al., "Vascular Endothelial Growth Factor Is a Secreted Angiogenic Mitogen" Science 246:1306-1309 (Dec. 1989).
Mattern, J. et al., "Association of vascular endothelial growth factor expression with intratumoral microvessel density and tumour cell proliferation in human epidermoid lung carcinoma" Brit. J. Cancer 73:931-934 ( 1996).
McNamara et al., "Significance of angiogenesis in cancer therapy" British Journal of Surgery 85:1044-1055 (1998).
Melnyk et al., "Vascular Endothelial Growth Factor Promotes Tumor Dissemination by a Mechanism Distinct from its Effect on Primary Tumor Growth" Cancer Research 56:921-924 1996.
Siemeister et al. et al., "The pivotal role of VEGF in tumor angiogenesis: molecular facts and therapeutic opportunities" Cancer and Metastasis Reviews 17(2):241-248 ( 1998).
Springer et al., "VEGF Gene Delivery to Muscle: Potential Role for Vasculogenesis in Adults" Molecular Cell 2:549-558 ( 1998).
Sullivan et al., "r84, a Novel Therapeutic Antibody against Mouse and Human VEGF with Potent Anti-Tumor Activity and Limited Toxicity Induction" PLOS One 5(8):e12031 (2010).
Warren et al., "Regulation by Vascular Endothelial Growth Factor of Human Colon Cancer Tumorigenesis in a Mouse Model of Experimental Liver Metastasis" Journal of Clinical Investigation 95:1789-1797 (1995).
Yang et al., "Comparison of Binding Characteristics and In Vitro Activities of Three Inhibitors of Vascular Endothelial Growth Factor A" Mol. Pharm. 11(10):3421-3430 (Oct. 6, 2014).
Yang et al., "Potent anti-angiogenesis and anti-tumor activity of a novel human anti-VEGF antibody, MIL60" Cell Mol I 11(3):285-293 (May 1, 2014).
Yu et al., "A Humanized Anti-VEGF Rabbit Monoclonal Antibody Inhibits Angiogenesis and Blocks Tumor Growth in Xenograft Models" PLOS One5(2 SUPPL e9072):1-12 (Feb. 5, 2010).
F. Hoffman-La Roche, AG., "Anti VEGF Antibodies and Methods of Use" Unpublished Priority Application (European Patent Application No. 17211032.2 filed Dec. 29, 2017), (2017).
Fuh et al., "Structure-Function Studies of Two Synthetic Anti-vasvular Endothelial Growth Factor Fabs and Comparison with the Avastin Fab" The Journal of Biological Chemistry 281(10):6625-6631 (2006).
International Preliminary Report on Patentability, PCT/EP2019/086510 (dated Jun. 16, 2021; Chapter I),:pp. 1-19 (Jul. 1, 2021).
International Search Report, PCT/EP2019/086510 (w/Written Opinion),:pp. 1-27 (dated Apr. 15, 2020).
Lai et al., "Generation of Potent Anti-Vascular Endothelial Growth Facto Neutralizing Antibodies from Mouse Phage Display Library for Cancer Therapy" International Journal of Molecular Sciences 17(214):1-17 (2016).
International Preliminary Report on Patentability for PCT/EP2018/086468 dated Jun. 30, 2020.
International Search Report for PCT/EP2018/086468 dated Apr. 8, 2019.
Lee et al., "Differential Effects of VEGFR-1 and VEGFR-2 Inhibition on Tumor Metastases Based on Host Organ Environment" Cancer Reaserch:8357-8367 ( 2019) http://www.cacerres.aacrjournals.org.
Dong-Sheng et al., "Study on the Biological Activity of Monoclonal Antibody Against Extracellular Region III of Human VEGF Receptor II" Immunological Journal 21(5):366369 (Sep. 2005) Abstract only in English.
Jiang et al., "Construction, Expression and Activity Test of a Reshaping Single-Chain * Antibody Against Human CD3" Journal of Genetics and Genomics:762-771 ( 2000.
Shen, "Basic Research on Therapeutic Antibodies" Chinese Journal of Pharmacology and Toxicology 4:241-244 (2001) Abstract only in English.
Wang et al., "Biological Activity of Bifunctional VEGF Receptor Fusion Protein Mutants" Modern Immunology 30(5):11-14 (2010) Abstract only in English.

* cited by examiner

FIG. 13

| position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|---|---|---|---|---|---|---|---|---|---|---|---|---|---|---|---|---|---|---|
| SEQ ID NO: 45 | A | P | M | A | E | G | G | G | Q | N | H | H | E | V | V | K | F | M | D | V | Y | Q | R | S | Y | C | H | P | I | E | T | L | V | D | I |
| epitope 1st VEGF-A121 | | | | | | | | | | | | | | | | | ■ | ■ | ■ | | ■ | | | | ■ | | ■ | ■ | ■ | ■ | | | | | |
| epitope 2nd VEGF-A121 | | | | | | | | | | | | | | | | | | | | | | | | | | | | ■ | ■ | ■ | | | | | |

| position | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 |
|---|---|---|---|---|---|---|---|---|---|---|---|---|---|---|---|---|---|---|---|---|---|---|---|---|---|---|---|---|---|---|---|---|---|---|---|
| SEQ ID NO: 45 | F | Q | E | Y | P | D | E | I | E | Y | I | F | K | P | S | C | V | P | L | M | R | C | G | G | C | C | N | D | E | G | L | E | C | V | P |
| epitope 1st VEGF-A121 | | | | | | | | | | | | | ■ | | | | | | | ■ | | | | | | ■ | ■ | | | | ■ | | | | |
| epitope 2nd VEGF-A121 | | | | | | | | | | | | | | | | | | | | | | | | | | | | | | | | | | | |

| position | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 |
|---|---|---|---|---|---|---|---|---|---|---|---|---|---|---|---|---|---|---|---|---|---|---|---|---|---|---|---|---|---|---|---|---|---|---|---|
| SEQ ID NO: 45 | T | E | E | S | N | I | T | M | Q | I | M | R | I | K | P | H | Q | G | Q | H | I | G | E | M | S | F | L | Q | H | N | K | C | E | C | R |
| epitope 1st VEGF-A121 | | | | | | | | | | | ■ | | | | | | | | | | | | | | | | | | | | | ■ | ■ | ■ | ■ |
| epitope 2nd VEGF-A121 | | | | | | | | | | | | | | | | | ■ | | | | | | | | | | | | | | | | | | |

| position | 106 | 107 | 108 | 109 | 110 | 111 | 112 | 113 | 114 | 115 | 116 | 117 | 118 | 119 | 120 | 121 |
|---|---|---|---|---|---|---|---|---|---|---|---|---|---|---|---|---|
| SEQ ID NO: 45 | P | K | K | D | R | A | R | Q | E | K | C | D | K | P | R | R |
| epitope 1st VEGF-A121 | | ■ | | | | | | | | | | | | | | |
| epitope 2nd VEGF-A121 | | | | | | | | | | | | | | | | |

SEQUENCE LISTING

```
<160> NUMBER OF SEQ ID NOS: 47

<210> SEQ ID NO 1
<211> LENGTH: 117
<212> TYPE: PRT
<213> ORGANISM: Artificial Sequence
<220> FEATURE:
<223> OTHER INFORMATION: VH domain of antibody VEGF-0089

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Thr Trp Val Arg Gln Ala Pro Gly Lys Gly Leu Glu Trp Val
        35                  40                  45

Ser Ser Ile Gly Asn Gly Gly Gly Ile Tyr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Asp Asn Leu Phe Asp Ser Trp Gly Pro Gly Thr Leu
            100                 105                 110

Val Thr Val Ser Ser
        115

<210> SEQ ID NO 2
<211> LENGTH: 106
<212> TYPE: PRT
<213> ORGANISM: Artificial Sequence
<220> FEATURE:
<223> OTHER INFORMATION: VL domain of antibodies VEGF-0089, VEGF-0113,
      VEGF-0114, VEGF-P1AD8675

<400> SEQUENCE: 2

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Ser Ile Tyr Ser Ser
            20                  25                  30
```

```
Leu Asn Trp Tyr Gln Gln Lys Pro Gly Lys Ala Pro Lys Leu Leu Ile
            35                  40                  45

Tyr Ala Ser Thr Leu Gln Ser Gly Val Pro Ser Arg Phe Ser Gly Ser
    50                  55                  60

Ala Ser Gly Thr Asp Phe Thr Leu Thr Ile Ser Ser Leu Gln Pro Glu
65                  70                  75                  80

Asp Val Ala Thr Tyr Tyr Cys Gln Gln Tyr Gln Asn Phe Pro Arg Thr
                85                  90                  95

Phe Gly Gln Gly Thr Lys Leu Glu Ile Lys
            100                 105

<210> SEQ ID NO 3
<211> LENGTH: 5
<212> TYPE: PRT
<213> ORGANISM: Artificial Sequence
<220> FEATURE:
<223> OTHER INFORMATION: H-CDR1 of antibodies VEGF-0089, VEGF-0113,
      VEGF-0114, VEGF-P1AD8675

<400> SEQUENCE: 3

Asn Tyr Ala Met Thr
1               5

<210> SEQ ID NO 4
<211> LENGTH: 18
<212> TYPE: PRT
<213> ORGANISM: Artificial Sequence
<220> FEATURE:
<223> OTHER INFORMATION: H-CDR2 of antibodies VEGF-0089, VEGF-P1AD8675

<400> SEQUENCE: 4

Ser Ile Gly Asn Gly Gly Gly Ile Tyr Thr Tyr Tyr Ala Asp Ser Val
1               5                   10                  15

Lys Gly

<210> SEQ ID NO 5
<211> LENGTH: 7
<212> TYPE: PRT
<213> ORGANISM: Artificial Sequence
<220> FEATURE:
<223> OTHER INFORMATION: H-CDR3 of antibodies VEGF-0089, VEGF-0113,
      VEGF-0114, VEGF-P1AD8675

<400> SEQUENCE: 5

Gly Asp Asn Leu Phe Asp Ser
1               5

<210> SEQ ID NO 6
<211> LENGTH: 11
<212> TYPE: PRT
<213> ORGANISM: Artificial Sequence
<220> FEATURE:
<223> OTHER INFORMATION: L-CDR1 of antibodies VEGF-0089, VEGF-0113,
      VEGF-0114, VEGF-P1AD8675

<400> SEQUENCE: 6

Arg Ala Ser Gln Ser Ile Tyr Ser Ser Leu Asn
1               5                   10

<210> SEQ ID NO 7
<211> LENGTH: 11
<212> TYPE: PRT
<213> ORGANISM: Artificial Sequence
<220> FEATURE:
```

```
<223> OTHER INFORMATION: L-CDR2 of antibodies VEGF-0089, VEGF-0113,
      VEGF-0114, VEGF-P1AD8675

<400> SEQUENCE: 7

Ala Ser Thr Leu Gln Ser Gly Val Pro Ser Arg
1               5                   10

<210> SEQ ID NO 8
<211> LENGTH: 4
<212> TYPE: PRT
<213> ORGANISM: Artificial Sequence
<220> FEATURE:
<223> OTHER INFORMATION: L-CDR3 of antibodies VEGF-0089, VEGF-0113,
      VEGF-0114, VEGF-P1AD8675

<400> SEQUENCE: 8

Phe Pro Arg Thr
1

<210> SEQ ID NO 9
<211> LENGTH: 117
<212> TYPE: PRT
<213> ORGANISM: Artificial Sequence
<220> FEATURE:
<223> OTHER INFORMATION: VH domain of antibody VEGF-0113

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Thr Trp Val Arg Gln Ala Pro Gly Lys Gly Leu Glu Trp Val
        35                  40                  45

Ser Ser Ile Gly Asn Gly Pro Gly Ile Tyr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Asp Asn Leu Phe Asp Ser Trp Gly Pro Gly Thr Leu
            100                 105                 110

Val Thr Val Ser Ser
        115

<210> SEQ ID NO 10
<211> LENGTH: 18
<212> TYPE: PRT
<213> ORGANISM: Artificial Sequence
<220> FEATURE:
<223> OTHER INFORMATION: H-CDR2 of antibody VEGF-0113

<400> SEQUENCE: 10

Ser Ile Gly Asn Gly Pro Gly Ile Tyr Thr Tyr Tyr Ala Asp Ser Val
1               5                   10                  15

Lys Gly

<210> SEQ ID NO 11
<211> LENGTH: 116
<212> TYPE: PRT
<213> ORGANISM: Artificial Sequence
<220> FEATURE:
<223> OTHER INFORMATION: VH domain of antibody VEGF-0114
```

```
<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Thr Trp Val Arg Gln Ala Pro Gly Lys Gly Leu Glu Trp Val
        35                  40                  45

Ser Ser Ile Gly Ser Gly Gly Phe Tyr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Asn Leu Phe Asp Ser Trp Gly Pro Gly Thr Leu Val
            100                 105                 110

Thr Val Ser Ser
            115

<210> SEQ ID NO 12
<211> LENGTH: 17
<212> TYPE: PRT
<213> ORGANISM: Artificial Sequence
<220> FEATURE:
<223> OTHER INFORMATION: H-CDR2 of antibody VEGF-0114

<400> SEQUENCE: 12

Ser Ile Gly Ser Gly Gly Phe Tyr Thr Tyr Tyr Ala Asp Ser Val Lys
1               5                   10                  15

Gly

<210> SEQ ID NO 13
<211> LENGTH: 235
<212> TYPE: PRT
<213> ORGANISM: Artificial Sequence
<220> FEATURE:
<223> OTHER INFORMATION: heavy chain of VEGF-0089 Fab fragment

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Thr Trp Val Arg Gln Ala Pro Gly Lys Gly Leu Glu Trp Val
        35                  40                  45

Ser Ser Ile Gly Asn Gly Gly Gly Ile Tyr Thr Tyr Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Asp Asn Leu Phe Asp Ser Trp Gly Pro Gly Thr Leu
            100                 105                 110

Val Thr Val Ser Ser Gly Gln Pro Lys Ala Pro Ser Val Phe Pro Leu
            115                 120                 125

Ala Pro Cys Cys Gly Asp Thr Pro Ser Ser Thr Val Thr Leu Gly Cys
            130                 135                 140

Leu Val Lys Gly Tyr Leu Pro Glu Pro Val Thr Val Thr Trp Asn Ser
```

```
                145                 150                 155                 160
Gly Thr Leu Thr Asn Gly Val Arg Thr Phe Pro Ser Val Arg Gln Ser
                165                 170                 175

Ser Gly Leu Tyr Ser Leu Ser Ser Val Val Ser Val Thr Ser Ser Ser
                180                 185                 190

Gln Pro Val Thr Cys Asn Val Ala His Pro Ala Thr Asn Thr Lys Val
                195                 200                 205

Asp Lys Thr Val Ala Pro Ser Thr Cys Ser Glu Gln Lys Leu Ile Ser
        210                 215                 220

Glu Glu Asp Leu Gly Ala Ala Glu Pro Glu Ala
225                 230                 235

<210> SEQ ID NO 14
<211> LENGTH: 213
<212> TYPE: PRT
<213> ORGANISM: Artificial Sequence
<220> FEATURE:
<223> OTHER INFORMATION: light chain of VEGF-0089, VEGF-0113, VEGF-0114,
      VEGF-P1AD8675 Fab fragment

<400> SEQUENCE: 14

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Ser Ile Tyr Ser Ser
            20                  25                  30

Leu Asn Trp Tyr Gln Gln Lys Pro Gly Lys Ala Pro Lys Leu Leu Ile
        35                  40                  45

Tyr Ala Ser Thr Leu Gln Ser Gly Val Pro Ser Arg Phe Ser Gly Ser
    50                  55                  60

Ala Ser Gly Thr Asp Phe Thr Leu Thr Ile Ser Ser Leu Gln Pro Glu
65                  70                  75                  80

Asp Val Ala Thr Tyr Tyr Cys Gln Gln Tyr Gln Asn Phe Pro Arg Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 15
<211> LENGTH: 235
<212> TYPE: PRT
<213> ORGANISM: Artificial Sequence
<220> FEATURE:
<223> OTHER INFORMATION: heavy chain of VEGF-0113 Fab fragment

<400> SEQUENCE: 15
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Thr Trp Val Arg Gln Ala Pro Gly Lys Gly Leu Glu Trp Val
            35                  40                  45

Ser Ser Ile Gly Asn Gly Pro Gly Ile Tyr Thr Tyr Tyr Ala Asp Ser
50                      55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Asp Asn Leu Phe Asp Ser Trp Gly Pro Gly Thr Leu
            100                 105                 110

Val Thr Val Ser Ser Gly Gln Pro Lys Ala Pro Ser Val Phe Pro Leu
            115                 120                 125

Ala Pro Cys Cys Gly Asp Thr Pro Ser Ser Thr Val Thr Leu Gly Cys
130                 135                 140

Leu Val Lys Gly Tyr Leu Pro Glu Pro Val Thr Val Thr Trp Asn Ser
145                 150                 155                 160

Gly Thr Leu Thr Asn Gly Val Arg Thr Phe Pro Ser Val Arg Gln Ser
                165                 170                 175

Ser Gly Leu Tyr Ser Leu Ser Ser Val Val Ser Val Thr Ser Ser Ser
            180                 185                 190

Gln Pro Val Thr Cys Asn Val Ala His Pro Ala Thr Asn Thr Lys Val
            195                 200                 205

Asp Lys Thr Val Ala Pro Ser Thr Cys Ser Gln Lys Leu Ile Ser
210                 215                 220

Glu Glu Asp Leu Gly Ala Ala Glu Pro Glu Ala
225                 230                 235

<210> SEQ ID NO 16
<211> LENGTH: 234
<212> TYPE: PRT
<213> ORGANISM: Artificial Sequence
<220> FEATURE:
<223> OTHER INFORMATION: heavy chain of VEGF-0114 Fab fragment

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Thr Trp Val Arg Gln Ala Pro Gly Lys Gly Leu Glu Trp Val
            35                  40                  45

Ser Ser Ile Gly Ser Gly Gly Phe Tyr Thr Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Asn Leu Phe Asp Ser Trp Gly Pro Gly Thr Leu Val
            100                 105                 110

Thr Val Ser Ser Gly Gln Pro Lys Ala Pro Ser Val Phe Pro Leu Ala
            115                 120                 125

```
Pro Cys Cys Gly Asp Thr Pro Ser Ser Thr Val Thr Leu Gly Cys Leu
        130                 135                 140

Val Lys Gly Tyr Leu Pro Glu Pro Val Thr Val Thr Trp Asn Ser Gly
145                 150                 155                 160

Thr Leu Thr Asn Gly Val Arg Thr Phe Pro Ser Val Arg Gln Ser Ser
                165                 170                 175

Gly Leu Tyr Ser Leu Ser Ser Val Val Ser Val Thr Ser Ser Ser Gln
            180                 185                 190

Pro Val Thr Cys Asn Val Ala His Pro Ala Thr Asn Thr Lys Val Asp
        195                 200                 205

Lys Thr Val Ala Pro Ser Thr Cys Ser Glu Gln Lys Leu Ile Ser Glu
210                 215                 220

Glu Asp Leu Gly Ala Ala Glu Pro Glu Ala
225                 230
```

<210> SEQ ID NO 17
<211> LENGTH: 233
<212> TYPE: PRT
<213> ORGANISM: Artificial Sequence
<220> FEATURE:
<223> OTHER INFORMATION: heavy chain of 2C3 Fab fragment

<400> SEQUENCE: 17

```
Lys Leu Gln Val Gln Leu Gln Glu Ser Gly Pro Glu Leu Val Lys Pro
1               5                   10                  15

Gly Ala Ser Val Lys Met Ser Cys Lys Ala Ser Gly Tyr Thr Phe Thr
            20                  25                  30

Ser Tyr Val Phe His Trp Val Lys Gln Lys Pro Gly Gln Gly Leu Glu
        35                  40                  45

Trp Ile Gly Tyr Ile Asn Pro Tyr Asn Asp Val Thr Lys Tyr Asn Glu
    50                  55                  60

Lys Phe Lys Gly Lys Ala Thr Leu Thr Ser Asp Lys Ser Ser Ser Thr
65                  70                  75                  80

Ala Tyr Met Glu Leu Ser Ser Leu Thr Ser Glu Asp Ser Ala Val Tyr
                85                  90                  95

Tyr Cys Ala Ser Tyr Tyr Gly Ser Ser Tyr Gly Tyr Tyr Ala Met Asp
            100                 105                 110

Asp Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Ala Thr
225                 230
```

<210> SEQ ID NO 18

```
<211> LENGTH: 220
<212> TYPE: PRT
<213> ORGANISM: Artificial Sequence
<220> FEATURE:
<223> OTHER INFORMATION: light chain of 2C3 Fab fragment

<400> SEQUENCE: 18

Asp Ile Gln Leu Thr Gln Ser Pro Ala Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile His Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 19
<211> LENGTH: 234
<212> TYPE: PRT
<213> ORGANISM: Artificial Sequence
<220> FEATURE:
<223> OTHER INFORMATION: heavy chain of r84 Fab fragment

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Arg Ser Met Val Arg Gly Val Ile Ile Pro Phe Asn Gly
```

```
            100                 105                 110
Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr
225                 230

<210> SEQ ID NO 20
<211> LENGTH: 214
<212> TYPE: PRT
<213> ORGANISM: Artificial Sequence
<220> FEATURE:
<223> OTHER INFORMATION: light chain of r84 Fab fragment

<400> SEQUENCE: 20

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 21
<211> LENGTH: 227
<212> TYPE: PRT
<213> ORGANISM: Artificial Sequence
<220> FEATURE:
<223> OTHER INFORMATION: heavy chain of L3H6 Fab fragment

<400> SEQUENCE: 21
```

Gln Gln Val Gln Leu Val Gln Ser Gly Ala Glu Val Lys Lys Pro Gly
1               5                   10                  15

Glu Ser Leu Lys Ile Ser Cys Lys Gly Ser Gly Tyr Ser Phe Thr Ser
            20                  25                  30

Tyr Trp Ile Gly Trp Val Arg Gln Met Pro Gly Lys Gly Leu Glu Trp
        35                  40                  45

Met Gly Ile Ile Tyr Pro Gly Asp Ser Asp Thr Arg Tyr Ser Pro Ser
    50                  55                  60

Phe Gln Gly Gln Val Thr Ile Ser Ala Asp Lys Ser Ile Ser Thr Ala
65                  70                  75                  80

Tyr Leu Gln Trp Ser Ser Leu Lys Ala Ser Asp Thr Ala Met Tyr Tyr
                85                  90                  95

Cys Ala Arg Gln Gly Thr His Asn Arg Lys Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Gly Ser Glu
    210                 215                 220

Pro Glu Ala
225

```
<210> SEQ ID NO 22
<211> LENGTH: 216
<212> TYPE: PRT
<213> ORGANISM: Artificial Sequence
<220> FEATURE:
<223> OTHER INFORMATION: light chain of L3H6 Fab fragment

<400> SEQUENCE: 22
```

Gln Ala Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Asn Tyr Pro Asn Trp Phe Gln Gln Arg Pro Gly Gln Pro Pro Arg Ala
        35                  40                  45

Leu Ile Tyr Ser Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

```
Gln Pro Glu Asp Glu Ala Glu Tyr Tyr Cys Arg Leu Ser Tyr Asp Leu
                85                  90                  95

Ala Arg Pro Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 23
<211> LENGTH: 214
<212> TYPE: PRT
<213> ORGANISM: Artificial Sequence
<220> FEATURE:
<223> OTHER INFORMATION: heavy chain of Lucentis (ranibizumab)

<400> SEQUENCE: 23

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

-continued

<210> SEQ ID NO 24
<211> LENGTH: 226
<212> TYPE: PRT
<213> ORGANISM: Artificial Sequence
<220> FEATURE:
<223> OTHER INFORMATION: light chain of Lucentis (ranibizumab)

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys
225

<210> SEQ ID NO 25
<211> LENGTH: 454
<212> TYPE: PRT
<213> ORGANISM: Artificial Sequence
<220> FEATURE:
<223> OTHER INFORMATION: heavy chain of 2C3 full length IgG1 antibody

<400> SEQUENCE: 25

Lys Leu Gln Val Gln Leu Gln Glu Ser Gly Pro Glu Leu Val Lys Pro
1               5                   10                  15

Gly Ala Ser Val Lys Met Ser Cys Lys Ala Ser Gly Tyr Thr Phe Thr
            20                  25                  30

Ser Tyr Val Phe His Trp Val Lys Gln Lys Pro Gly Gln Gly Leu Glu
        35                  40                  45

Trp Ile Gly Tyr Ile Asn Pro Tyr Asn Asp Val Thr Lys Tyr Asn Glu
    50                  55                  60

Lys Phe Lys Gly Lys Ala Thr Leu Thr Ser Asp Lys Ser Ser Ser Thr
65                  70                  75                  80

Ala Tyr Met Glu Leu Ser Ser Leu Thr Ser Glu Asp Ser Ala Val Tyr
                85                  90                  95

Tyr Cys Ala Ser Tyr Tyr Gly Ser Ser Tyr Gly Tyr Tyr Ala Met Asp
            100                 105                 110

Asp Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 26
<211> LENGTH: 220
<212> TYPE: PRT
<213> ORGANISM: Artificial Sequence
<220> FEATURE:

<223> OTHER INFORMATION: light chain of 2C3 full length IgG1 antibody

<400> SEQUENCE: 26

Asp Ile Gln Leu Thr Gln Ser Pro Ala Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile His Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 27
<211> LENGTH: 456
<212> TYPE: PRT
<213> ORGANISM: Artificial Sequence
<220> FEATURE:
<223> OTHER INFORMATION: heavy chain of r84 full length IgG1 antibody

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Arg Ser Met Val Arg Gly Val Ile Ile Pro Phe Asn Gly
            100                 105                 110

Met Asp Val Trp Gly Gln Gly Thr Thr Val Thr Val Ser Ser Ala Ser
        115                 120                 125

```
Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro Gly Lys
    450                 455

<210> SEQ ID NO 28
<211> LENGTH: 214
<212> TYPE: PRT
<213> ORGANISM: Artificial Sequence
<220> FEATURE:
<223> OTHER INFORMATION: light chain of r84 full length IgG1 antibody

<400> SEQUENCE: 28

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 29
<211> LENGTH: 232
<212> TYPE: PRT
<213> ORGANISM: Homo sapiens

<400> SEQUENCE: 29

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
                35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys

```
                180             185             190
His Leu Phe Val Gln Asp Pro Gln Thr Cys Lys Cys Ser Cys Lys Asn
            195             200             205

Thr Asp Ser Arg Cys Lys Ala Arg Gln Leu Glu Leu Asn Glu Arg Thr
        210             215             220

Cys Arg Cys Asp Lys Pro Arg Arg
225             230

<210> SEQ ID NO 30
<211> LENGTH: 18
<212> TYPE: PRT
<213> ORGANISM: Artificial Sequence
<220> FEATURE:
<223> OTHER INFORMATION: anti-VEGF antibody H-CDR2 consensus sequence I
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa is either no amino acid or selected from
      any naturally occuring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 30

Ser Ile Gly Xaa Gly Xaa Xaa Xaa Tyr Thr Tyr Tyr Ala Asp Ser Val
1               5                   10                  15

Lys Gly

<210> SEQ ID NO 31
<211> LENGTH: 18
<212> TYPE: PRT
<213> ORGANISM: Artificial Sequence
<220> FEATURE:
<223> OTHER INFORMATION: anti-VEGF antibody H-CDR2 consensus sequence II
<220> FEATURE:
<221> NAME/KEY: MISC_FEATURE
<222> LOCATION: (4)..(4)
<223> OTHER INFORMATION: Xaa is N or S
<220> FEATURE:
<221> NAME/KEY: MISC_FEATURE
<222> LOCATION: (6)..(6)
<223> OTHER INFORMATION: Xaa is G or P
<220> FEATURE:
<221> NAME/KEY: MISC_FEATURE
<222> LOCATION: (7)..(7)
<223> OTHER INFORMATION: Xaa is either a gap or G
<220> FEATURE:
<221> NAME/KEY: MISC_FEATURE
<222> LOCATION: (8)..(8)
<223> OTHER INFORMATION: Xaa is I or F

<400> SEQUENCE: 31

Ser Ile Gly Xaa Gly Xaa Xaa Xaa Tyr Thr Tyr Tyr Ala Asp Ser Val
1               5                   10                  15

Lys Gly

<210> SEQ ID NO 32
<211> LENGTH: 220
<212> TYPE: PRT
<213> ORGANISM: Artificial Sequence
```

<220> FEATURE:
<223> OTHER INFORMATION: heavy chain of VEGF-P1AD8675 Fab fragment

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Thr Trp Val Arg Gln Ala Pro Gly Lys Gly Leu Glu Trp Val
        35                  40                  45

Ser Ser Ile Gly Asn Gly Gly Ile Tyr Thr Tyr Tyr Ala Asp Ser
50                  55                  60

Val Lys Gly Arg Phe Thr Ile Ser Arg Asp Asn Trp Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Asp Asn Leu Phe Asp Ser Trp Gly Pro Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220

<210> SEQ ID NO 33
<211> LENGTH: 117
<212> TYPE: PRT
<213> ORGANISM: Artificial Sequence
<220> FEATURE:
<223> OTHER INFORMATION: VH domain of antibody VEGF-P1AD8675

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Thr Trp Val Arg Gln Ala Pro Gly Lys Gly Leu Glu Trp Val
        35                  40                  45

Ser Ser Ile Gly Asn Gly Gly Ile Tyr Thr Tyr Tyr Ala Asp Ser
50                  55                  60

Val Lys Gly Arg Phe Thr Ile Ser Arg Asp Asn Trp Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Asp Asn Leu Phe Asp Ser Trp Gly Pro Gly Thr Leu
            100                 105                 110

Val Thr Val Ser Ser

-continued

115

<210> SEQ ID NO 34
<211> LENGTH: 240
<212> TYPE: PRT
<213> ORGANISM: Artificial Sequence
<220> FEATURE:
<223> OTHER INFORMATION: heavy chain of HF2-1 Fab fragment

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Asn Phe Val Phe Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Thr Gly Tyr Gly Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser Gly Gln Pro Lys Ala Pro
        115                 120                 125

Ser Val Phe Pro Leu Ala Pro Cys Cys Gly Asp Thr Pro Ser Ser Thr
    130                 135                 140

Val Thr Leu Gly Cys Leu Val Lys Gly Tyr Leu Pro Glu Pro Val Thr
145                 150                 155                 160

Val Thr Trp Asn Ser Gly Thr Leu Thr Asn Gly Val Arg Thr Phe Pro
                165                 170                 175

Ser Val Arg Gln Ser Ser Gly Leu Tyr Ser Leu Ser Ser Val Val Ser
            180                 185                 190

Val Thr Ser Ser Ser Gln Pro Val Thr Cys Asn Val Ala His Pro Ala
        195                 200                 205

Thr Asn Thr Lys Val Asp Lys Thr Val Ala Pro Ser Thr Cys Ser Glu
    210                 215                 220

Gln Lys Leu Ile Ser Glu Glu Asp Leu Gly Ala Ala Glu Pro Glu Ala
225                 230                 235                 240

<210> SEQ ID NO 35
<211> LENGTH: 216
<212> TYPE: PRT
<213> ORGANISM: Artificial Sequence
<220> FEATURE:
<223> OTHER INFORMATION: light chain of HF2-1 and HF2-5 Fab fragment

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Ser Gly Gly Ser Asp Ser Ala Tyr Gly
            20                  25                  30

Tyr Gly Trp Tyr Gln Gln Lys Pro Gly Lys Ala Pro Lys Thr Leu Ile
        35                  40                  45

Tyr Trp Asp Asp Lys Arg Pro Ser Gly Val Pro Ser Arg Phe Ser Gly
    50                  55                  60

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gly Ala Trp Glu Tyr Ser Gly Gly
                 85                  90                  95

Val Gly Ile Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
            210                 215

<210> SEQ ID NO 36
<211> LENGTH: 240
<212> TYPE: PRT
<213> ORGANISM: Artificial Sequence
<220> FEATURE:
<223> OTHER INFORMATION: heavy chain of HF2-5 Fab fragment

<400> SEQUENCE: 36

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Met Ile Arg Ser His
             20                  25                  30

Gly Met Gln Trp Val Arg Gln Ala Pro Gly Lys Gly Leu Glu Tyr Val
             35                  40                  45

Ala Gly Ile Ser Ser Asp Gly Ser Trp Ala Arg His Ser Ala Ala Val
         50                  55                  60

Glu Gly Arg Phe Thr Ile Ser Arg Asp Asp Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser Gly Gln Pro Lys Ala Pro
            115                 120                 125

Ser Val Phe Pro Leu Ala Pro Cys Cys Gly Asp Thr Pro Ser Ser Thr
            130                 135                 140

Val Thr Leu Gly Cys Leu Val Lys Gly Tyr Leu Pro Glu Pro Val Thr
145                 150                 155                 160

Val Thr Trp Asn Ser Gly Thr Leu Thr Asn Gly Val Arg Thr Phe Pro
                165                 170                 175

Ser Val Arg Gln Ser Ser Gly Leu Tyr Ser Leu Ser Ser Val Val Ser
            180                 185                 190

Val Thr Ser Ser Ser Gln Pro Val Thr Cys Asn Val Ala His Pro Ala
            195                 200                 205
```

```
Thr Asn Thr Lys Val Asp Lys Thr Val Ala Pro Ser Thr Cys Ser Glu
    210                 215                 220

Gln Lys Leu Ile Ser Glu Glu Asp Leu Gly Ala Ala Glu Pro Glu Ala
225                 230                 235                 240
```

<210> SEQ ID NO 37
<211> LENGTH: 240
<212> TYPE: PRT
<213> ORGANISM: Artificial Sequence
<220> FEATURE:
<223> OTHER INFORMATION: heavy chain of HF2-9 Fab fragment

<400> SEQUENCE: 37

```
Glu Val Gln Leu Val Glu Ser Gly Gly Gly Leu Val Gln Pro Gly Gly
1               5                   10                  15

Ser Leu Arg Leu Ser Cys Ala Ala Ser Met Phe Arg Ile Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Phe Arg Val Ala Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser Gly Gln Pro Lys Ala Pro
        115                 120                 125

Ser Val Phe Pro Leu Ala Pro Cys Cys Gly Asp Thr Pro Ser Ser Thr
    130                 135                 140

Val Thr Leu Gly Cys Leu Val Lys Gly Tyr Leu Pro Glu Pro Val Thr
145                 150                 155                 160

Val Thr Trp Asn Ser Gly Thr Leu Thr Asn Gly Val Arg Thr Phe Pro
                165                 170                 175

Ser Val Arg Gln Ser Ser Gly Leu Tyr Ser Leu Ser Ser Val Val Ser
            180                 185                 190

Val Thr Ser Ser Ser Gln Pro Val Thr Cys Asn Val Ala His Pro Ala
        195                 200                 205

Thr Asn Thr Lys Val Asp Lys Thr Val Ala Pro Ser Thr Cys Ser Glu
    210                 215                 220

Gln Lys Leu Ile Ser Glu Glu Asp Leu Gly Ala Ala Glu Pro Glu Ala
225                 230                 235                 240
```

<210> SEQ ID NO 38
<211> LENGTH: 216
<212> TYPE: PRT
<213> ORGANISM: Artificial Sequence
<220> FEATURE:
<223> OTHER INFORMATION: light chain of HF2-9 Fab fragment

<400> SEQUENCE: 38

```
Asp Ile Gln Met Thr Gln Ser Pro Ser Ser Leu Ser Ala Ser Val Gly
1               5                   10                  15

Asp Arg Val Thr Ile Thr Cys Ser Gly Gly Ser Met Glu Pro Leu Gly
            20                  25                  30

Tyr Gly Trp Tyr Gln Gln Lys Pro Gly Lys Ala Pro Lys Thr Leu Ile
        35                  40                  45
```

Tyr Trp Asp Asp Lys Arg Pro Ser Gly Val Pro Ser Arg Phe Ser Gly
          50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gly Ala Trp Glu Tyr Ser Gly Gly
                  85                  90                  95

Val Gly Ile Phe Gly Gln Gly Thr Lys Val Glu Ile Lys Arg Thr Val
                 100                 105                 110

Ala Ala Pro Ser Val Phe Ile Phe Pro Pro Ser Asp Glu Gln Leu Lys
             115                 120                 125

Ser Gly Thr Ala Ser Val Val Cys Leu Leu Asn Asn Phe Tyr Pro Arg
         130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                 165                 170                 175

Leu Ser Ser Thr Leu Thr Leu Ser Lys Ala Asp Tyr Glu Lys His Lys
             180                 185                 190

Val Tyr Ala Cys Glu Val Thr His Gln Gly Leu Ser Ser Pro Val Thr
         195                 200                 205

Lys Ser Phe Asn Arg Gly Glu Cys
     210                 215

<210> SEQ ID NO 39
<211> LENGTH: 240
<212> TYPE: PRT
<213> ORGANISM: Artificial Sequence
<220> FEATURE:
<223> OTHER INFORMATION: heavy chain of HF2-11 Fab fragment

<400> SEQUENCE: 39

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Leu Ile Arg Ser His
             20                  25                  30

Gly Met Gln Trp Val Arg Gln Ala Pro Gly Lys Gly Leu Glu Tyr Val
         35                  40                  45

Ala Gly Ile Ser Ser Asp Gly Ser Trp Val Lys Val Ala Ala Ala Val
     50                  55                  60

Glu Gly Arg Phe Thr Ile Ser Arg Asp Asp Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asp Phe Ser Thr Gly Tyr Gly Ala Asp Ser Ile Asp Ala Trp
                 100                 105                 110

Gly Gln Gly Thr Leu Val Thr Val Ser Ser Gly Gln Pro Lys Ala Pro
             115                 120                 125

Ser Val Phe Pro Leu Ala Pro Cys Cys Gly Asp Thr Pro Ser Ser Thr
         130                 135                 140

Val Thr Leu Gly Cys Leu Val Lys Gly Tyr Leu Pro Glu Pro Val Thr
145                 150                 155                 160

Val Thr Trp Asn Ser Gly Thr Leu Thr Asn Gly Val Arg Thr Phe Pro
                 165                 170                 175

Ser Val Arg Gln Ser Ser Gly Leu Tyr Ser Leu Ser Ser Val Val Ser
             180                 185                 190

Val Thr Ser Ser Ser Gln Pro Val Thr Cys Asn Val Ala His Pro Ala
            195                 200                 205

Thr Asn Thr Lys Val Asp Lys Thr Val Ala Pro Ser Thr Cys Ser Glu
            210                 215                 220

Gln Lys Leu Ile Ser Glu Glu Asp Leu Gly Ala Ala Glu Pro Glu Ala
225                 230                 235                 240

<210> SEQ ID NO 40
<211> LENGTH: 216
<212> TYPE: PRT
<213> ORGANISM: Artificial Sequence
<220> FEATURE:
<223> OTHER INFORMATION: light chain of HF2-11 Fab fragment

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Ser Gly Gly Ser Ser Glu Pro Leu Gly
            20                  25                  30

Tyr Gly Trp Tyr Gln Gln Lys Pro Gly Lys Ala Pro Lys Thr Leu Ile
        35                  40                  45

Tyr Trp Asp Asp Lys Arg Pro Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gly Ala Trp Glu Tyr Ser Gly Gly
                85                  90                  95

Val Gly Ile Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 41
<211> LENGTH: 235
<212> TYPE: PRT
<213> ORGANISM: Artificial Sequence
<220> FEATURE:
<223> OTHER INFORMATION: heavy chain of VEGF-P1AE3520 Fab fragment

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Thr Trp Val Arg Gln Ala Pro Gly Lys Gly Leu Glu Trp Val

```
                    35                  40                  45
Ser Ser Ile Gly Asn Gly Pro Gly Ile Tyr Thr Tyr Tyr Ala Asp Ser
 50                      55                  60

Val Lys Gly Arg Phe Thr Ile Ser Arg Asp Asn Trp Lys Asn Thr Leu
 65                  70                  75                  80

Tyr Leu Gln Met Asn Ser Leu Arg Ala Glu Asp Thr Ala Val Tyr Tyr
                     85                  90                  95

Cys Ala Lys Gly Asp Asn Leu Phe Asp Ser Trp Gly Pro Gly Thr Leu
                    100                 105                 110

Val Thr Val Ser Ser Gly Gln Pro Lys Ala Pro Ser Val Phe Pro Leu
            115                 120                 125

Ala Pro Cys Cys Gly Asp Thr Pro Ser Ser Thr Val Thr Leu Gly Cys
130                 135                 140

Leu Val Lys Gly Tyr Leu Pro Glu Pro Val Thr Val Thr Trp Asn Ser
145                 150                 155                 160

Gly Thr Leu Thr Asn Gly Val Arg Thr Phe Pro Ser Val Arg Gln Ser
                    165                 170                 175

Ser Gly Leu Tyr Ser Leu Ser Ser Val Val Ser Val Thr Ser Ser Ser
                180                 185                 190

Gln Pro Val Thr Cys Asn Val Ala His Pro Ala Thr Asn Thr Lys Val
            195                 200                 205

Asp Lys Thr Val Ala Pro Ser Thr Cys Ser Gln Lys Leu Ile Glu Ser
210                 215                 220

Glu Glu Asp Leu Gly Ala Ala Glu Pro Glu Ala
225                 230                 235

<210> SEQ ID NO 42
<211> LENGTH: 117
<212> TYPE: PRT
<213> ORGANISM: Artificial Sequence
<220> FEATURE:
<223> OTHER INFORMATION: VH domain of antibody VEGF-P1AE3520

<400> SEQUENCE: 42

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Tyr
                 20                  25                  30

Ala Met Thr Trp Val Arg Gln Ala Pro Gly Lys Gly Leu Glu Trp Val
             35                  40                  45

Ser Ser Ile Gly Asn Gly Pro Gly Ile Tyr Thr Tyr Tyr Ala Asp Ser
 50                      55                  60

Val Lys Gly Arg Phe Thr Ile Ser Arg Asp Asn Trp Lys Asn Thr Leu
 65                  70                  75                  80

Tyr Leu Gln Met Asn Ser Leu Arg Ala Glu Asp Thr Ala Val Tyr Tyr
                     85                  90                  95

Cys Ala Lys Gly Asp Asn Leu Phe Asp Ser Trp Gly Pro Gly Thr Leu
                    100                 105                 110

Val Thr Val Ser Ser
            115

<210> SEQ ID NO 43
<211> LENGTH: 234
<212> TYPE: PRT
<213> ORGANISM: Artificial Sequence
<220> FEATURE:
<223> OTHER INFORMATION: heavy chain of VEGF-P1AE3521 Fab fragment
```

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Thr Trp Val Arg Gln Ala Pro Gly Lys Gly Leu Glu Trp Val
        35                  40                  45

Ser Ser Ile Gly Ser Gly Gly Phe Tyr Thr Tyr Tyr Ala Asp Ser Val
    50                  55                  60

Lys Gly Arg Phe Thr Ile Ser Arg Asp Asn Trp Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Asn Leu Phe Asp Ser Trp Gly Pro Gly Thr Leu Val
            100                 105                 110

Thr Val Ser Ser Gly Gln Pro Lys Ala Pro Ser Val Phe Pro Leu Ala
        115                 120                 125

Pro Cys Cys Gly Asp Thr Pro Ser Ser Thr Val Thr Leu Gly Cys Leu
    130                 135                 140

Val Lys Gly Tyr Leu Pro Glu Pro Val Thr Val Thr Trp Asn Ser Gly
145                 150                 155                 160

Thr Leu Thr Asn Gly Val Arg Thr Phe Pro Ser Val Arg Gln Ser Ser
                165                 170                 175

Gly Leu Tyr Ser Leu Ser Ser Val Val Ser Val Thr Ser Ser Ser Gln
            180                 185                 190

Pro Val Thr Cys Asn Val Ala His Pro Ala Thr Asn Thr Lys Val Asp
        195                 200                 205

Lys Thr Val Ala Pro Ser Thr Cys Ser Glu Gln Lys Leu Ile Ser Glu
    210                 215                 220

Glu Asp Leu Gly Ala Ala Glu Pro Glu Ala
225                 230

<210> SEQ ID NO 44
<211> LENGTH: 116
<212> TYPE: PRT
<213> ORGANISM: Artificial Sequence
<220> FEATURE:
<223> OTHER INFORMATION: VH domain of antibody VEGF-P1AE3521

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Thr Trp Val Arg Gln Ala Pro Gly Lys Gly Leu Glu Trp Val
        35                  40                  45

Ser Ser Ile Gly Ser Gly Gly Phe Tyr Thr Tyr Tyr Ala Asp Ser Val
    50                  55                  60

Lys Gly Arg Phe Thr Ile Ser Arg Asp Asn Trp Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Asn Leu Phe Asp Ser Trp Gly Pro Gly Thr Leu Val
            100                 105                 110

```
Thr Val Ser Ser
        115

<210> SEQ ID NO 45
<211> LENGTH: 121
<212> TYPE: PRT
<213> ORGANISM: Homo sapiens

<400> SEQUENCE: 45

Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Cys Asp Lys Pro Arg Arg
            115                 120

<210> SEQ ID NO 46
<211> LENGTH: 31
<212> TYPE: PRT
<213> ORGANISM: Artificial Sequence
<220> FEATURE:
<223> OTHER INFORMATION: H-FR3 of VEGF-0089, VEGF-0113, VEGF-0114

<400> SEQUENCE: 46

Phe Thr Ile Ser Arg Asp Asn Ser Lys Asn Thr Leu Tyr Leu Gln Met
1               5                   10                  15

Asn Ser Leu Arg Ala Glu Asp Thr Ala Val Tyr Tyr Cys Ala Lys
            20                  25                  30

<210> SEQ ID NO 47
<211> LENGTH: 31
<212> TYPE: PRT
<213> ORGANISM: Artificial Sequence
<220> FEATURE:
<223> OTHER INFORMATION: H-FR3 of VEGF-P1AD8675

<400> SEQUENCE: 47

Phe Thr Ile Ser Arg Asp Asn Trp Lys Asn Thr Leu Tyr Leu Gln Met
1               5                   10                  15

Asn Ser Leu Arg Ala Glu Asp Thr Ala Val Tyr Tyr Cys Ala Lys
            20                  25                  30
```

ANTI-VEGF ANTIBODIES AND METHODS OF USE

CROSS REFERENCE TO RELATED APPLICATIONS

This application is a continuation of International Application No. PCT/EP2018/086465, filed Dec. 21, 2018, the disclosure of which is incorporated herein by reference in its entirety, and which claims priority to European Patent Application No. 17211032.2 filed Dec. 29, 2017.

SEQUENCE LISTING

The instant application contains a Sequence Listing which has been submitted electronically in ASCII format and is hereby incorporated by reference in its entirety. Said ASCII copy, created on Jun. 17, 2020, is named P34598_US_SequenceListing.txt and is 71.2 kilobytes in size.

FIELD OF THE INVENTION

The present invention relates to antibodies that inhibit angiogenesis, more particularly anti-VEGF antibodies, and methods of using the same.

BACKGROUND OF THE INVENTION

The present invention provides anti-VEGF antibodies that preferentially inhibit VEGF-binding to VEGF-R2 rather than VEGF-binding to VEGF-R1. While inhibiting angiogenesis, such antibodies have an improved safety due to their specific blocking properties.

Angiogenesis is the development of new vasculature from preexisting blood vessels and/or circulating endothelial stem cells (Asahara, M. et al., Science, 275(5302):964-967, 1997; Springer, et al., Mol. Cell, 2(5):549-558, 1998; Folkman and Shing, J. Biol. Chem., 267:10931-10934, 1992). While playing a vital role in many physiological processes, angiogenesis is also implicated in the pathogenesis of a variety of disorders, including solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al., Annu. Rev. Physiol. 53 (1991) 217-239; and Garner, A., Vascular diseases, in: Pathobiology of ocular disease, A dynamic approach, Garner, A., and Klintworth, G. K. (eds.), 2nd edition, Marcel Dekker, New York (1994), pp. 1625-1710).

Angiogenesis is regulated in normal and malignant tissues by the balance of angiogenic stimuli and angiogenic inhibitors that are produced in the target tissue and at distant sites (Fidler, et al., Cancer J. Sci. Am., 4 Suppl 1:S58-66, 1998; McNamara, et al., Br. J Surg., 85(8):1044-1055. 1998). Vascular endothelial growth factor-A (VEGF, also known as vascular permeability factor, VPF) is a primary stimulant of angiogenesis. Human VEGF (SEQ ID No: 29) is e.g. described in Leung, D. W., et al., Science 246 (1989). VEGF is involved in the regulation of normal and abnormal angiogenesis and neovascularization associated with tumors and intraocular disorders (Ferrara, N., et al., Endocr. Rev. 18 (1997) 4-25; Berkman, R. A., et al., J. Clin. Invest. 91 (1993) 153-159; Brown, L. F., et al., Human Pathol. 26 (1995) 86-91; Brown, L. F., et al., Cancer Res. 53 (1993) 4727-4735; Mattern, J., et al., Brit. J. Cancer. 73 (1996) 931-934; and Dvorak, H. F., et al., Am. J. Pathol. 146 (1995) 1029-1039). VEGF is a homodimeric glycoprotein that has been isolated from several sources. VEGF shows highly specific mitogenic activity for endothelial cells. VEGF has important regulatory functions in the formation of new blood vessels during embryonic vasculogenesis and in angiogenesis during adult life (Carmeliet, P., et al., Nature, 380 (1996) 435-439; Ferrara, N., et al., Nature, 380 (1996) 439-442; reviewed in Ferrara, N., et al., Endocr. Rev. 18 (1997) 4-25).

The identification of VEGF as a key stimulus of angiogenesis in the pathogenesis of a plurality of disorders resulted in various attempts to block VEGF activity, e.g. by anti-VEGF receptor antibodies, soluble receptor constructs, antisense strategies, RNA aptamers against VEGF and low molecular weight VEGF receptor tyrosine kinase (RTK) inhibitors (Siemeister, et al. Cancer Metastasis Rev., 17(2): 241-248., 1998). Anti-VEGF antibodies were described to suppress the growth of a variety of human tumor cell lines in mice (Kim, K. J., et al., Nature 362 (1993) 841-844; Warren, S. R., et al., J. Clin. Invest. 95 (1995) 1789-1797; Borgstrom, P., et al., Cancer Res. 56 (1996) 4032-4039; and Melnyk, O., et al., Cancer Res. 56 (1996) 921-924). WO 94/10202, WO 98/45332, WO 2005/00900 and WO 00/35956 refer to antibodies against VEGF. Humanized monoclonal antibody bevacizumab (sold under the trade name Avastin®) is an anti-VEGF antibody used in tumor therapy WO 98/45331. Ranibizumab (trade name Lucentis®) is a monoclonal antibody fragment derived from the same parent murine antibody as bevacizumab (Avastin®). It is much smaller than the parent molecule and has been affinity matured to provide stronger binding to VEGF-A (WO 98/45331). It is an anti-angiogenic compound that has been approved to treat the "wet" type of age-related macular degeneration (wAMD), a common form of age-related vision loss.

Anti-VEGF antibodies that are approved for clinical application, such as Avastin® and Lucentis®, inhibit VEGF-binding to both receptors, VEGF-R1 (FLT-1, fms-like tyrosine kinase) and VEGF-R2 (KDR/FLK-1, fetal liver kinase). VEGF-R1 and VEGF-R2 are closely related receptor tyrosine kinases (RTK). While VEGF-R2 is hypothized to be primarily responsible for VEGF-mediated angiogenesis (Holash, J. et al., Proc Natl Acad Sci USA. 2002 Aug. 20; 99(17):11393-8), VEGF-R1 is known to have other important biological roles unrelated to angiogenesis, e.g. in osteoclast differentiation (Aldridge, S. E. et al., Biochem Biophys Res Commun. 2005 Sep. 30; 335(3):793-8).

A few anti-VEGF antibodies that preferentially inhibit VEGF binding to VEGF-R2 but do not significantly inhibit VEGF-binding to VEGF-R1 have been reported (WO 200064946 describing an antibody termed "2C3", WO 2009060198 describing an antibody termed "r84", WO 2012089176 describing an antibody termed "L3H6", and EP3006465 describing antibodies termed "HF2-1", "HF2-5", "HF2-9", and "HF2-11"). By blocking VEGF binding to VEGF-R2, but not VEGF-R1, the antibodies are described to have an improved safety profile and do not show common toxicity-related side effects associated with anti-VEGF therapy (Brekken, R. A., et al., Cancer Res. 2000 Sep. 15; 60(18):5117-24; Sullivan, L. A., et al., PLoS One, 2010 Aug. 6; 5 (8):e12031).

As the development of antibodies providing this advantageous behaviour, and at the same time exhibit the required properties and sufficient affinity to make them suitable for clinical application is not a straightforward approach there is still a need for improved VEGF inhibitors.

SUMMARY OF THE INVENTION

The invention provides anti-VEGF antibodies and methods of using the same.

One aspect of the invention is an antibody that binds to VEGF, wherein binding of the antibody to VEGF significantly inhibits VEGF binding to VEGF receptor VEGF-R2 without significantly inhibiting VEGF binding to VEGF receptor VEGF-R1.

Another aspect of the invention is an antibody that binds to VEGF, wherein binding of the antibody to VEGF selectively inhibits binding of VEGF to VEGF-R2.

Another aspect of the invention is an antibody that binds to VEGF, wherein binding of the antibody to VEGF fully inhibits the binding of VEGF to VEGF-R2, and wherein binding of the antibody to VEGF does not fully inhibit the binding of VEGF to VEGF-R1.

Another aspect of the invention is an antibody that binds to VEGF, wherein the antibody binds VEGF with an affinity of ≤150 μM as measured by surface plasmon resonance at a temperature of 25° C., and wherein the antibody binds VEGF with a higher or with about the same affinity as measured by surface plasmon resonance at a temperature of 37° C.

Another aspect of the invention is an antibody that binds to VEGF that binds to the same epitope as an antibody comprising a VH sequence of SEQ ID NO: 01 and a VL sequence of SEQ ID NO: 02.

Another aspect of the invention is an antibody that binds to VEGF, wherein the antibody comprises a heavy chain variable domain (VH) comprising
  (a) CDR-H1 comprising the amino acid sequence of SEQ ID NO:03,
  (b) CDR-H2 comprising the amino acid sequence selected from the group of SEQ ID NO:04, SEQ ID NO:10, and SEQ ID NO: 12, and
  (c) CDR-H3 comprising the amino acid sequence of SEQ ID NO:05, and
wherein the antibody comprises a light chain variable domain (VL) comprising
  (d) CDR-L1 comprising the amino acid sequence of SEQ ID NO:06,
  (e) CDR-L2 comprising the amino acid sequence of SEQ ID NO:07, and
  (f) CDR-L3 comprising the amino acid sequence of SEQ ID NO:08.

In one embodiment the antibody comprises a VH sequence of SEQ ID NO: 01 and a VL sequence of SEQ ID NO: 02. In one embodiment the antibody comprises a VH sequence of SEQ ID NO: 09 and a VL sequence of SEQ ID NO: 02. In one embodiment the antibody comprises a VH sequence of SEQ ID NO: 11 and a VL sequence of SEQ ID NO: 02. In one embodiment the antibody comprises a VH sequence of SEQ ID NO: 33 and a VL sequence of SEQ ID NO: 02. In one embodiment the antibody comprises a VH sequence of SEQ ID NO: 42 and a VL sequence of SEQ ID NO: 02. In one embodiment the antibody comprises a VH sequence of SEQ ID NO: 44 and a VL sequence of SEQ ID NO: 02.

Another aspect of the invention is an antibody that specifically binds to VEGF comprising a VH sequence of SEQ ID NO: 01 and a VL sequence of SEQ ID NO: 02. Another aspect of the invention is an antibody that is an affinity matured variant of an antibody having a VH sequence of SEQ ID NO: 01 and a VL sequence of SEQ ID NO: 02. Another aspect of the invention is an antibody that binds to VEGF that binds to the same epitope as an antibody having a VH sequence of SEQ ID NO: 01 and a VL sequence of SEQ ID NO: 02.

Another aspect of the invention is an antibody that specifically binds to VEGF comprising a VH sequence of SEQ ID NO: 09 and a VL sequence of SEQ ID NO: 02.

Another aspect of the invention is an antibody that specifically binds to VEGF comprising a VH sequence of SEQ ID NO: 11 and a VL sequence of SEQ ID NO: 02.

Another aspect of the invention is an antibody that specifically binds to VEGF comprising a VH sequence of SEQ ID NO: 33 and a VL sequence of SEQ ID NO: 02.

Another aspect of the invention is an antibody that specifically binds to VEGF comprising a VH sequence of SEQ ID NO: 42 and a VL sequence of SEQ ID NO: 02.

Another aspect of the invention is an antibody that specifically binds to VEGF comprising a VH sequence of SEQ ID NO: 44 and a VL sequence of SEQ ID NO: 02.

Another aspect of the invention is an isolated nucleic acid encoding an antibody of the invention.

Another aspect of the invention is a host cell comprising a nucleic acid of the invention.

Another aspect of the invention is a method of producing an antibody that binds to VEGF comprising culturing the host cell of the invention under conditions suitable for the expression of the antibody. Another aspect of the invention is an antibody produced by said method.

Another aspect of the invention is a pharmaceutical composition comprising an antibody of the invention and a pharmaceutically acceptable carrier.

Another aspect of the invention is an antibody of invention or a pharmaceutical composition of the invention for use as a medicament.

Another aspect of the invention an the antibody of invention or a pharmaceutical composition of the invention for use in treating a VEGF-related disease, e.g. cancer or an eye disease.

Another aspect of the invention is the use of an antibody of the invention or a pharmaceutical composition of the invention in the manufacture of a medicament.

Another aspect of the invention is the use of an antibody of the invention or a pharmaceutical composition of the invention in the manufacture of a medicament for inhibiting angiogenesis.

Another aspect of the invention is a method of treating an individual having a VEGF-related disease, e.g. cancer or an eye disease, comprising administering to the individual an effective amount of an antibody of the invention or a pharmaceutical composition of the invention.

Another aspect of the invention is the a method of inhibiting angiogenesis in an individual comprising administering to the individual an effective amount of an antibody of the invention or a pharmaceutical composition of the invention to inhibit angiogenesis.

The invention provides novel anti-VEGF antibodies exhibiting particularly valuable properties, like a high affinity, high stability and an improved safety profile, e.g. by avoiding side effects caused by blocking VEGF-signalling through VEGF-R1. The antibodies provided by the invention exhibit a high affinity that allows therapeutic application of antibody fragments. The antibodies of the invention exhibit valuable properties causing a benefit for a patient suffering from VEGF-related diseases, such as cancer, vascular diseases or eye diseases (e.g. age related macular degeneration).

DESCRIPTION OF THE FIGURES

FIG. 13: Epitope amino acids bound by VEGF-0089 Fab fragment in a dimer of VEGF-A121 (SEQ ID NO: 45) as determined by X ray crystallography according to Example 13. Amino acid positions comprised in each one of the VEGF-A121 molecules in contact with VEGF-0089 Fab fragment within a distance of 5 Å are highlighted in black.

DETAILED DESCRIPTION OF THE INVENTION

1. Definitions

Figure 1:
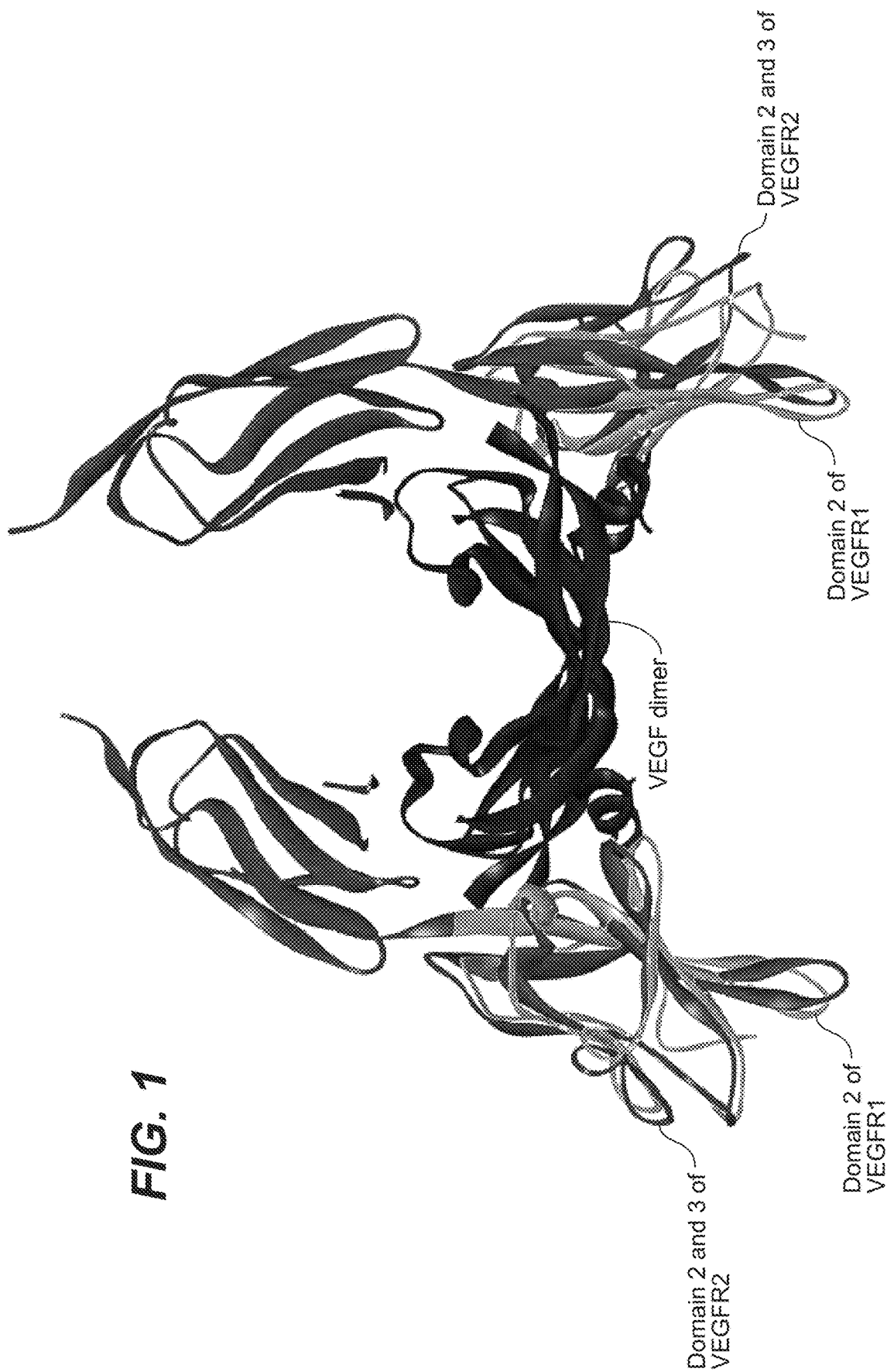
FIG. 1: Crystal structure of VEGF dimer in complex with VEGF-R1 domain 2 and with VEGF-R2 domain 2 and 3.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable domain (VH), also called a variable heavy domain or a heavy chain variable region, followed by three constant heavy domains (CH1, CH2, and CH3). Similarly, from N- to C-terminus, each light chain has a variable domain (VL), also called a variable light domain or a light chain variable region, followed by a constant light (CL) domain.

The terms "full length antibody", "intact antibody", and "whole antibody" are used herein interchangeably to refer to an antibody having a structure substantially similar to a native antibody structure or having heavy chains that contain an Fc region as defined herein.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For a review of methods for assessment of antibody purity, see, e.g., Flatman et al., J. Chromatogr. B 848:79-87 (2007).

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR (e.g. CDR) residues and other residues in the variable domain (e.g., FR residues) are numbered herein according to Kabat et al., supra.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, IgA₁, and IgA₂. In certain embodiments, the antibody is of the IgG₁ isotype. In certain embodiments, the antibody is of the IgG₁ isotype with the P329G, L234A and L235A mutation to reduce Fc-region effector function. In other embodiments, the antibody is of the IgG₂ isotype. In certain embodiments, the antibody is of the IgG₄ isotype with the S228P mutation in the hinge region to improve stability of IgG₄ antibody. The heavy chain constant domains that correspond to the different classes of immunoglobulins are called α, δ, ε, γ, and μ, respectively. The light chain of an antibody may be assigned to one of two types, called kappa (κ) and lambda (λ), based on the amino acid sequence of its constant domain.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "VEGF", as used herein, refers to any native VEGF from any vertebrate source, including mammals such as primates (e.g. humans) and rodents (e.g., mice and rats), unless otherwise indicated. The term encompasses "full-length", unprocessed VEGF as well as any form of VEGF that results from processing in the cell. The term also encompasses naturally occurring variants of VEGF, e.g., splice variants or allelic variants. The amino acid sequence of an exemplary human VEGF is shown in SEQ ID NO:29.

The terms "anti-VEGF antibody" and "an antibody that binds to VEGF" refer to an antibody that is capable of binding VEGF with sufficient affinity such that the antibody is useful as a diagnostic and/or therapeutic agent in targeting VEGF. In one embodiment, the extent of binding of an anti-VEGF antibody to an unrelated, non-VEGF protein is less than about 10% of the binding of the antibody to VEGF as measured, e.g., by surface plasmon resonance (SPR). In certain embodiments, an antibody that binds to VEGF has a dissociation constant (Kd) of ≤1 μM, ≤100 nM, ≤10 nM, ≤1 nM, ≤0.1 nM, ≤0.01 nM, or ≤0.001 nM (e.g. 10-8 M or less, e.g. from 10-8 M to 10-13 M, e.g., from 10-9 M to 10-13 M). An antibody is said to "specifically bind" to VEGF when the antibody has a Kd of 1 μM or less.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, Clustal W, Megalign (DNAS-TAR) software or the FASTA program package. Those skilled in the art can determine appropriate parameters for aligning sequences, including any algorithms needed to achieve maximal alignment over the full length of the sequences being compared. For purposes herein, however, % amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36 and is publicly available from www.fasta.bioch.virginia.edu/fasta_www2/fasta_down.shtml or www. ebi.ac.uk/Tools/sss/fasta. Alternatively, a public server accessible at fasta.bioch.virginia.edu/fasta_www2/index.cgi can be used to compare the sequences, using the ggsearch (global protein: protein) program and default options (BLOSUM50; open: −10; ext: −2; Ktup=2) to ensure a global, rather than local, alignment is performed. Percent amino acid identity is given in the output alignment header.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "epitope" denotes the site on an antigen, either proteinaceous or non-proteinaceous, to which an anti-VEGF antibody binds. Epitopes can be formed both from contiguous amino acid stretches (linear epitope) or comprise non-contiguous amino acids (conformational epitope), e.g. coming in spatial proximity due to the folding of the antigen, i.e. by the tertiary folding of a proteinaceous antigen. Linear epitopes are typically still bound by an anti-VEGF antibody after exposure of the proteinaceous antigen to denaturing agents, whereas conformational epitopes are typically destroyed upon treatment with denaturing agents. An epitope comprises at least 3, at least 4, at least 5, at least 6, at least 7, or 8-10 amino acids in a unique spatial conformation.

Screening for antibodies binding to a particular epitope (i.e., those binding to the same epitope) can be done using methods routine in the art such as, e.g., without limitation, alanine scanning, peptide blots (see Meth. Mol. Biol. 248 (2004) 443-463), peptide cleavage analysis, epitope excision, epitope extraction, chemical modification of antigens (see Prot. Sci. 9 (2000) 487-496), and cross-blocking (see "Antibodies", Harlow and Lane (Cold Spring Harbor Press, Cold Spring Harb., NY).

Antigen Structure-based Antibody Profiling (ASAP), also known as Modification-Assisted Profiling (MAP), allows to bin a multitude of monoclonal antibodies specifically binding to VEGF based on the binding profile of each of the antibodies from the multitude to chemically or enzymatically modified antigen surfaces (see, e.g., US 2004/0101920). The antibodies in each bin bind to the same epitope which may be a unique epitope either distinctly different from or partially overlapping with epitope represented by another bin.

In some embodiments two antibodies are deemed to bind to the same epitope if essentially all amino acid mutations in the antigen that reduce or eliminate binding of one antibody also reduce or eliminate binding of the other. Two antibodies are deemed to have "overlapping epitopes" if only a subset of the amino acid mutations that reduce or eliminate binding of one antibody reduce or eliminate binding of the other.

An "immunoconjugate" is an antibody conjugated to one or more heterologous molecule(s), including but not limited to a cytotoxic agent.

The term "nucleic acid", "nucleic acid molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g. complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g. in a host or patient. Such DNA (e.g. cDNA) or RNA (e.g. mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g. Stadler ert al, Nature Medicine 2017, published online 12 Jun. 2017, doi:10.1038/nm.4356 or EP 2 101 823 B1).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-VEGF antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line", and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the pharmaceutical composition would be administered.

An "effective amount" of an agent, e.g., a pharmaceutical composition, refers to an amount effective, at dosages and for periods of time necessary, to achieve the desired therapeutic or prophylactic result.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

2. Detailed Description of the Embodiments of the Invention

In one aspect, the invention is based, in part, on the inhibition of angiogenesis using anti-VEGF antibodies. In certain embodiments, antibodies that bind to VEGF are provided. Antibodies of the invention are useful, e.g., for the diagnosis or treatment of VEGF-related diseases, such as e.g. cancer or eye diseases.

A. Exemplary Anti-VEGF Antibodies

In one aspect, the invention provides antibodies that bind to VEGF. In one aspect, provided are isolated antibodies that bind to VEGF. In one aspect, the invention provides antibodies that specifically bind to VEGF. In certain embodiments, an anti-VEGF antibody
  a) wherein binding of the antibody to VEGF significantly inhibits VEGF binding to VEGF receptor VEGF-R2 without significantly inhibiting VEGF binding to VEGF receptor VEGF-R1, and/or
  b) wherein the antibody binds VEGF with an affinity of ≤150 µM as measured by surface plasmon resonance at a temperature of 25° C., and wherein the antibody binds VEGF with a higher or with about the same affinity as measured by surface plasmon resonance at a temperature of 37° C.

In one aspect, the invention provides an anti-VEGF antibody comprising at least one, two, three, four, five, or six CDRs selected from (a) CDR-H1 comprising the amino acid sequence of SEQ ID NO:03; (b) CDR-H2 comprising the amino acid sequence of SEQ ID NO:04; (c) CDR-H3 comprising the amino acid sequence of SEQ ID NO:05; (d) CDR-L1 comprising the amino acid sequence of SEQ ID NO:06; (e) CDR-L2 comprising the amino acid sequence of SEQ ID NO:07; and (f) CDR-L3 comprising the amino acid sequence of SEQ ID NO:08. One exemplary antibody comprising this set of CDR amino acid sequences is the antibody referred to herein as "VEGF-0089".

In one aspect, the invention provides an antibody comprising at least one, at least two, or all three VH CDR sequences selected from (a) CDR-H1 comprising the amino acid sequence of SEQ ID NO:03; (b) CDR-H2 comprising the amino acid sequence of SEQ ID NO:04; and (c) CDR-H3 comprising the amino acid sequence of SEQ ID NO:05. In one embodiment, the antibody comprises CDR-H3 comprising the amino acid sequence of SEQ ID NO:05. In another embodiment, the antibody comprises CDR-H3 comprising the amino acid sequence of SEQ ID NO:05 and CDR-L3 comprising the amino acid sequence of SEQ ID NO:08. In a further embodiment, the antibody comprises CDR-H3 comprising the amino acid sequence of SEQ ID NO:05, CDR-L3 comprising the amino acid sequence of SEQ ID NO:08, and CDR-H2 comprising the amino acid sequence SEQ ID NO:04. In a further embodiment, the antibody comprises (a) CDR-H1 comprising the amino acid sequence of SEQ ID NO:03; (b) CDR-H2 comprising the amino acid sequence of SEQ ID NO:04; and (c) CDR-H3 comprising the amino acid sequence of SEQ ID NO:05.

In another aspect, the invention provides an antibody comprising at least one, at least two, or all three VL CDR sequences selected from (a) CDR-L1 comprising the amino acid sequence of SEQ ID NO:06; (b) CDR-L2 comprising the amino acid sequence of SEQ ID NO:07; and (c) CDR-L3 comprising the amino acid sequence of SEQ ID NO:08. In one embodiment, the antibody comprises (a) CDR-L1 comprising the amino acid sequence of SEQ ID NO:06; (b) CDR-L2 comprising the amino acid sequence of SEQ ID NO:07; and (c) CDR-L3 comprising the amino acid sequence of SEQ ID NO:08.

In another aspect, an antibody of the invention comprises (a) a VH domain comprising at least one, at least two, or all three VH CDR sequences selected from CDR sequences selected from (i) CDR-H1 comprising the amino acid sequence of SEQ ID NO:03; (ii) CDR-H2 comprising the amino acid sequence of SEQ ID NO:04; and (iii) CDR-H3 comprising the amino acid sequence of SEQ ID NO:05; and (b) a VL domain comprising at least one, at least two, or all three VL CDR sequences selected from (i) CDR-L1 comprising the amino acid sequence of SEQ ID NO:06; (ii) CDR-L2 comprising the amino acid sequence of SEQ ID NO:07; and (iii) CDR-L3 comprising the amino acid sequence of SEQ ID NO: 08.

In another aspect, an antibody of the invention comprises (a) a VH domain comprising (a) CDR-H1 comprising the amino acid sequence of SEQ ID NO:03; (b) CDR-H3 comprising the amino acid sequence of SEQ ID NO:05; and (b) a VL domain comprising (c) CDR-L1 comprising the amino acid sequence of SEQ ID NO:06; (d) CDR-L2 comprising the amino acid sequence of SEQ ID NO:07; and (e) CDR-L3 comprising the amino acid sequence of SEQ ID NO:08.

In another aspect, the invention provides an antibody comprising (a) CDR-H1 comprising the amino acid sequence of SEQ ID NO:03; (b) CDR-H2 comprising the amino acid sequence of SEQ ID NO:04; (c) CDR-H3 comprising the amino acid sequence of SEQ ID NO:05; (d) CDR-L1 comprising the amino acid sequence of SEQ ID NO:06; (e) CDR-L2 comprising the amino acid sequence of SEQ ID NO:07; and (f) CDR-L3 comprising the amino acid sequence of SEQ ID NO:08. One exemplary antibody comprising this set of CDR amino acid sequences is the antibody referred to herein as "VEGF-0089".

In certain embodiments, any one or more amino acids of an anti-VEGF antibody as provided above are mutated at the following CDR positions in CDR-H2 (SEQ ID NO:04): positions 4, 6, 7, and 8.

In certain embodiments, the substitutions are conservative substitutions or deletions, as provided herein. In certain embodiments, any one or more of the following substitutions or deletions may be made in any combination: in CDR-H2 (SEQ ID NO:04): positions N4S, G6P, a deletion of amino acid G at position 7, and I8F.

In another aspect, an antibody of the invention comprises (a) a VH domain comprising (i) CDR-H1 comprising the amino acid sequence of SEQ ID NO:03; (ii) CDR-H2 having at least 80% sequence identity to the amino acid sequence of SEQ ID NO:04; and (iii) CDR-H3 comprising the amino acid sequence of SEQ ID NO:05; and (b) a VL domain comprising (i) CDR-L1 comprising the amino acid sequence of SEQ ID NO:06; (ii) CDR-L2 comprising the amino acid sequence of SEQ ID NO:07; and (iii) CDR-L3 comprising the amino acid sequence of SEQ ID NO:08.

In another aspect, an antibody of the invention comprises (a) a VH domain comprising (i) CDR-H1 comprising the amino acid sequence of SEQ ID NO:03; (ii) CDR-H2 comprising the amino acid sequence of SEQ ID NO:30; and (iii) CDR-H3 comprising the amino acid sequence of SEQ ID NO:05; and (b) a VL domain comprising (i) CDR-L1 comprising the amino acid sequence of SEQ ID NO:06; (ii) CDR-L2 comprising the amino acid sequence of SEQ ID NO:07; and (iii) CDR-L3 comprising the amino acid sequence of SEQ ID NO:08. In the antibody according to this aspect of the invention CDR-H2 comprises the amino acid of SEQ ID NO:30, which is the following consensus sequence: SIGX$_1$GX$_2$X$_3$X$_4$YTYYADSVKG (SEQ ID NO:30), wherein X$_1$, X$_2$ and X$_4$ is selected independently from each other from any naturally occurring amino acid and wherein X$_3$ is selected from any naturally occurring amino acid or a gap (no amino acid).

In another aspect, an antibody of the invention comprises (a) a VH domain comprising (i) CDR-H1 comprising the amino acid sequence of SEQ ID NO:03; (ii) CDR-H2 comprising the amino acid sequence of SEQ ID NO:31; and (iii) CDR-H3 comprising the amino acid sequence of SEQ ID NO:05; and (b) a VL domain comprising (i) CDR-L1 comprising the amino acid sequence of SEQ ID NO:06; (ii) CDR-L2 comprising the amino acid sequence of SEQ ID NO:07; and (iii) CDR-L3 comprising the amino acid sequence of SEQ ID NO:08. In the antibody according to this aspect of the invention CDR-H2 comprises the amino acid of SEQ ID NO:31, which is the following consensus sequence: SIGX$_1$GX$_2$X$_3$X$_4$YTYYADSVKG (SEQ ID NO:31), wherein X$_1$ is selected from N or S, X$_2$ is selected from G or P, X$_3$ is either a gap (no amino acid) or G; and X$_4$ is selected from I or F.

In another aspect, the invention provides an antibody comprising (a) CDR-H1 comprising the amino acid sequence of SEQ ID NO:03; (b) CDR-H2 comprising the amino acid sequence of SEQ ID NO:10; (c) CDR-H3 comprising the amino acid sequence of SEQ ID NO:05; (d) CDR-L1 comprising the amino acid sequence of SEQ ID NO:06; (e) CDR-L2 comprising the amino acid sequence of SEQ ID NO:07; and (f) CDR-L3 comprising the amino acid sequence of SEQ ID NO:08. Exemplary antibodies comprising this set of CDR amino acid sequences are the antibodies referred to herein as "VEGF-0113" and "VEGF-P1AE3520".

In another aspect, the invention provides an antibody comprising (a) CDR-H1 comprising the amino acid sequence of SEQ ID NO:03; (b) CDR-H2 comprising the amino acid sequence of SEQ ID NO:12; (c) CDR-H3 comprising the amino acid sequence of SEQ ID NO:05; (d) CDR-L1 comprising the amino acid sequence of SEQ ID NO:06; (e) CDR-L2 comprising the amino acid sequence of SEQ ID NO:07; and (f) CDR-L3 comprising the amino acid sequence of SEQ ID NO:08. Exemplary antibodies comprising this set of CDR amino acid sequences are the antibodies referred to herein as "VEGF-0114" and "VEGF-P1AE3521".

In one embodiment, an anti-VEGF antibody further comprises an acceptor human framework, e.g. a human immunoglobulin framework or a human consensus framework.

In another aspect, an anti-VEGF antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:01. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-VEGF antibody comprising that sequence retains the ability to bind to VEGF. In certain embodiments, a total of 1 to 10 amino acids have been substituted, inserted and/or deleted in SEQ ID NO:01. In certain embodiments, substitutions, insertions, or deletions occur in regions outside the CDRs (i.e., in the FRs). Optionally, the anti-VEGF antibody comprises the VH sequence in SEQ ID NO:01, including post-translational modifications of that sequence. In a particular embodiment, the VH comprises one, two or three CDRCDRs selected from: (a) CDRCDR-H1 comprising the amino acid sequence of SEQ ID NO:03, (b) CDR-H2 comprising the amino acid sequence of SEQ ID NO:04, and (c) CDR-H3 comprising the amino acid sequence of SEQ ID NO:05.

In another aspect, an anti-VEGF antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO:02. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-VEGF antibody comprising that sequence retains the ability to bind to VEGF. In certain embodiments, a total of 1 to 10 amino acids have been substituted, inserted and/or deleted in SEQ ID NO:02. In certain embodiments, the substitutions, insertions, or deletions occur in regions outside the CDRs (i.e., in the FRs).

Optionally, the anti-VEGF antibody comprises the VL sequence in SEQ ID NO:02, including post-translational modifications of that sequence. In a particular embodiment, the VL comprises one, two or three CDRs selected from (a) CDR-L1 comprising the amino acid sequence of SEQ ID NO:06; (b) CDR-L2 comprising the amino acid sequence of SEQ ID NO:07; and (c) CDR-L3 comprising the amino acid sequence of SEQ ID NO:08.

In another aspect, an anti-VEGF antibody is provided, wherein the antibody comprises a VH sequence as in any of the embodiments provided above, and a VL sequence as in any of the embodiments provided above. In one embodiment, the antibody comprises the VH and VL sequences in SEQ ID NO:01 and SEQ ID NO:02, respectively, including post-translational modifications of those sequences. In one embodiment, the antibody comprises a VH domain of SEQ ID NO:01 and a VL domain of SEQ ID NO:02. One exemplary antibody comprising said VH and VL domains is the antibody referred to herein as "VEGF-0089".

In another aspect, an anti-VEGF antibody is provided, wherein the antibody comprises a VH sequence as in any of the embodiments provided above, and a VL sequence as in any of the embodiments provided above. In one embodiment, the antibody comprises the VH and VL sequences in SEQ ID NO:33 and SEQ ID NO:02, respectively, including post-translational modifications of those sequences. In one embodiment, the antibody comprises a VH domain of SEQ ID NO:33 and a VL domain of SEQ ID NO:02. One exemplary antibody comprising said VH and VL domains is the antibody referred to herein as "VEGF-P1AD8675".

In another aspect, an anti-VEGF antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:09. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-VEGF antibody comprising that sequence retains the ability to bind to VEGF. In certain embodiments, a total of 1 to 10 amino acids have been substituted, inserted and/or deleted in SEQ ID NO:09. In certain embodiments, substitutions, insertions, or deletions occur in regions outside the CDRs (i.e., in the FRs). Optionally, the anti-VEGF antibody comprises the VH sequence in SEQ ID NO:09, including post-translational modifications of that sequence. In a particular embodiment, the VH comprises one, two or three CDRs selected from: (a) CDR-H1 comprising the amino acid sequence of SEQ ID NO:03, (b) CDR-H2 comprising the amino acid sequence of SEQ ID NO:10, and (c) CDR-H3 comprising the amino acid sequence of SEQ ID NO:05.

In another aspect, an anti-VEGF antibody is provided, wherein the antibody comprises a VH sequence as in any of the embodiments provided above, and a VL sequence as in any of the embodiments provided above. In one embodiment, the antibody comprises the VH and VL sequences in SEQ ID NO:09 and SEQ ID NO:02, respectively, including post-translational modifications of those sequences. In one embodiment, the antibody comprises a VH domain of SEQ ID NO:09 and a VL domain of SEQ ID NO:02. One exemplary antibody comprising said VH and VL domains is the antibody referred to herein as "VEGF-0113".

In another aspect, an anti-VEGF antibody is provided, wherein the antibody comprises a VH sequence as in any of the embodiments provided above, and a VL sequence as in any of the embodiments provided above. In one embodiment, the antibody comprises the VH and VL sequences in SEQ ID NO:43 and SEQ ID NO:02, respectively, including post-translational modifications of those sequences. In one embodiment, the antibody comprises a VH domain of SEQ ID NO:43 and a VL domain of SEQ ID NO:02. One exemplary antibody comprising said VH and VL domains is the antibody referred to herein as "VEGF-P1AE3520". In another aspect, an anti-VEGF antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:11. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-VEGF antibody comprising that sequence retains the ability to bind to VEGF. In certain embodiments, a total of 1 to 10 amino acids have been substituted, inserted and/or deleted in SEQ ID NO:11. In certain embodiments, substitutions, insertions, or deletions occur in regions outside the CDRs (i.e., in the FRs). Optionally, the anti-VEGF antibody comprises the VH sequence in SEQ ID NO:11, including post-translational modifications of that sequence. In a particular embodiment, the VH comprises one, two or three CDRs selected from: (a) CDR-H1 comprising the amino acid sequence of SEQ ID NO:03, (b) CDR-H2 comprising the amino acid sequence of SEQ ID NO:12, and (c) CDR-H3 comprising the amino acid sequence of SEQ ID NO:05.

In another aspect, an anti-VEGF antibody is provided, wherein the antibody comprises a VH sequence as in any of the embodiments provided above, and a VL sequence as in any of the embodiments provided above. In one embodiment, the antibody comprises the VH and VL sequences in SEQ ID NO:11 and SEQ ID NO:02, respectively, including post-translational modifications of those sequences. In one embodiment, the antibody comprises a VH domain of SEQ ID NO:11 and a VL domain of SEQ ID NO:02. One exemplary antibody comprising said VH and VL domains is the antibody referred to herein as "VEGF-0114".

In another aspect, an anti-VEGF antibody is provided, wherein the antibody comprises a VH sequence as in any of the embodiments provided above, and a VL sequence as in any of the embodiments provided above. In one embodiment, the antibody comprises the VH and VL sequences in SEQ ID NO:45 and SEQ ID NO:02, respectively, including post-translational modifications of those sequences. In one embodiment, the antibody comprises a VH domain of SEQ ID NO:45 and a VL domain of SEQ ID NO:02. One exemplary antibody comprising said VH and VL domains is the antibody referred to herein as "VEGF-P1AE3521".

In one embodiment of all aspects the antibody comprises CDR-H2 comprising the amino acid sequence selected from the group of SEQ ID NO:04, SEQ ID NO:10, and SEQ ID NO: 12.

In one embodiment of all aspects the antibody comprises H-FR3 comprising the amino acid sequence selected from the group of SEQ ID NO: 46 and SEQ ID NO: 47.

In a further aspect, the invention provides an antibody that binds to the same epitope as an anti-VEGF antibody provided herein. For example, in certain embodiments, an antibody is provided that binds to the same epitope as an anti-VEGF antibody comprising a VH sequence of SEQ ID NO:01 and a VL sequence of SEQ ID NO:02. In one embodiment said anti-VEGF antibody binds to the same epitope than antibody VEGF-0089 as described herein, as measured by x-ray crystallography. In one embodiment said anti-VEGF antibody binds to the same epitope than antibody VEGF-0089 as described herein, as measured by x-ray crystallography as described in Example 13. In one embodiment an antibody is provided that binds to a conformational epitope on a dimer of VEGF-A121, wherein VEGF-A121 comprises an amino acid sequence of SEQ ID NO: 45, wherein the epitope comprises in one of the individual VEGF-A121 molecules within the VEGF dimer amino acids F17, M18, D19, Y21, Q22, R23, Y25, H27, P28, I29, E30, M55, N62, L66, N100, K101, C102, E103, C104, R105 and P106; and in the other one of the individual VEGF-A121 molecules within the VEGF dimer amino acids E30, K48, M81 and Q87. The numbering is according to the position of the amino acid in the amino acid sequence of VEGF-A121 indicated in SEQ ID NO: 45 (see also FIG. 13). In one embodiment the epitope is measured by x-ray crystallography.

In a further aspect of the invention, an anti-VEGF antibody according to any of the above embodiments is a monoclonal antibody, including a human antibody. In one embodiment, an anti-VEGF antibody is an antibody fragment, e.g., a Fv, Fab, Fab', scFv, diabody, or F(ab')2 fragment. In one embodiment, an anti-VEGF antibody is a Fab fragment. In another embodiment, the antibody is a full length antibody, e.g., an intact IgG1 antibody or other antibody class or isotype as defined herein.

In a further aspect, an anti-VEGF antibody according to any of the above embodiments may incorporate any of the features, singly or in combination, as described in Sections 1-6 below:

1. Antibody Affinity

In certain embodiments, an antibody provided herein has a dissociation constant (Kd) of $\leq 1$ µM, $\leq 100$ nM, $\leq 10$ nM, or $\leq 1$ nM (e.g. $10^{-8}$ M or less, e.g. from $10^{-8}$ M to $10^{-13}$ M, e.g., from $10^{-9}$ M to $10^{-13}$ M).

In one embodiment, an antibody provided herein binds VEGF with an affinity of $\leq 150$ pM (i.e. has a dissociation constant (Kd) of $\leq 150$ pM).

In one embodiment, a Fab fragment of an antibody provided herein binds VEGF with an affinity of $\leq 150$ pM (i.e. has a dissociation constant (Kd) of $\leq 150$ pM). In one embodiment, an antibody provided herein binds VEGF with an affinity of $\leq 150$ pM as measured by surface plasmon resonance at a temperature of 25° C. In one embodiment, an antibody provided herein binds VEGF with an affinity of $\leq 150$ pM as measured by surface plasmon resonance at a temperature of 37° C. In one embodiment, an antibody provided herein binds VEGF with an affinity of $\leq 150$ pM as measured by surface plasmon resonance at a temperature of 25° C. and 37° C.

In one embodiment, an antibody provided herein binds VEGF with an affinity of $\leq 150$ pM as measured by surface plasmon resonance at a temperature of 25° C. and the antibody binds VEGF with a higher or with about the same affinity at a temperature of 37° C. as measured by surface plasmon resonance. With "about the same affinity" is meant that the affinity (i.e. the Kd) of the antibody at 37° C. is within the range of +/−5% of the affinity (i.e. the Kd) of the antibody at 25° C.

In one embodiment, Kd is measured using a BIACORE® surface plasmon resonance assay. In one embodiment Kd is measured using a surface plasmon resonance assay as described in Example 2.

For example, an assay using a BIACORE®-T-200 a BIACORE®-8k (BIAcore, Inc., Uppsala) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., J. Mol. Biol. 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. The term "antibody fragment" refers to a molecule other than an intact antibody that comprises a portion of an intact antibody that retains the ability to specifically bind to an antigen. Antibody fragments include, but are not limited to Fab, Fab', Fab'-SH, F(ab')$_2$, Fv, single-chain Fab (scFab); single-chain variable fragments (scFv) and single domain antibodies (dAbs). For a review of certain antibody fragments, see Holliger and Hudson, Nature Biotechnology 23:1126-1136 (2005).

In one embodiment, the antibody fragment is a Fab, Fab', Fab'-SH, or F(ab')$_2$ fragment, in particular a Fab fragment. Papain digestion of intact antibodies produces two identical antigen-binding fragments, called "Fab" fragments containing each the heavy- and light-chain variable domains (VH and VL, respectively) and also the constant domain of the light chain (CL) and the first constant domain of the heavy chain (CH1). The term "Fab fragment" thus refers to an antibody fragment comprising a light chain comprising a VL domain and a CL domain, and a heavy chain fragment comprising a VH domain and a CH1 domain. Fab' fragments differ from Fab fragments by the addition of residues at the carboxy terminus of the CH1 domain including one or more cysteines from the antibody hinge region. Fab'-SH are Fab' fragments in which the cysteine residue(s) of the constant domains bear a free thiol group. Pepsin treatment yields an F(ab')$_2$ fragment that has two antigen-binding sites (two Fab fragments) and a part of the Fc region. For discussion of Fab and F(ab')$_2$ fragments comprising salvage receptor binding epitope residues and having increased in vivo half-life, see U.S. Pat. No. 5,869,046.

In another embodiment, the antibody fragment is a diabody, a triabody or a tetrabody. Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448

(1993). Triabodies and tetrabodies are also described in Hudson et al., Nat. Med. 9:129-134 (2003).

In a further embodiment, the antibody fragment is a single chain Fab fragment. A "single chain Fab fragment" or "scFab" is a polypeptide consisting of an antibody heavy chain variable domain (VH), an antibody heavy chain constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL. In particular, said linker is a polypeptide of at least 30 amino acids, preferably between 32 and 50 amino acids. Said single chain Fab fragments are stabilized via the natural disulfide bond between the CL domain and the CH1 domain. In addition, these single chain Fab fragments might be further stabilized by generation of interchain disulfide bonds via insertion of cysteine residues (e.g. position 44 in the variable heavy chain and position 100 in the variable light chain according to Kabat numbering).

In another embodiment, the antibody fragment is single-chain variable fragment (scFv). A "single-chain variable fragment" or "scFv" is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., Pluückthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458.

Antibody fragments can be made by various techniques, including but not limited to proteolytic digestion of an intact antibody as well as recombinant production by recombinant host cells (e.g. E. coli), as described herein.

3. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

4. Multispecific Antibodies

In certain embodiments, an antibody provided herein is a multispecific antibody, e.g. a bispecific antibody. Multispecific antibodies are monoclonal antibodies that have binding specificities for at least two different sites, i.e., different epitopes on different antigens or different epitopes on the same antigen. In certain embodiments, the multispecific antibody has three or more binding specificities. In certain embodiments, one of the binding specificities is for VEGF and the other (two or more) specificity is for any other antigen. In certain embodiments, bispecific antibodies may bind to two (or more) different epitopes of VEGF. Multi-specific (e.g., bispecific) antibodies may also be used to localize cytotoxic agents or cells to cells which express VEGF. Multispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)) and "knob-in-hole" engineering (see, e.g., U.S. Pat. No. 5,731,168, and Atwell et al., J. Mol. Biol. 270:26 (1997)). Multi-specific antibodies may also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992) and WO 2011/034605); using the common light chain technology for circumventing the light chain mis-pairing problem (see, e.g., WO 98/50431); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more antigen binding sites, including for example, "Octopus antibodies", or DVD-Ig are also included herein (see, e.g. WO 2001/77342 and WO 2008/024715). Other examples of multispecific antibodies with three or more antigen binding sites can be found in WO 2010/115589, WO 2010/112193, WO 2010/136172, WO2010/145792, and WO 2013/026831.

Multi-specific antibodies may also be provided in an asymmetric form with a domain crossover in one or more binding arms of the same antigen specificity, i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). In one embodiment, the multispecific antibody comprises a cross-Fab fragment. The term "cross-Fab fragment" or "crossover Fab fragment" refers to a Fab fragment, wherein either the variable regions or the constant regions of the heavy and light chain are exchanged. A cross-Fab fragment comprises a polypeptide chain composed of the light chain variable region (VL) and the heavy chain constant region 1 (CH1), and a polypeptide chain composed of the heavy chain variable region (VH) and the light chain constant region (CL). Asymmetrical Fab arms can also be engineered by introducing charged or non-charged amino acid mutations into domain interfaces to direct correct Fab pairing. See e.g., WO 2016/172485.

Various further molecular formats for multispecific antibodies are known in the art and are included herein (see e.g., Spiess et al., Mol Immunol 67 (2015) 95-106).

5. Antibody Variants

In certain embodiments, amino acid sequence variants of the antibodies provided herein are contemplated. For example, it may be desirable to alter the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs (e.g. CDRs) and FRs. Conservative substitutions are shown in Table I under the heading of "preferred substitutions". More substantial changes are provided in Table I under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE I

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for a member of another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR (e.g. CDR) residues are mutated and the variant antibodies displayed on phage and screened for a particular biological activity (e.g. binding affinity).

Alterations (e.g., substitutions) may be made in HVRs (e.g. CDRs), e.g., to improve antibody affinity. Such alterations may be made in HVR "hotspots", i.e., residues encoded by codons that undergo mutation at high frequency during the somatic maturation process (see, e.g., Chowdhury, Methods Mol. Biol. 207:179-196 (2008)), and/or residues that contact antigen, with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR (e.g. CDR)-directed approaches, in which several HVR residues (e.g., 4-6 residues at a time) are randomized. HVR (e.g. CDR) residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs (e.g. CDRs) so long as such alterations do not substantially reduce the ability of the antibody to bind antigen. For example, conservative alterations (e.g., conservative substitutions as provided herein) that do not substantially reduce binding affinity may be made in HVRs (e.g. CDRs). Such alterations may, for example, be outside of antigen contacting residues in the HVRs (e.g. CDRs). In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT (antibody directed enzyme prodrug therapy)) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one embodiment, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. Arch. Biochem. Biophys. 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. Biotech. Bioeng. 87:614-622 (2004); Kanda, Y. et al., Biotechnol. Bioeng., 94(4):680-688 (2006); and WO2003/085107), or cells with reduced or abolished activity of a GDP-fucose synthesis or transporter protein (see, e.g., US2004259150, US2005031613, US2004132140, US2004110282).

In a further embodiment, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement-dependent cytotoxicity (CDC) and antibody-dependent cell-mediated cytotoxicity (ADCC)) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006); WO 2013/120929 A1).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No.

6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In certain embodiments, an antibody variant comprises an Fc region with one or more amino acid substitutions which diminish FcγR binding, e.g., substitutions at positions 234 and 235 of the Fc region (EU numbering of residues). In one embodiment the substitutions are L234A and L235A (LALA). In certain embodiments, the antibody variant further comprises D265A and/or P329G in an Fc region derived from a human IgG1 Fc region. In one embodiment the substitutions are L234A, L235A and P329G (LALA-PG) in an Fc region derived from a human IgG1 Fc region. (See, e.g., WO 2012/130831). In another embodiment, the substitutions are L234A, L235A and D265A (LALA-DA) in an Fc region derived from a human IgG1 Fc region.

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934 (Hinton et al.). Those antibodies comprise an Fc region with one or more substitutions therein which improve binding of the Fc region to FcRn. Such Fc variants include those with substitutions at one or more of Fc region residues: 238, 252, 254, 256, 265, 272, 286, 303, 305, 307, 311, 312, 317, 340, 356, 360, 362, 376, 378, 380, 382, 413, 424 or 434, e.g., substitution of Fc region residue 434 (See, e.g., U.S. Pat. No. 7,371,826; Dall'Acqua, W. F., et al. J. Biol. Chem. 281 (2006) 23514-23524).

Fc region residues critical to the mouse Fc-mouse FcRn interaction have been identified by site-directed mutagenesis (see e.g. Dall'Acqua, W. F., et al. J. Immunol 169 (2002) 5171-5180). Residues I253, H310, H433, N434, and H435 (EU numbering according to Kabat) are involved in the interaction (Medesan, C., et al., Eur. J. Immunol. 26 (1996) 2533; Firan, M., et al., Int. Immunol. 13 (2001) 993; Kim, J. K., et al., Eur. J. Immunol. 24 (1994) 542). Residues I253, H310, and H435 were found to be critical for the interaction of human Fc with murine FcRn (Kim, J. K., et al., Eur. J. Immunol. 29 (1999) 2819). Studies of the human Fc-human FcRn complex have shown that residues I253, S254, H435, and Y436 are crucial for the interaction (Firan, M., et al., Int. Immunol. 13 (2001) 993; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined.

In certain embodiments, an antibody variant comprises an Fc region with one or more amino acid substitutions, which reduce FcRn binding, e.g., substitutions at positions 253, and/or 310, and/or 435 of the Fc-region (EU numbering of residues). In certain embodiments, the antibody variant comprises an Fc region with the amino acid substitutions at positions 253, 310 and 435. In one embodiment the substitutions are I253A, H310A and H435A in an Fc region derived from a human IgG1 Fc-region. See e.g., Grevys, A., et al., J. Immunol. 194 (2015) 5497-5508.

In certain embodiments, an antibody variant comprises an Fc region with one or more amino acid substitutions, which reduce FcRn binding, e.g., substitutions at positions 310, and/or 433, and/or 436 of the Fc region (EU numbering of residues). In certain embodiments, the antibody variant comprises an Fc region with the amino acid substitutions at positions 310, 433 and 436. In one embodiment the substitutions are H310A, H433A and Y436A in an Fc region derived from a human IgG1 Fc-region. (See, e.g., WO 2014/177460 A1).

In certain embodiments, an antibody variant comprises an Fc region with one or more amino acid substitutions which increase FcRn binding, e.g., substitutions at positions 252, and/or 254, and/or 256 of the Fc region (EU numbering of residues). In certain embodiments, the antibody variant comprises an Fc region with amino acid substitutions at positions 252, 254, and 256. In one embodiment the substitutions are M252Y, S254T and T256E in an Fc region derived from a human IgG1 Fc-region.

See also Duncan & Winter, Nature 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., THIOMAB™ antibodies, in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. Nos. 7,521,541, 830,930, 7,855,275, 9,000,130, or WO2016040856.

6. Immunoconjugates

The invention also provides immunoconjugates comprising an anti-VEGF antibody herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in Pharmacol Review 68:3-19 (2016).

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates.

Examples include $At^{21}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example Ttc-99m or $I^{123}$ or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

B. Recombinant Methods and Compositions

Antibodies may be produced using recombinant methods and compositions, e.g., as described in U.S. Pat. No. 4,816,567. For these methods one or more isolated nucleic acid(s) encoding an antibody are provided.

In case of a native antibody or native antibody fragment two nucleic acids are required, one for the light chain or a fragment thereof and one for the heavy chain or a fragment thereof. Such nucleic acid(s) encode an amino acid sequence comprising the VL and/or an amino acid sequence comprising the VH of the antibody (e.g., the light and/or heavy chain(s) of the antibody). These nucleic acids can be on the same expression vector or on different expression vectors.

In case of a bispecific antibody with heterodimeric heavy chains four nucleic acids are required, one for the first light chain, one for the first heavy chain comprising the first heteromonomeric Fc-region polypeptide, one for the second light chain, and one for the second heavy chain comprising the second heteromonomeric Fc-region polypeptide. The four nucleic acids can be comprised in one or more nucleic acid molecules or expression vectors. Such nucleic acid(s) encode an amino acid sequence comprising the first VL and/or an amino acid sequence comprising the first VH including the first heteromonomeric Fc-region and/or an amino acid sequence comprising the second VL and/or an amino acid sequence comprising the second VH including the second heteromonomeric Fc-region of the antibody (e.g., the first and/or second light and/or the first and/or second heavy chains of the antibody). These nucleic acids can be on the same expression vector or on different expression vectors, normally these nucleic acids are located on two or three expression vectors, i.e. one vector can comprise more than one of these nucleic acids. Examples of these bispecific antibodies are CrossMabs (see, e.g. Schaefer, W. et al, PNAS, 108 (2011) 11187-1191). For example, one of the heteromonomeric heavy chain comprises the so-called "knob mutations" (T366W and optionally one of S354C or Y349C) and the other comprises the so-called "hole mutations" (T366S, L368A and Y407V and optionally Y349C or S354C) (see, e.g., Carter, P. et al., Immunotechnol. 2 (1996) 73) according to Kabat EU numbering.

In one embodiment isolated nucleic acids encoding an antibody as used in the methods as reported herein are provided.

In one embodiment, a method of making an anti-VEGF antibody is provided, wherein the method comprises culturing a host cell comprising nucleic acid(s) encoding the antibody, as provided above, under conditions suitable for expression of the antibody, and optionally recovering the antibody from the host cell (or host cell culture medium).

For recombinant production of an anti-VEGF antibody, nucleic acids encoding the antibody, e.g., as described above, are isolated and inserted into one or more vectors for further cloning and/or expression in a host cell. Such nucleic acids may be readily isolated and sequenced using conventional procedures (e.g., by using oligonucleotide probes that are capable of binding specifically to genes encoding the heavy and light chains of the antibody) or produced by recombinant methods or obtained by chemical synthesis.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, NJ (2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized", resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of (glycosylated) antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells (as described, e.g., in Mather, J. P. et al., Annals N.Y. Acad. Sci. 383 (1982) 44-68); MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

In one embodiment, the host cell is eukaryotic, e.g. a Chinese Hamster Ovary (CHO) cell or lymphoid cell (e.g., Y0, NS0, Sp20 cell).

C. Binding Assays

Anti-VEGF antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, Western blot, etc.

In another aspect, competition assays may be used to identify an antibody that competes with an antibody comprising a VH domain of SEQ ID NO:01 and a VL domain of SEQ ID NO:02 for binding to VEGF.

In an exemplary competition assay, immobilized VEGF is incubated in a solution comprising a first labeled antibody that binds to VEGF that comprises a VH domain of SEQ ID NO:01 and a VL domain of SEQ ID NO:02 (e.g. anti-VEGF-0089) and a second unlabeled antibody that is being tested for its ability to compete with the first antibody for binding to VEGF. The second antibody may be present in a hybridoma supernatant. As a control, immobilized VEGF is incubated in a solution comprising the first labeled antibody but not the second unlabeled antibody. After incubation under conditions permissive for binding of the first antibody to VEGF, excess unbound antibody is removed, and the amount of label associated with immobilized VEGF is measured. If the amount of label associated with immobilized VEGF is substantially reduced in the test sample relative to the control sample, then that indicates that the second antibody is competing with the first antibody for binding to VEGF. See Harlow and Lane (1988) Antibodies: A Laboratory Manual ch. 14 (Cold Spring Harbor Laboratory, Cold Spring Harbor, NY).

D. Pharmaceutical Compositions

In a further aspect, provided are pharmaceutical compositions comprising any of the antibodies provided herein, e.g., for use in any of the below therapeutic methods. In one aspect, a pharmaceutical composition comprises any of the antibodies provided herein and a pharmaceutically acceptable carrier. In another aspect, a pharmaceutical composition comprises any of the antibodies provided herein and at least one additional therapeutic agent, e.g., as described below.

Pharmaceutical compositions of an anti-VEGF antibody as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized compositions or aqueous solutions. Pharmaceutically acceptable carriers are generally nontoxic to recipients at the dosages and concentrations employed, and include, but are not limited to: buffers such as histidine, phosphate, citrate, acetate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Halozyme, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody compositions are described in U.S. Pat. No. 6,267,958. Aqueous antibody compositions include those described in U.S. Pat. No. 6,171, 586 and WO2006/044908, the latter compositions including a histidine-acetate buffer.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Pharmaceutical compositions for sustained-release may be prepared. Suitable examples of sustained-release preparations include semipermeable matrices of solid hydrophobic polymers containing the antibody, which matrices are in the form of shaped articles, e.g. films, or microcapsules.

The pharmaceutical compositions to be used for in vivo administration are generally sterile. Sterility may be readily accomplished, e.g., by filtration through sterile filtration membranes.

E. Therapeutic Methods and Routes of Administration

Any of the anti-VEGF antibodies provided herein may be used in therapeutic methods.

In one aspect, an anti-VEGF antibody for use as a medicament is provided. In further aspects, an anti-VEGF antibody for use in treating a VEGF-related disease, e.g. cancer or an eye disease, is provided. In certain embodiments, an anti-VEGF antibody for use in a method of treatment is provided. In certain embodiments, the invention provides an anti-VEGF antibody for use in a method of treating an individual having a VEGF-related disease, e.g. cancer or an eye disease, comprising administering to the individual an effective amount of the anti-VEGF antibody. In one such embodiment, the method further comprises administering to the individual an effective amount of at least one additional therapeutic agent (e.g. one, two, three, four, five, or six additional therapeutic agents), e.g., as described below. In further embodiments, the invention provides an anti-VEGF antibody for use in inhibiting angiogenesis. In certain embodiments, the invention provides an anti-VEGF antibody for use in a method of inhibiting angiogenesis in an individual comprising administering to the individual an effective amount of the anti-VEGF antibody to inhibit angiogenesis. An "individual" according to any of the above embodiments is preferably a human.

In a further aspect, the invention provides for the use of an anti-VEGF antibody in the manufacture or preparation of a medicament. In one embodiment, the medicament is for treatment of a VEGF-related disease, e.g. cancer or an eye disease. In a further embodiment, the medicament is for use in a method of treating a VEGF-related disease, e.g. cancer or an eye disease, comprising administering to an individual having the VEGF-related disease, e.g. cancer or eye disease, an effective amount of the medicament. In one such embodiment, the method further comprises administering to the individual an effective amount of at least one additional therapeutic agent, e.g., as described below. In a further embodiment, the medicament is for inhibiting angiogenesis. In a further embodiment, the medicament is for use in a method of inhibiting angiogenesis in an individual comprising administering to the individual an effective amount of the medicament to inhibit angiogenesis. An "individual" according to any of the above embodiments may be a human.

In a further aspect, the invention provides a method for treating a VEGF-related disease, e.g. cancer or an eye disease. In one embodiment, the method comprises administering to an individual having such VEGF-related disease, e.g. cancer or eye disease, an effective amount of an anti-VEGF antibody. In one such embodiment, the method further comprises administering to the individual an effective amount of at least one additional therapeutic agent, as described below. An "individual" according to any of the above embodiments may be a human.

In a further aspect, the invention provides a method for inhibiting angiogenesis in an individual. In one embodiment, the method comprises administering to the individual an effective amount of an anti-VEGF antibody to inhibit angiogenesis. In one embodiment, an "individual" is a human.

In a further aspect, the invention provides pharmaceutical compositions comprising any of the anti-VEGF antibodies provided herein, e.g., for use in any of the above therapeutic methods. In one embodiment, a pharmaceutical composition comprises any of the anti-VEGF antibodies provided herein and a pharmaceutically acceptable carrier. In another embodiment, a pharmaceutical composition comprises any of the anti-VEGF antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the pharmaceutical composition, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-0mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

F. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

3. Specific Embodiments of the Invention

In the following specific embodiments of the invention are listed.
1. An antibody that binds to VEGF, wherein binding of the antibody to VEGF significantly inhibits VEGF binding to VEGF receptor VEGF-R2 without significantly inhibiting VEGF binding to VEGF receptor VEGF-R1.
2. An antibody that binds to VEGF, wherein the antibody binds VEGF with an affinity of ≤150 pM at a temperature of 25° C. as measured by surface plasmon resonance, and wherein the antibody binds VEGF with a higher or with about the same affinity at a temperature of 37° C. as measured by surface plasmon resonance.
3. An antibody that binds to VEGF,
   a) wherein binding of the antibody to VEGF significantly inhibits VEGF binding to VEGF receptor VEGF-R2 without significantly inhibiting VEGF binding to VEGF receptor VEGF-R1; and/or
   b) wherein the antibody binds VEGF with an affinity of ≤150 pM at a temperature of 25° C. as measured by surface plasmon resonance, and wherein the antibody binds VEGF with a higher or with about the same affinity at a temperature of 37° C. as measured by surface plasmon resonance.
4. The antibody of one of embodiments 1 to 3, wherein binding of a Fab fragment of the antibody significantly inhibits VEGF binding to VEGF receptor VEGF-R2 without significantly inhibiting VEGF binding to VEGF receptor VEGF-R1.
5. The antibody of one of embodiments 1 to 4, wherein a Fab fragment of the antibody antibody binds VEGF with an affinity of ≤150 pM as measured by surface plasmon resonance at a temperature of 25° C. and as measured by surface plasmon resonance at a temperature of 37° C.
6. An antibody that binds to VEGF, wherein the antibody comprises a heavy chain variable domain (VH) comprising
   (a) CDR-H1 comprising the amino acid sequence of SEQ ID NO:03,
   (b) CDR-H2 comprising the amino acid sequence selected from the group of SEQ ID NO:04, SEQ ID NO:10, and SEQ ID NO: 12, and
   (c) CDR-H3 comprising the amino acid sequence of SEQ ID NO:05, and wherein the antibody comprises a light chain variable domain (VL) comprising
   (d) CDR-L1 comprising the amino acid sequence of SEQ ID NO:06,
   (e) CDR-L2 comprising the amino acid sequence of SEQ ID NO:07, and
   (f) CDR-L3 comprising the amino acid sequence of SEQ ID NO:08.
7. The antibody of one of embodiments 1 to 5, wherein the antibody comprises a heavy chain variable domain (VH) comprising
   (a) CDR-H1 comprising the amino acid sequence of SEQ ID NO:03,
   (b) CDR-H2 comprising the amino acid sequence selected from the group of SEQ ID NO:04, SEQ ID NO:10, and SEQ ID NO: 12, and
   (c) CDR-H3 comprising the amino acid sequence of SEQ ID NO:05, and wherein the antibody comprises a light chain variable domain (VL) comprising
   (d) CDR-L1 comprising the amino acid sequence of SEQ ID NO:06,
   (e) CDR-L2 comprising the amino acid sequence of SEQ ID NO:07, and
   (f) CDR-L3 comprising the amino acid sequence of SEQ ID NO:08.
8. The antibody of any of embodiments 1 to 7, which is a monoclonal antibody.
9. The antibody of any one of embodiments 1 to 8, which is a human antibody.
10. The antibody of any one of embodiments 1 to 9, which is an antibody fragment that binds VEGF.
11. The antibody of any of embodiments 1 to 10, comprising a VH sequence having at least 95% sequence identity to the amino acid sequence of SEQ ID NO:01; and a VL sequence having at least 95% sequence identity to the amino acid sequence of SEQ ID NO:02.
12. The antibody of any of embodiments 1 to 11, comprising a VH sequence having at least 95% sequence identity to the amino acid sequence of SEQ ID NO:01; and a VL sequence of SEQ ID NO:02.
13. The antibody of any of embodiments 1 to 12, comprising a VH sequence of SEQ ID NO: 01 and a VL sequence of SEQ ID NO: 02.
14. The antibody of any of embodiments 1 to 12, comprising a VH sequence of SEQ ID NO: 09 and a VL sequence of SEQ ID NO: 02.
15. The antibody of any of embodiments 1 to 12, comprising a VH sequence of SEQ ID NO: 11 and a VL sequence of SEQ ID NO: 02.
16. The antibody of any of embodiments 1 to 12, comprising a VH sequence of SEQ ID NO: 33 and a VL sequence of SEQ ID NO: 02.
17. The antibody of any of embodiments 1 to 12, comprising a VH sequence of SEQ ID NO: 42 and a VL sequence of SEQ ID NO: 02.
18. The antibody of any of embodiments 1 to 12, comprising a VH sequence of SEQ ID NO: 44 and a VL sequence of SEQ ID NO: 02.
19. An antibody that specifically binds to VEGF comprising a VH sequence of SEQ ID NO: 01 and a VL sequence of SEQ ID NO: 02.

20. An antibody that specifically binds to VEGF comprising a VH sequence of SEQ ID NO: 09 and a VL sequence of SEQ ID NO: 02.
21. An antibody that specifically binds to VEGF comprising a VH sequence of SEQ ID NO: 11 and a VL sequence of SEQ ID NO: 02.
22. An antibody that specifically binds to VEGF comprising a VH sequence of SEQ ID NO: 33 and a VL sequence of SEQ ID NO: 02.
23. An antibody that specifically binds to VEGF comprising a VH sequence of SEQ ID NO: 42 and a VL sequence of SEQ ID NO: 02.
24. An antibody that specifically binds to VEGF comprising a VH sequence of SEQ ID NO: 44 and a VL sequence of SEQ ID NO: 02.
25. The antibody of any of embodiments 1 to 24, which is a full length IgG1 antibody.
26. The antibody of any one of embodiments 1 to 24, which is a Fab fragment.
27. The antibody of any of embodiments 1 to 26, wherein the antibody binds to VEGF with an affinity of ≤150 pM as measured by surface plasmon resonance at a temperature of 25° C.
28. The antibody of any of embodiments 1 to 27, wherein the antibody is a multispecific antibody.
29. The antibody of any of embodiments 1 to 28 comprising
    (a) a heavy chain of an amino acid sequence selected from the group of SEQ ID NO:13, SEQ ID NO: 15, SEQ ID NO:16, SEQ ID NO:32, SEQ ID NO: 41 and SEQ ID NO: 43; and
    (b) a light chain of SEQ ID NO: 14.
30. The antibody of any of embodiments 1 to 28 comprising a heavy chain of SEQ ID NO:13 and a light chain of SEQ ID NO:14.
31. The antibody of any of embodiments 1 to 28 comprising a heavy chain of SEQ ID NO:15 and a light chain of SEQ ID NO:14.
32. The antibody of any of embodiments 1 to 28 comprising a heavy chain of SEQ ID NO:16 and a light chain of SEQ ID NO:14.
33. The antibody of any of embodiments 1 to 28 comprising a heavy chain of SEQ ID NO:32 and a light chain of SEQ ID NO:14.
34. The antibody of any of embodiments 1 to 28, comprising (a) a VH domain comprising (i) CDR-H1 comprising the amino acid sequence of SEQ ID NO:03; (ii) CDR-H2 having at least 80% sequence identity to the amino acid sequence of SEQ ID NO:04; and (iii) CDR-H3 comprising the amino acid sequence of SEQ ID NO:05; and (b) a VL domain comprising (i) CDR-L1 comprising the amino acid sequence of SEQ ID NO:06; (ii) CDR-L2 comprising the amino acid sequence of SEQ ID NO:07; and (iii) CDR-L3 comprising the amino acid sequence of SEQ ID NO:08.
35. An antibody that binds to VEGF that is an affinity matured variant of an antibody having a VH sequence of SEQ ID NO: 01 and a VL sequence of SEQ ID NO: 02.
36. An antibody that binds to VEGF that is a variant of an antibody having a VH sequence of SEQ ID NO: 01 and a VL sequence of SEQ ID NO: 02, wherein the antibody significantly inhibits VEGF binding to VEGF receptor VEGF-R2 without significantly inhibiting VEGF binding to VEGF receptor VEGF-R1.
37. An antibody that binds to VEGF that binds to the same epitope as an antibody having a VH sequence of SEQ ID NO: 01 and a VL sequence of SEQ ID NO: 02.
38. The antibody of one of the preceding embodiments, wherein the antibody comprises CDR-H2 comprising the amino acid sequence selected from the group of SEQ ID NO:04, SEQ ID NO:10, and SEQ ID NO: 12.
39. The antibody of one of the preceding embodiments, wherein the antibody comprises H-FR3 comprising the amino acid sequence selected from the group of SEQ ID NO: 46 and SEQ ID NO: 47.
40. An isolated nucleic acid encoding the antibody of any of embodiments 1 to 37.
41. A host cell comprising the nucleic acid of embodiment 36.
42. A method of producing an antibody that binds to VEGF comprising culturing the host cell of embodiment 37 under conditions suitable for the expression of the antibody.
43. The method of embodiment 38, further comprising recovering the antibody from the host cell.
44. An antibody produced by the method of embodiment 38 or 39.
45. A pharmaceutical composition comprising the antibody of any of embodiments 1 to 35 and a pharmaceutically acceptable carrier.
46. The antibody of any one of embodiments 1 to 35 or the pharmaceutical composition of embodiment 41 for use as a medicament.
47. The antibody of any one of embodiments 1 to 35 or the pharmaceutical composition of any of embodiment 41 for use in treating a VEGF-related disease.
48. The antibody of any one of embodiments 1 to 35 or the pharmaceutical composition of any of embodiment 41 for use in treating cancer.
49. The antibody of any one of embodiments 1 to 35 or the pharmaceutical composition of any of embodiment 41 for use in treating an eye disease.
50. Use of the antibody of any one of embodiments 1 to 35 or the pharmaceutical composition of embodiment 41 in the manufacture of a medicament for treatment of a VEGF-related disease.
51. Use of the antibody of any one of embodiments 1 to 35 or the pharmaceutical composition of embodiment 41 in the manufacture of a medicament for treatment of cancer.
52. Use of the antibody of any one of embodiments 1 to 35 or the pharmaceutical composition of embodiment 41 in the manufacture of a medicament for treatment of an eye disease.
53. Use of the antibody of any one of embodiments 1 to 35 or the pharmaceutical composition of embodiment 41 in the manufacture of a medicament for inhibiting angiogenesis.
54. A method of treating an individual having a VEGF-related disease comprising administering to the individual an effective amount of the antibody of any one of embodiments 1 to 35 or the pharmaceutical composition of embodiment 41.
55. A method of inhibiting angiogenesis in an individual comprising administering to the individual an effective amount of the antibody of any of embodiments 1 to 35 or the pharmaceutical composition of of embodiment 41 to inhibit angiogenesis.

| | DESCRIPTION OF THE AMINO ACID SEQUENCES |
|---|---|
| SEQ ID NO: 1 | VH domain of antibody VEGF-0089<br>EVQLVESGGGLVQPGGSLRLSCAASGFTFTNYAMTWVRQAPG<br>KGLEWVSSIGNGGGIYTYYADSVKGRFTISRDNSKNTLYLQM<br>NSLRAEDTAVYYCAKGDNLFDSWGPGTLVTVSS |
| SEQ ID NO: 2 | VL domain of antibodies VEGF-0089, VEGF-0113, VEGF-0114<br>DIQMTQSPASLSASVGDRVTITCRASQSIYSSLNWYQQKPGK<br>APKLLIYASTLQSGVPSRFSGSASGTDFTLTISSLQPEDVAT<br>YYCQQYQNFPRTFGQGTKLEIK |
| SEQ ID NO: 3 | H-CDR1 of antibodies VEGF-0089, VEGF-0113, VEGF-0114<br>NYAMT |
| SEQ ID NO: 4 | H-CDR2 of antibodies VEGF-0089<br>SIGNGGGIYTYYADSVKG |
| SEQ ID NO: 5 | H-CDR3 of antibodies VEGF-0089, VEGF-0113, VEGF-0114<br>GDNLFDS |
| SEQ ID NO: 6 | L-CDR1 of antibodies VEGF-0089, VEGF-0113, VEGF-0114<br>RASQSIYSSLN |
| SEQ ID NO: 7 | L-CDR2 of antibodies VEGF-0089, VEGF-0113, VEGF-0114<br>ASTLQSGVPSR |
| SEQ ID NO: 8 | L-CDR3 of antibodies VEGF-0089, VEGF-0113, VEGF-0114<br>FPRT |
| SEQ ID NO: 9 | VH domain of antibody VEGF-0113<br>EVQLVESGGGLVQPGGSLRLSCAASGFTFTNYAMTWVRQAPG<br>KGLEWVSSIGNGPGIYTYYADSVKGRFTISRDNSKNTLYLQM<br>NSLRAEDTAVYYCAKGDNLFDSWGPGTLVTVSS |
| SEQ ID NO: 10 | H-CDR2 of antibody VEGF-0113<br>SIGNGPGIYTYYADSVKG |
| SEQ ID NO: 11 | VH domain of antibody VEGF-0114<br>EVQLVESGGGLVQPGGSLRLSCAASGFTFTNYAMTWVRQAPG<br>KGLEWVSSIGSG_GFYTYYADSVKGRFTISRDNSKNTLYLQM<br>NSLRAEDTAVYYCAKGDNLFDSWGPGTLVTVSS |
| SEQ ID NO: 12 | H-CDR2 of antibody VEGF-0114<br>SIGSGG-FYTYYADSVKG |
| SEQ ID NO: 13 | heavy chain of VEGF-0089 Fab fragment |
| SEQ ID NO: 14 | light chain of VEGF-0089, VEGF-0113, VEGF-0114 Fab fragment |
| SEQ ID NO: 15 | heavy chain of VEGF-0113 Fab fragment |
| SEQ ID NO: 16 | heavy chain of VEGF-0114 Fab fragment |
| SEQ ID NO: 17 | heavy chain of 2C3 Fab fragment |
| SEQ ID NO: 18 | light chain of 2C3 Fab fragment |
| SEQ ID NO: 19 | heavy chain of r84 Fab fragment |
| SEQ ID NO: 20 | light chain of r84 Fab fragment |
| SEQ ID NO: 21 | heavy chain of L3H6 Fab fragment |
| SEQ ID NO: 22 | light chain of L3H6 Fab fragment |
| SEQ ID NO: 23 | heavy chain of Lucentis® (ranibizumab) |
| SEQ ID NO: 24 | light chain of Lucentis® (ranibizumab) |
| SEQ ID NO: 25 | heavy chain of 2C3 full length IgG1 antibody |
| SEQ ID NO: 26 | light chain of 2C3 full length IgG1 antibody |
| SEQ ID NO: 27 | heavy chain of r84 full length IgG1 antibody |
| SEQ ID NO: 28 | light chain of r84 full length IgG1 antibody |
| SEQ ID NO: 29 | human VEGF |

DESCRIPTION OF THE AMINO ACID SEQUENCES

SEQ ID NO: 30  anti-VEGF antibody H-CDR2 consensus sequence I

SEQ ID NO: 31  anti-VEGF antibody H-CDR2 consensus sequence II

SEQ ID NO: 32  heavy chain of VEGF-P1AD8675 Fab fragment

SEQ ID NO: 33  VH domain of antibody VEGF-P1AD8675

SEQ ID NO: 34  heavy chain of HF2-1 Fab fragment

SEQ ID NO: 35  light chain of HF2-1 and HF2-5 Fab fragment

SEQ ID NO: 36  heavy chain of HF2-5 Fab fragment

SEQ ID NO: 37  heavy chain of HF2-9 Fab fragment

SEQ ID NO: 38  light chain of HF2-9 Fab fragment

SEQ ID NO: 39  heavy chain of HF2-11 Fab fragment

SEQ ID NO: 40  light chain of HF2-11 Fab fragment

SEQ ID NO: 41  heavy chain of VEGF-P1AE3520 Fab fragment
EVQLVESGGGLVQPGGSLRLSCAASGFTFTNYAMTWVRQAPG
KGLEWVSSIGNGPGIYTYYADSVKGRFTISRDNWKNTLYLQM
NSLRAEDTAVYYCAKGDNLFDSWGPGTLVTVSSGQPKAPSVF
PLAPCCGDTPSSTVTLGCLVKGYLPEPVTVTWNSGTLTNGVR
TFPSVRQSSGLYSLSSVVSVTSSSQPVTCNVAHPATNTKVDK
TVAPSTCSEQKLISEEDLGAAEPEA SEQ ID NO: 42  VH domain of antibody VEGF-P1AE3520
EVQLVESGGGLVQPGGSLRLSCAASGFTFTNYAMTWVRQAPG
KGLEWVSSIGNGPGIYTYYADSVKGRFTISRDNWKNTLYLQM
NSLRAEDTAVYYCAKGDNLFDSWGPGTLVTVSS SEQ ID NO: 43  heavy chain of VEGF-P1AE3521 Fab fragment
EVQLVESGGGLVQPGGSLRLSCAASGFTFTNYAMTWVRQAPG
KGLEWVSSIGSGGFYTYYADSVKGRFTISRDNWKNTLYLQMN
SLRAEDTAVYYCAKGDNLFDSWGPGTLVTVSSGQPKAPSVFP
LAPCCGDTPSSTVTLGCLVKGYLPEPVTVTWNSGTLTNGVRT
FPSVRQSSGLYSLSSVVSVTSSSQPVTCNVAHPATNTKVDKT
VAPSTCSEQKLISEEDLGAAEPEA SEQ ID NO: 44  VH domain of antibody VEGF-P1AE3521
EVQLVESGGGLVQPGGSLRLSCAASGFTFTNYAMTWVRQAPG
KGLEWVSSIGSGGFYTYYADSVKGRFTISRDNWKNTLYLQMN
SLRAEDTAVYYCAKGDNLFDSWGPGTLVTVSS SEQ ID NO: 45  Human VEGF-A121
APMAEGGGQNHHEVVKFMDVYQRSYCHPIETLVDIFQEYPDE
IEYIFKPSCVPLMRCGGCCNDEGLECVPTEESNITMQIMRIK
PHQGQHIGEMSFLQHNKCECRPKKDRARQEKCDKPRR SEQ ID NO: 46  H-FR3 of VEGF-0089, VEGF-0113, VEGF-0114
FTISRDNSKNTLYLQMNSLRAEDTAVYYCAK SEQ ID NO: 47  H-FR3 of VEGF-P1AD8675
FTISRDNWKNTLYLQMNSLRAEDTAVYYCAK In the following the amino acid sequences of the VH und VL domains including marked HVRs (HVRs in bold, underlined letters) of anti-VEGF antibodies VEGF-0089, VEGF-0113, and VEGF-0114 are listed:

antibody VEGF-0089:
VH domain
(SEQ ID NO: 01)
EVQLVESGGGLVQPGGSLRLSCASGFTFTNYAMTWVRQAPGKGLEWVSS

IGNGGGIYTYYADSVKGRFTISRDNSKNTLYLQMNSLRAEDTAVYYCAKG

DNLFDSWGPGTLVTVSS

VL domain
(SEQ ID NO: 02)
DIQMTQSPASLSASVGDRVTITCRASQSIYSSLNWYQQKPGKAPKLLIYA

STLQSGVPSRFSGSASGTDFTLTISSLQPEDVATYYCQQYQNFPRTFGQG

TKLEIK antibody VEGF-0113:
VH domain
(SEQ ID NO: 09)
EVQLVESGGGLVQPGGSLRLSCASGFTFTNYAMTWVRQAPGKGLEWVSS

-continued
```
IGNGPGIYTYYADSVKGRFTISRDNSKNTLYLQMNSLRAEDTAVYYCAKG

DNLFDSWGPGTLVTVSS

VL domain
                                             (SEQ ID NO: 02)
DIQMTQSPASLSASVGDRVTITCRASQSIYSSLNWYQQKPGKAPKLLIYA

STLQSGVPSRFSGSASGTDFTLTISSLQPEDVATYYCQQYQNFPRTFGQG

TKLEIK antibody VEGF-0114:
VH domain
                                             (SEQ ID NO: 11)
EVQLVESGGGLVQPGGSLRLSCASGFTFTNYAMTWVRQAPGKGLEWVSS

IGSG GFYTYYADSVKGRFTISRDNSKNTLYLQMNSLRAEDTAVYYCAKG

DNLFDSWGPGTLVTVSS

VL domain
                                             (SEQ ID NO: 02)
DIQMTQSPASLSASVGDRVTITCRASQSIYSSLNWYQQKPGKAPKLLIYA

STLQSGVPSRFSGSASGTDFTLTISSLQPEDVATYYCQQYQNFPRTFGQG

TKLEIK antibody VEGF-P1AD8675:
VH domain
                                             (SEQ ID NO: 33)
EVQLVESGGGLVQPGGSLRLSCASGFTFTNYAMTWVRQAPGKGLEWVSS

IGNGGGIYTYYADSVKGRFTISRDNWKNTLYLQMNSLRAEDTAVYYCAKG

DNLFDSWGPGTLVTVSS

VL domain
                                             (SEQ ID NO: 02)
DIQMTQSPASLSASVGDRVTITCRASQSIYSSLNWYQQKPGKAPKLLIYA

STLQSGVPSRFSGSASGTDFTLTISSLQPEDVATYYCQQYQNFPRTFGQG

TKLEIK antibody VEGF-P1AE3520:
VH domain
                                             (SEQ ID NO: 42)
EVQLVESGGGLVQPGGSLRLSCASGFTFTNYAMTWVRQAPGKGLEWVSS

IGNGPGIYTYYADSVKGRFTISRDNWKNTLYLQMNSLRAEDTAVYYCAKG

DNLFDSWGPGTLVTVSS

VL domain
                                             (SEQ ID NO: 02)
DIQMTQSPASLSASVGDRVTITCRASQSIYSSLNWYQQKPGKAPKLLIYA

STLQSGVPSRFSGSASGTDFTLTISSLQPEDVATYYCQQYQNFPRTFGQG

TKLEIK antibody VEGF- P1AE3521:
VH domain
                                             (SEQ ID NO: 44)
EVQLVESGGGLVQPGGSLRLSCAASGFTFTNYAMTWVRQAPGKGLEWVSS

IGSG GFYTYYADSVKGRFTISRDNWKNTLYLQMNSLRAEDTAVYYCAKG

DNLFDSWGPGTLVTVSS

VL domain
                                             (SEQ ID NO: 02)
DIQMTQSPASLSASVGDRVTITCRASQSIYSSLNWYQQKPGKAPKLLIYA

STLQSGVPSRFSGSASGTDFTLTISSLQPEDVATYYCQQYQNFPRTFGQG

TKLEIK
```

EXAMPLES

The following are examples of methods and compositions of the invention. It is understood that various other embodiments may be practiced, given the general description provided above.

Example 1

Generation of Human Anti-VEGF Antibody (Antibody VEGF-0089)

An overlay of the crystal structures of a human VEGF-dimer in complex with VEGF-R1 domain 2 and VEGF-R3 domains 2 and 3 is depicted in FIG. 1. This superimposition illustrates that both VEGF receptors bind to a highly similar region on the VEGF dimer and that it therefore appears highly challenging to generate antibodies that bind to VEGF that do not inhibit VEGF-binding to both receptors, VEGF-R1 and VEGF-R2, in the same fashion. In line with this, among the plurality of anti-VEGF antibodies known in the art, only a few antibodies were reported to selectively block VEGF-binding to VEGF-R2 rather than VEGF-binding to VEGF-R1.

Antibody VEGF-0089 as described herein was derived from Roche proprietary transgenic rabbits, expressing a humanized antibody repertoire, upon immunization with a VEGF-derived antigen. Transgenic rabbits comprising a human immunoglobulin locus are reported in WO 2000/46251, WO 2002/12437, WO 2005/007696, WO 2006/047367, US 2007/0033661, and WO 2008/027986. The animals were housed according to the Appendix A "Guidelines for accommodation and care of animals" in an AAALAC-accredited animal facility. All animal immunization protocols and experiments were approved by the Government of Upper Bavaria (permit number 55.2-1-54-2532-90-14) and performed according to the German Animal Welfare Act and the Directive 2010/63 of the European Parliament and Council.

Immunization of Transgenic Rabbits

Briefly, rabbits (n=3), 12-16 week old, were immunized with recombinant human VEGF-121 protein coupled to keyhole limpet hemocyanin (KLH) (produced in house). All animals were immunized with 400 μg protein, emulsified with complete Freund's adjuvant (CFA), at day 0 by intradermal application, followed by 200 ug protein emulsion at weeks 1, 2, 6, 11 and 14, by alternating intramuscular and subcutaneous injections. Blood was taken at days 4, 5 and 6 post immunizations, starting from the 4th immunization onwards. Serum was prepared for immunogen-specific rabbit-, and human-specific immunoglobulin titer determination by ELISA, and peripheral mononuclear cells were isolated, which were used as a source of antigen-specific B cells in the B cell cloning process.

B Cell Cloning from Transgenic Rabbits

Isolation of rabbit peripheral blood mononuclear cells (PBMC): Blood samples were taken of immunized rabbits. EDTA containing whole blood was diluted twofold with 1×PBS (PAA) before density centrifugation using lymphocyte mammal (Cedarlane Laboratories) according to the specifications of the manufacturer. The PBMCs were washed twice with 1×PBS.

EL-4 B5 medium: RPMI 1640 (Pan Biotech) supplemented with 10% FCS (Pan Biotech), 2 mM Glutamin, 1% penicillin/streptomycin solution (Gibco), 2 mM sodium pyruvate, 10 mM HEPES (PAN Biotech) and 0.05 mM b-mercaptoethanole (Invitrogen) was used.

Coating of plates: Sterile cell culture 6-well plates were coated with 2 µg/ml KLH in carbonate buffer (0.1 M sodium bicarbonate, 34 mM Disodiumhydrogencarbonate, pH 9.55) over night at 4° C. Plates were washed in sterile PBS three times before use.

Depletion of macrophages/monocytes or of human Fc binders: The PBMCs were seeded on sterile 6-well plates (cell culture grade) to deplete macrophages and monocytes through unspecific adhesion. Each well was filled at maximum with 4 ml medium and up to 6×10e6 PBMCs from the immunized rabbit and were allowed to bind for 1 h at 37° C. in the incubator. The cells in the supernatant (peripheral blood lymphocytes (PBLs)) were used for the antigen panning step.

Immune fluorescence staining and Flow Cytometry: The anti-IgG FITC (AbD Serotec) and the anti-huCk PE (Dianova) antibody was used for single cell sorting. For surface staining, cells from the depletion and enrichment step were incubated with the anti-IgG FITC and the anti-huCk PE antibody in PBS and incubated for 45 min in the dark at 4° C. After staining the PBMCs were washed two fold with ice cold PBS. Finally the PBMCs were resuspended in ice cold PBS and immediately subjected to the FACS analyses. Propidium iodide in a concentration of 5 µg/ml (BD Pharmingen) was added prior to the FACS analyses to discriminate between dead and live cells. A Becton Dickinson FACSAria™ equipped with a computer and the FACSDiva™ software (BD Biosciences) were used for single cell sort.

B-cell cultivation: The cultivation of the rabbit B cells was performed by a method described by Seeber et al. (S Seeber et al. PLoS One 9 (2), e86184. 2014 Feb. 4). Briefly, single sorted rabbit B cells were incubated in 96-well plates with 200 l/well EL-4 B5 medium containing Pansorbin® Cells (1:100000) (Calbiochem), 5% rabbit thymocyte supernatant (MicroCoat) and gamma-irradiated murine EL-4 B5 thymoma cells (5×10e5 cells/well) for 7 days at 37° C. in the incubator. The supernatants of the B-cell cultivation were removed for screening and the remaining cells were harvested immediately and were frozen at −80° C. in 100 µl RLT buffer (Qiagen).

RNA encoding the V domains of the antibodies was isolated. For recombinant expression of the antibody PCR-products coding for VH or VL were cloned as cDNA into expression vectors and transiently transformed into HEK-293 cells.

From the screening an antibody comprising a VH domain of SEQ ID NO:01 and a VL domain of SEQ ID NO:02 was selected. This antibody is herein also referred to as antibody "VEGF-0089". For the subsequent analyses the antibody VEGF-0089 was generated as a Fab fragment (herein referred to as "VEGF-0089 Fab fragment" or simply "VEGF-0089 Fab") having the human VH and VL domains and rabbit derived constant domains of the light chain (CLkappa) and heavy chain (CH1). The amino acid sequence of the heavy chain of VEGF-0089 Fab fragment is SEQ ID NO:13. The amino acid sequence of the light chain of VEGF-0089 Fab fragment is SEQ ID NO:14.

Example 2

Characterisation of Generated Human Anti-VEGF Antibody (Antibody VEGF-0089)

VEGF-binding of antibody VEGF-0089 Fab fragment was assessed by surface plasmon resonance (SPR) as described below.

Determination of Antibody Binding Affinity by Surface Plasmon Resonance (SPR)

An anti-His capturing antibody (GE Healthcare 28995056) was immobilized to a Series S Sensor Chip C1 (GE Healthcare 29104990) using standard amine coupling chemistry resulting in a surface density of 500-1000 resonance units (RU). As running and dilution buffer, HBS-P+ (10 mM HEPES, 150 mM NaCl pH 7.4, 0.05% Surfactant P20) was used, the measurement temperature was set to 25° C. and 37° C., respectively. hVEGF-A121 was captured to the surface with resulting capture levels ranging from 5 to 35 RU. Dilution series of anti-VEGF antibodies (0.37-30 nM) were injected for 120 s, dissociation was monitored for at least 600 s at a flow rate of 30 µl/min. The surface was regenerated by injecting 10 mM Glycine pH 1.5 for 60 s. Bulk refractive index differences were corrected by subtracting blank injections and by subtracting the response obtained from the control flow cell without captured hVEGF-A121. Rate constants were calculated using the Langmuir 1:1 binding model within the Biacore® Evaluation software.

As a result, the KD of the VEGF-0089 Fab fragment was determined to be 134 pM (at a temperature of 25° C.).

For further characterization of the antibody, inhibition of VEGF-binding to its receptors VEGF-R1 and VEGF-R2 in presence of VEGF-0089 Fab fragment was assessed as described below:

Inhibition of VEGF-Binding to VEGF-RJ and VEGF-R2 in Presence of Antibody Fab Fragments (VEGF:VEGF-R2/R1 Inhibition ELISA)

384 well streptavidin plates (Nunc/Microcoat #11974998001) were coated with 0.25 µg/ml biotinylated VEGF-R1 or 0.5 µg/ml biotinylated VEGF-R2 (inhouse production, each 25 µl/well in DPBS (1×) (PAN, #P04-36500)). Plates were incubated for 1 h at room temperature. In parallel, VEGF-121-His (inhouse production) at a concentration of 0.7 nM was incubated with antibodies in different dilutions (12×1:2 dilution steps, starting with a concentration of 500 nM). This pre-incubation step was carried out in 384 well PP plates (Weidmann medical technology, #23490-101) in 1×OSEP buffer (bidest water, 10×, Roche, #11 666 789 001+0.5% Bovine Serum Albumin Fraction V, fatty acid free, Roche, #10 735 086 001+0.05% Tween 20). Plates were incubated for 1 h at room temperature. After washing VEGF-R1/VEGF-R2 coated streptavidin plates 3 times with 90 µl/well PBST-buffer (bidest water, 10×PBS Roche #11666789001+0.1% Tween 20), 25 µl of samples from the VEGF-antibody pre-incubation plate were transferred to coated strepavidin plates which were subsequently incubated for 1 h at room temperature. After washing 3 times with 90 µl/well PBST-buffer, 25 µl/well detection antibody (anti His POD, Bethyl, #A190-114P, 1:12000) in 1×OSEP was added. After incubation for 1 h at room temperature plates were washed 3 times with 90 µl PBST-buffer. 25 µl TMB (Roche, #11 835 033 001) was added to all wells simultaneously. After 10 min incubation at room temperature, signals were detected at 370 nm/492 nm on a Tecan Safire 2 Reader.

Figure 2:
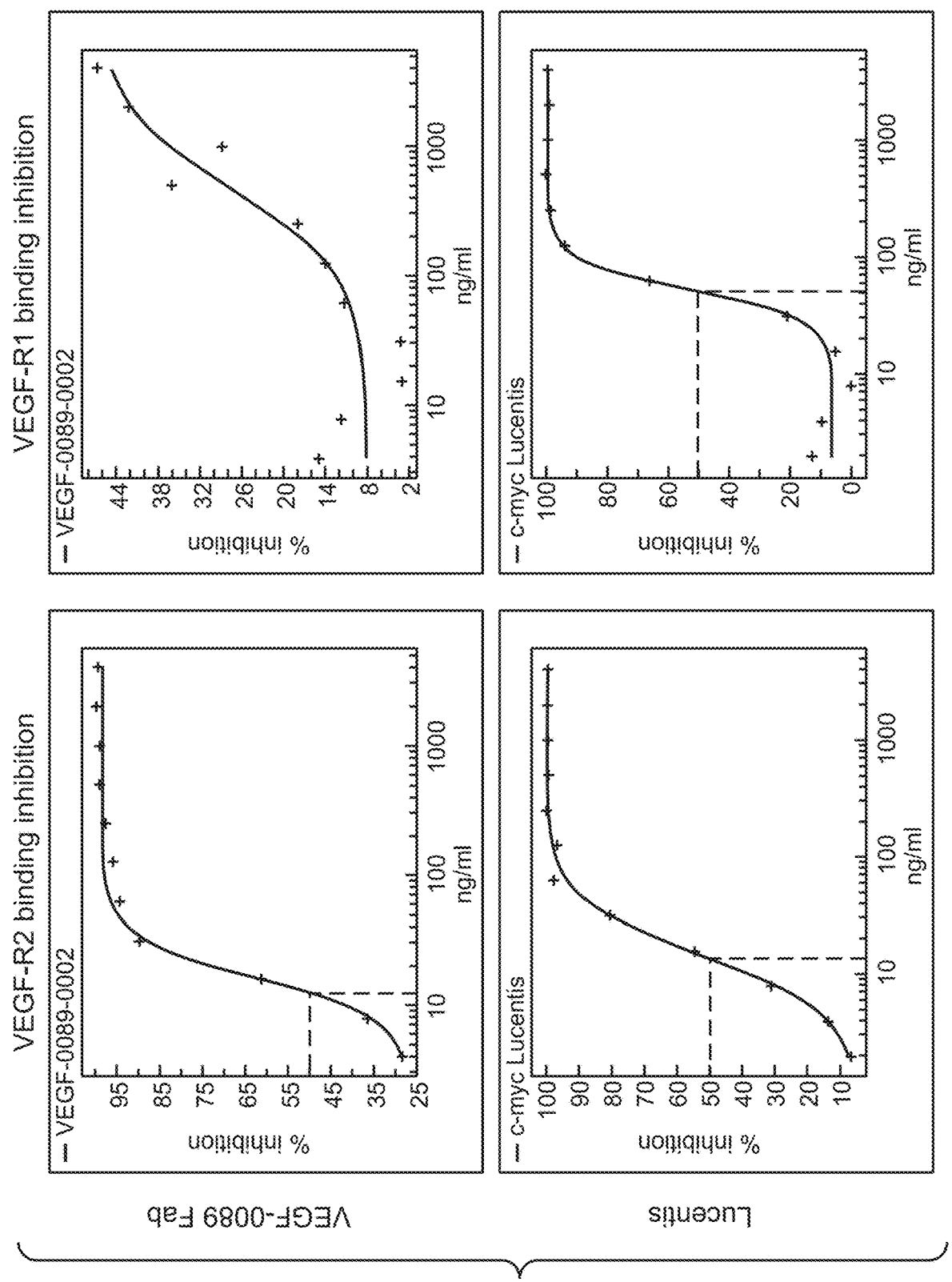
FIG. 2: Inhibition of VEGF-binding to VEGF-R1 and VEGF-R2 in presence of antibody Fab fragments (VEGF: VEGF-R2/R1 inhibition ELISA) as described in Example 2.

As a control and representative for a prior art anti-VEGF antibody that is used in the clinic, Lucentis® (ranibizumab, heavy chain amino acid sequence of SEQ ID NO:23, light chain amino acid sequence of SEQ ID NO:24) was assessed under the same conditions. The results are shown in FIG. 2.

The results indicate that VEGF-0089 Fab fragment is capable of fully blocking VEGF-binding to VEGF-R2. VEGF-0089 Fab fragment did not fully block VEGF-binding to VEGF-R1. Consequently, VEGF-0089 Fab fragment is considered to selectively block VEGF-signalling through VEGF-R2 but not through VEGF-R1. As illustrated in FIG. 2, prior art antibody Lucentis® is capable of fully blocking VEGF-binding to both receptors, VEGF-R2 and VEGF-R1.

Example 3

Improvement of Human Anti-VEGF Antibody VEGF-0089

Antibody variants of antibody VEGF-0089 were generated in order to further improve the characteristics of the antibody.

From various antibody candidates, two antibodies were selected, wherein in the H-CDR2 loop the glycin in the middle of the triglycine stretch within the H-CDR2 loop was substituted or deleted.

VEGF-0113 Antibody

A first variant of the VEGF-0089 antibody is the antibody comprising a heavy chain variable domain of SEQ ID NO:09 and a light chain variable domain of SEQ ID NO:02. This antibody is herein referred to as "VEGF-0113" antibody, and—when provided as a Fab fragment with rabbit derived CLkappa and CH1 domains—as "VEGF-0113 Fab fragment" or simply "VEGF-0113 Fab". The VEGF-0113 Fab fragment as used herein comprises a heavy chain of SEQ ID NO:15 and a light chain of SEQ ID NO:14. The VEGF-0113 antibody differs from antibody VEGF-0089 only in the amino acid sequence of H-CDR2, as the glycine residue at position 6 of H-CDR2 of the VEGF-0089 antibody is substituted by a proline residue:

```
                              (SEQ ID NO: 04)
H-CDR2 of VEGF-0089   SIGNGGGIYTYYADSVKG (SEQ ID NO: 10)
H-CDR2 of VEGF-0113   SIGNGPGIYTYYADSVKG
```

The amino acid motif "GPG" that is realized in H-CDR2 of VEGF-0113 confers much less conformational freedom to the H-CDR2 loop when compared to the triglycine stretch "GGG" in the H-CDR2 of VEGF-0089.

VEGF-0114 Antibody

A second variant of the VEGF-0089 antibody is the antibody comprising a heavy chain variable domain of SEQ ID NO:11 and a light chain variable domain of SEQ ID NO:02. This antibody is herein referred to as "VEGF-0114" antibody, and—when provided as a Fab fragment with rabbit derived CLkappa and CH1 domains—as "VEGF-0114 Fab fragment" or simply "VEGF-0114 Fab". The VEGF-0114 Fab fragment as used herein comprises a heavy chain of SEQ ID NO:16 and a light chain of SEQ ID NO:14. The VEGF-0114 antibody differs from antibody VEGF-0089 only in the amino acid sequence of H-CDR2, as the asparagine residue at position 4 of H-CDR2 of the VEGF-0089 antibody is substituted by a serine residue, the glycine residue at position 7 of H-CDR2 of the VEGF-0089 antibody was removed and the isoleucine residue at position 8 was replaced by a phenylalanine residue:

```
                              (SEQ ID NO: 04)
H-CDR2 of VEGF-0089   SIGNGGGIYTYYADSVKG (SEQ ID NO: 12)
H-CDR2 of VEGF-0114   SIGSGG-FYTYYADSVKG
```

To generate antibody VEGF-0114 the third glycine residue in triglycine stretch "GGG" in the H-CDR2 of VEGF-0089 was removed. In addition, a phenylalanine was introduced replacing the isolycine residue following the triglycine stretch.

Example 4

VEGF-Binding of Anti-VEGF Antibodies as Assessed by Direct ELISA

Binding of prior art antibodies 2C3 and r84 to VEGF as assessed via a direct ELISA as follows:

VEGF Binding ELISA

Nunc® MaxiSorp™ 384 well clear plates (#464718) were coated with 1 µg/ml VEGF-121-His (inhouse production) and incubated 1 h at room temperature. After washing 3 times with 90 µl/well PBST-buffer (bidest water, 10×PBS Roche #11666789001+0.1% Tween® 20) blocking buffer (bidest water, 10×PBS Roche #11666789001+2% Bovine Serum Albumin Fraction V, fatty acid free, Roche, #10735078001+0.05% Tween® 20) was added 90 µl/well and incubated for 1 h at room temperature. After washing 3 times with 90 µl/well PBST-buffer 25 µl of an antibody dilution series (16×1:2 dilution steps) starting with a concentration of 60 nM was added to VEGF-coated wells. After incubation for 1 h at room temperature, plates were again washed 3 times with 90 µl/well PBST-buffer. 25 µl/well detection antibody (anti c-myc POD (Bethyl, #A190-104P, 1:16000) or anti hu lambda LC (Bethyl, #A80-116P, 1:15000) or F(ab')2 Fragment goat anti hu IgG Fcy Fragment specific (JIR, #109-036-098, 1:2000) or goat anti hu Ig kappa LC (Millipore, #AP502P, 1:2000) in 1×PBS (10×, Roche, #11 666 789 001)+0.5% Bovine Serum Albumin Fraction V, fatty acid free, Roche, #10 735 086 001+0.05% Tween 20) was added and plates were incubated for 1 h at room temperature. After washing 3 times with 90 µl PBST-buffer, 25 µl TMB (Roche, #11 835 033 001) was added to each well. After 3 min incubation at RT, signals were detected at 370 nm/492 nm on a Tecan Safire 2 Reader.

Fab fragments of the antibodies of the invention were tested, respectively. The following antibodies were tested (see table 1):

TABLE 1

| Amino acid sequences of antibodies of the invention | | |
|---|---|---|
| | heavy chain | light chain |
| VEGF-0089 Fab | SEQ ID NO: 13 | SEQ ID NO: 14 |
| VEGF-0113 Fab | SEQ ID NO: 15 | SEQ ID NO: 14 |
| VEGF-0114 Fab | SEQ ID NO: 16 | SEQ ID NO: 14 |

Prior art antibodies were generated using the same methods as described in Example 1 (transient transformation of HEK-293 cells). The following prior art antibody Fab fragments were analysed in parallel: Ranibizumab (Lucentis®), Fab fragments of the prior art antibodies 2C3 (disclosed in WO200064946), r84 (disclosed in WO 2009060198) and L3H6 (disclosed in WO 2012089176). In addition, antibodies 2C3 and r84 analysed as full length IgG1 antibodies.

Amino acid sequences of the prior art antibodies used are listed in table 2.

TABLE 2

| Amino acid sequences of prior art antibodies: | | |
|---|---|---|
| | heavy chain | light chain |
| 2C3 Fab | SEQ ID NO: 17 | SEQ ID NO: 18 |
| r84 Fab | SEQ ID NO: 19 | SEQ ID NO: 20 |
| 2C3 IgG1 | SEQ ID NO: 25 | SEQ ID NO: 26 |
| r84 IgG1 | SEQ ID NO: 27 | SEQ ID NO: 28 |
| L3H6 Fab | SEQ ID NO: 21 | SEQ ID NO: 22 |
| Ranibizumab | SEQ ID NO: 23 | SEQ ID NO: 24 |

Figure 3:
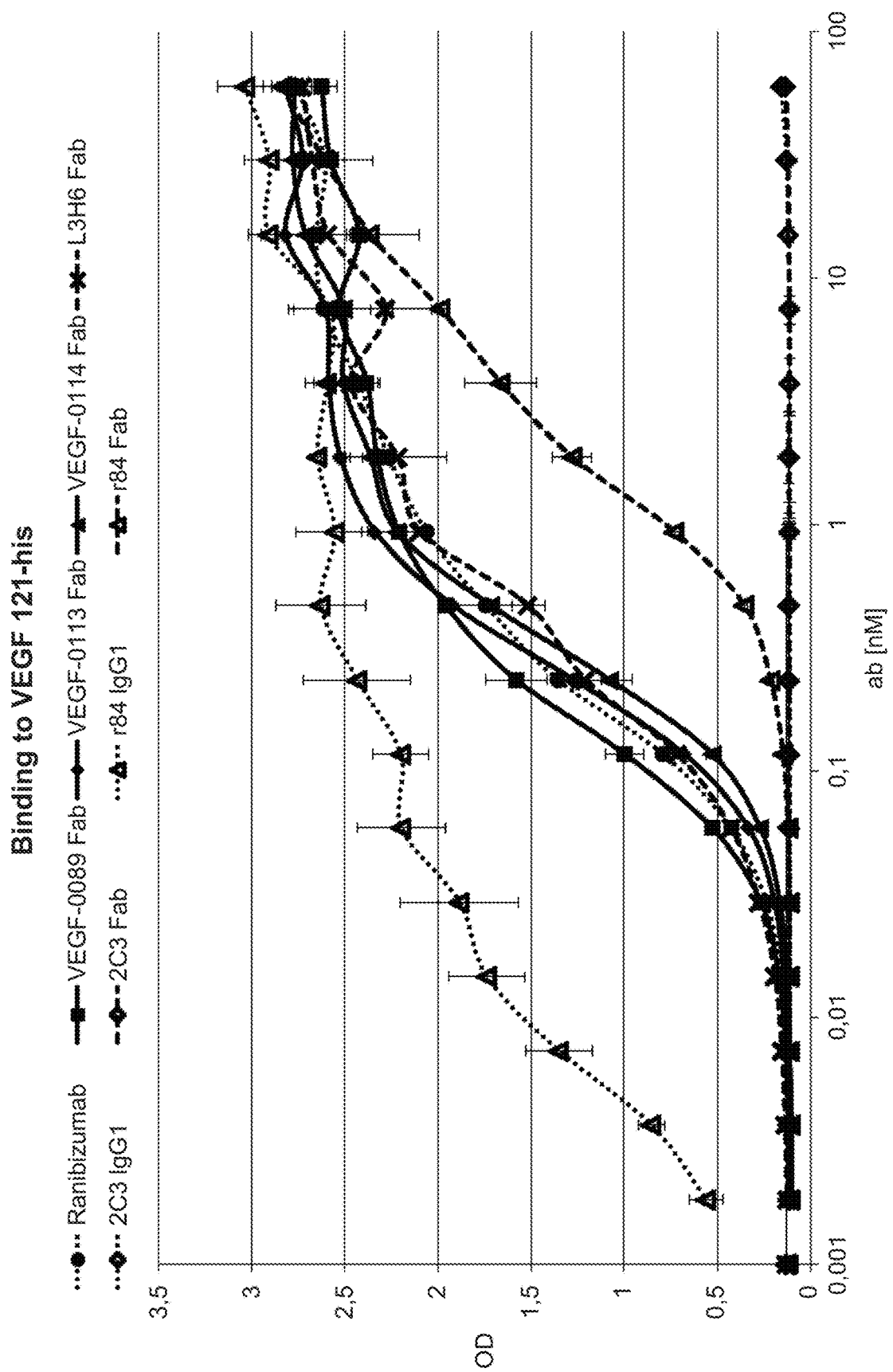
FIG. 3: VEGF binding of anti-VEGF antibodies determined by ELISA as described in Example 4.

Results are shown in FIG. 3. While no VEGF-binding could be observed under the assay conditions used for antibody 2C3, VEGF-binding was confirmed for prior art antibodies r84 and L3H6. It is demonstrated that antigen binding by antibody r84 is prominently reduced when used as a Fab fragment rather than full length IgG1 due to lack of avidity. VEGF-binding was confirmed for all tested antibodies of the invention.

Example 5

Binding Affinity of Antibodies of the Invention

The affinity of the antibodies was determined by SPR using the same methods as described in Example 2. All Fab fragments as listed in table 1 and table 2 were tested.

Affinities of the antibodies of the invention as well as of the prior art antibodies were assessed as described above. Results are shown in table 3.

TABLE 3

| Affinities of anti-VEGF antibodies | | |
|---|---|---|
| | KD [pM] at 25° C. | KD [pM] at 37° C. |
| VEGF-0089 Fab | 134 | 99 |
| VEGF-0113 Fab | 21 | 17 |
| VEGF-0114 Fab | 55 | 56 |
| 2C3 Fab | tbd | tbd |
| r84 Fab | tbd | tbd |
| L3H6 Fab | 3356 | 4517 |
| Ranibizumab | 154 +/− 47 | 507 |

Example 6

Inhibition of VEGF-Binding to VEGF-R2 in Presence of Anti-VEGF Antibodies

Binding of VEGF to VEGF-R2 and VEGF-R1, respectively, in presence of antibody Fab fragments of the invention was tested as follows.
Inhibition of VEGF-Binding to VEGF-RJ and VEGF-R2 in Presence of Antibody Fab Fragments (VEGF:VEGF-R2/R1 Inhibition ELISA)
384 well streptavidin plates (Nunc/Microcoat #11974998001) were coated with 0.25 µg/ml biotinylated VEGF-R1 or 0.5 µg/ml biotinylated VEGF-R2 (inhouse production, each 25 µl/well in DPBS (1×) (PAN, #P04-36500)). Plates were incubated for 1 h at room temperature. In parallel, VEGF-121-His (inhouse production) at a concentration of 0.7 nM was incubated with antibodies in different dilutions (12×1:2 dilution steps, starting with a concentration of 500 nM). This pre-incubation step was carried out in 384 well PP plates (Weidmann medical technology, #23490-101) in 1×OSEP buffer (bidest water, 10×, Roche, #11 666 789 001+0.5% Bovine Serum Albumin Fraction V, fatty acid free, Roche, #10 735 086 001+0.05% Tween 20). Plates were incubated for 1 h at room temperature. After washing VEGF-R1/VEGF-R2 coated streptavidin plates 3 times with 90 µl/well PBST-buffer (double-distilled water, 10×PBS Roche #11666789001+0.1% Tween® 20), 25 µl of samples from the VEGF-antibody pre-incubation plate were transferred to coated strepavidin plates which were subsequently incubated for 1 h at room temperature. After washing 3 times with 90 µl/well PBST-buffer, 25 µl/well detection antibody (anti His POD, Bethyl, #A190-114P, 1:12000) in 1×OSEP was added. After incubation for 1 h at room temperature plates were washed 3 times with 90 µl PBST-buffer. 25 µl TMB (Roche, #11 835 033 001) was added to all wells simultaneously. After 10 min incubation at room temperature, signals were detected at 370 nm/492 nm on a Tecan Safire 2 Reader.

Figure 4A:
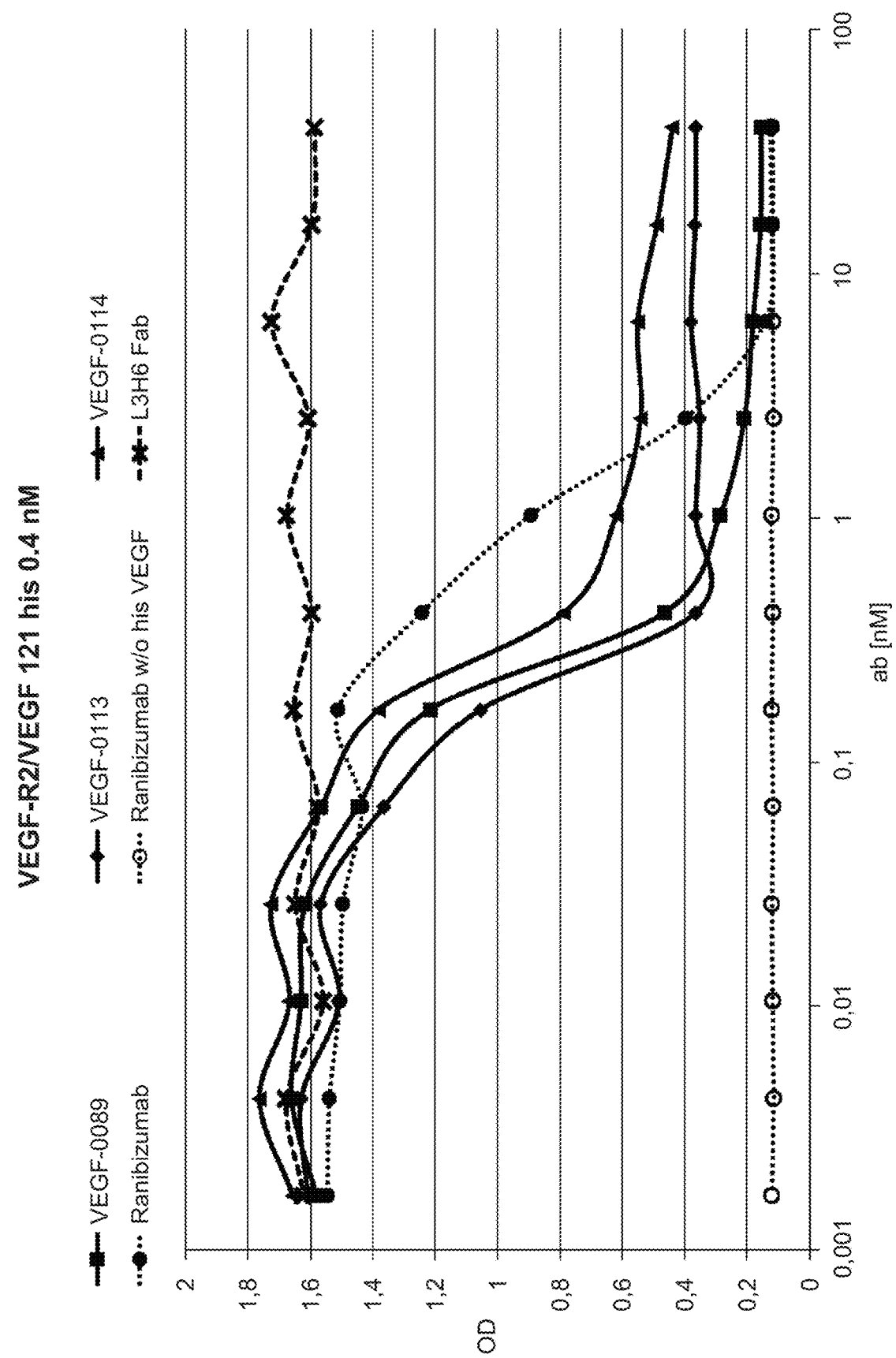
FIG. 4A: Inhibition of VEGF binding to VEGF-R2 in presence of anti-VEGF antibodies VEGF-0089, VEGF-0113, VEGF-0114 of the invention and Ranibizumab and L3H6 Fab as described in Example 6 (0.4 nM VEGF).

In a first experiment, antibodies VEGF-0089, VEGF-0113 and VEGF-0114 of the invention were tested (see table 1) and prior art antibodies L3H6 Fab and Ranibizumab (see table 2) were analyzed in presence of 0.4 nM VEGF. As a negative control Ranibizumab was analyzed in absence of VEGF as well (indicated in the graph as "Ranibizumab w/o VEGF"). Results are shown in FIG. 4A.

Figure 4B:
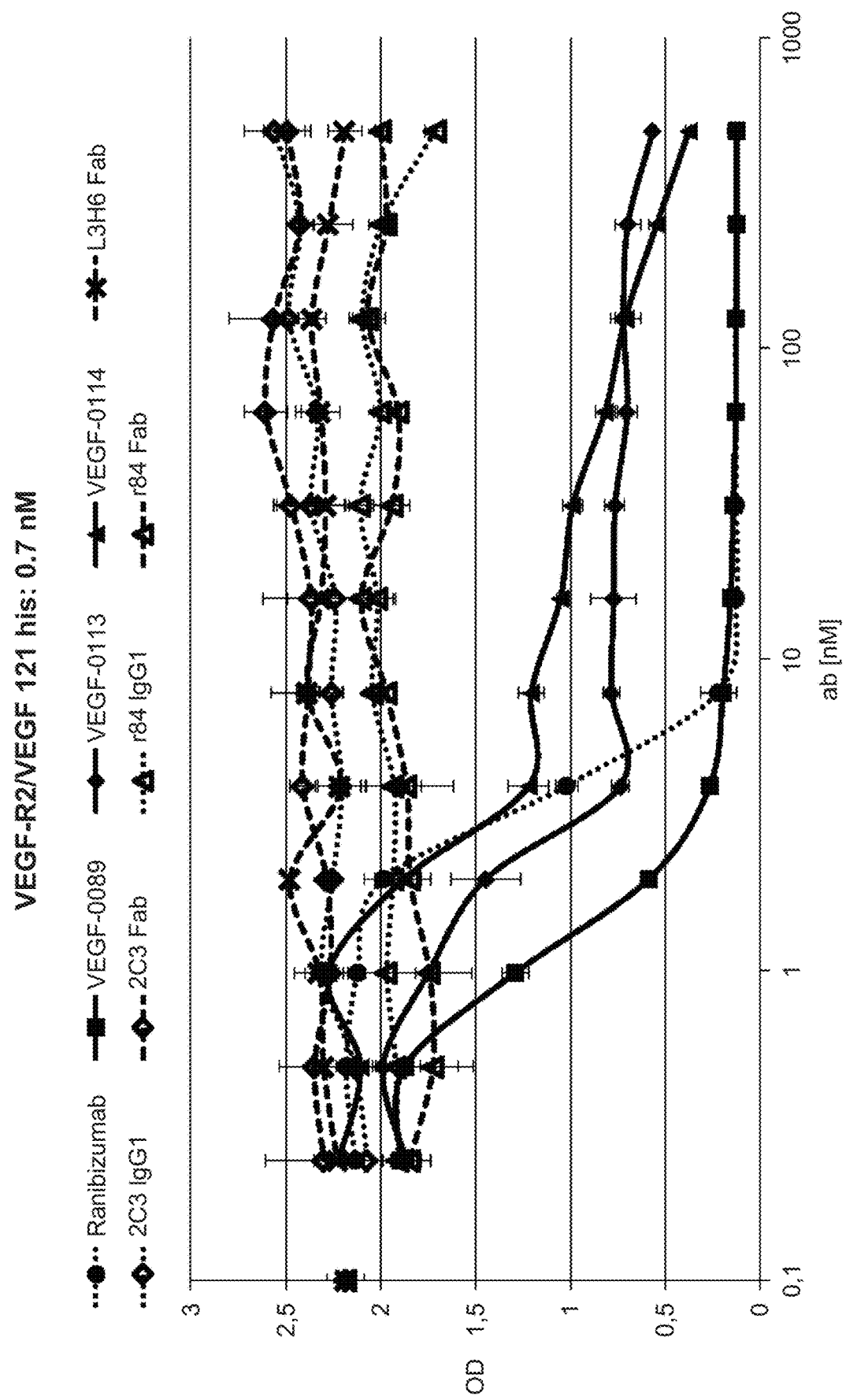
FIG. 4B: Inhibition of VEGF binding to VEGF-R2 in presence of anti-VEGF antibody VEGF-0089 of the invention and prior art antibodies 2C3, r84 and L3H6 as described in Example 6 (0.7 nM VEGF).

In a second experiment, all antibodies listed in table 1 and table 2 were analyzed as described in Example 2 in presence of 0.7 nM VEGF. Results are shown in FIG. 4B.

Figure 7:
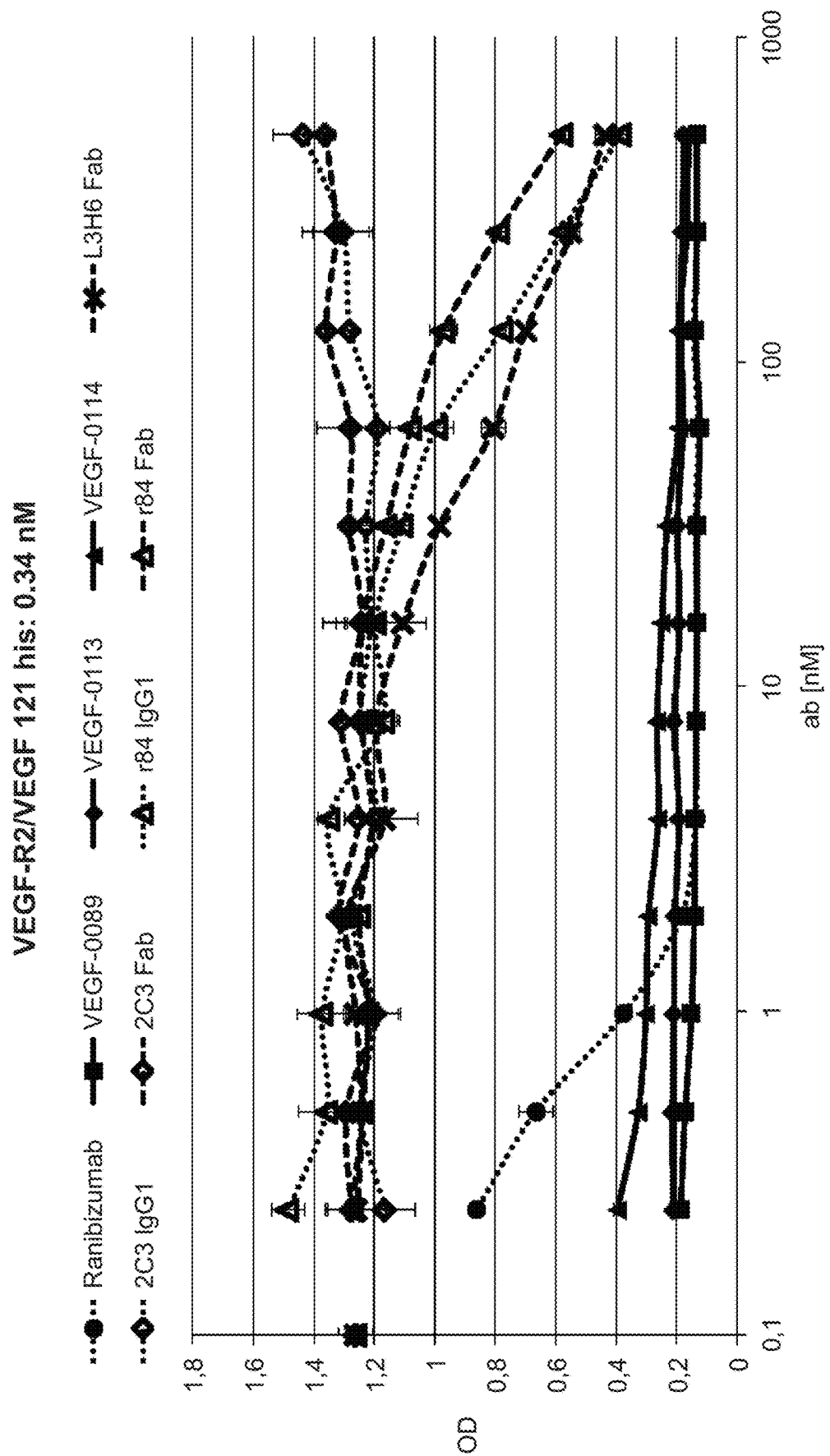
FIG. 7: Inhibition of VEGF binding to VEGF-R2 in presence of anti-VEGF antibodies as described in Example 6 (0.34 nM VEGF).

No inhibition of VEGF-binding to VEGF-R2 was assessed in the experimental setup used for the tested prior art antibodies. The experiment was repeated under the same conditions as described above, however using 0.34 nM VEGF-121-His instead of 0.7 nM. Results are shown in FIG. 7.

In this experimental setup inhibition of VEGF-binding to VEGF-R2 was observed for the prior art antibodies r84 IgG1, r84 Fab and L3H6 Fab at high concentrations. Antibodies VEGF-0089 Fab, VEGF-0113 Fab and VEGR-0114 Fab of the invention inhibited VEGF-binding to VEGF-R2 in all tested concentrations.

Example 7

Inhibition of VEGF Binding to VEGF-R1 in Presence of Anti-VEGF Antibody

Figure 5:
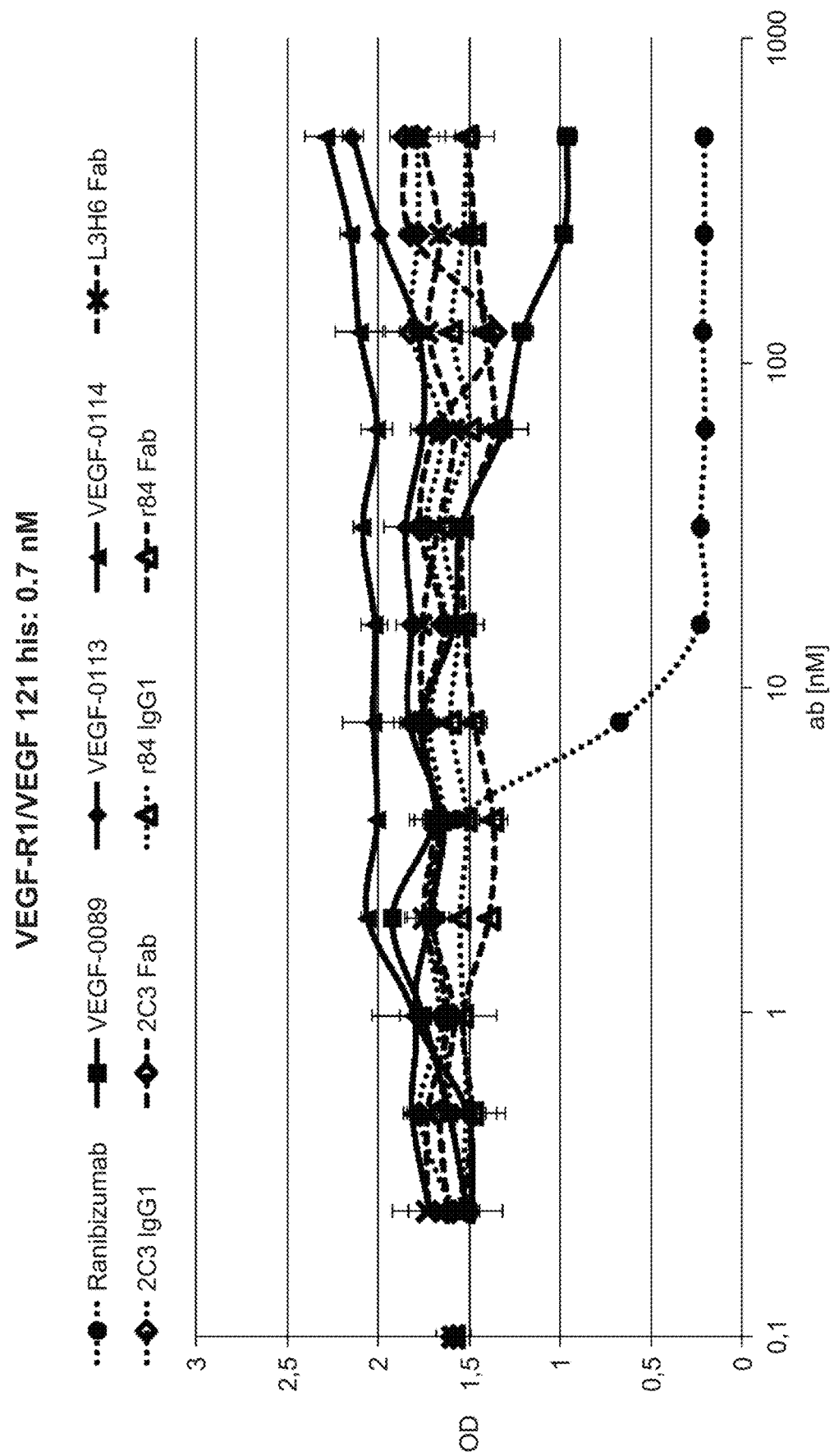
FIG. 5: Inhibition of VEGF binding to VEGF-R1 in presence of anti-VEGF antibodies as described in Example 6 (0.7 nM VEGF).
Figure 6:
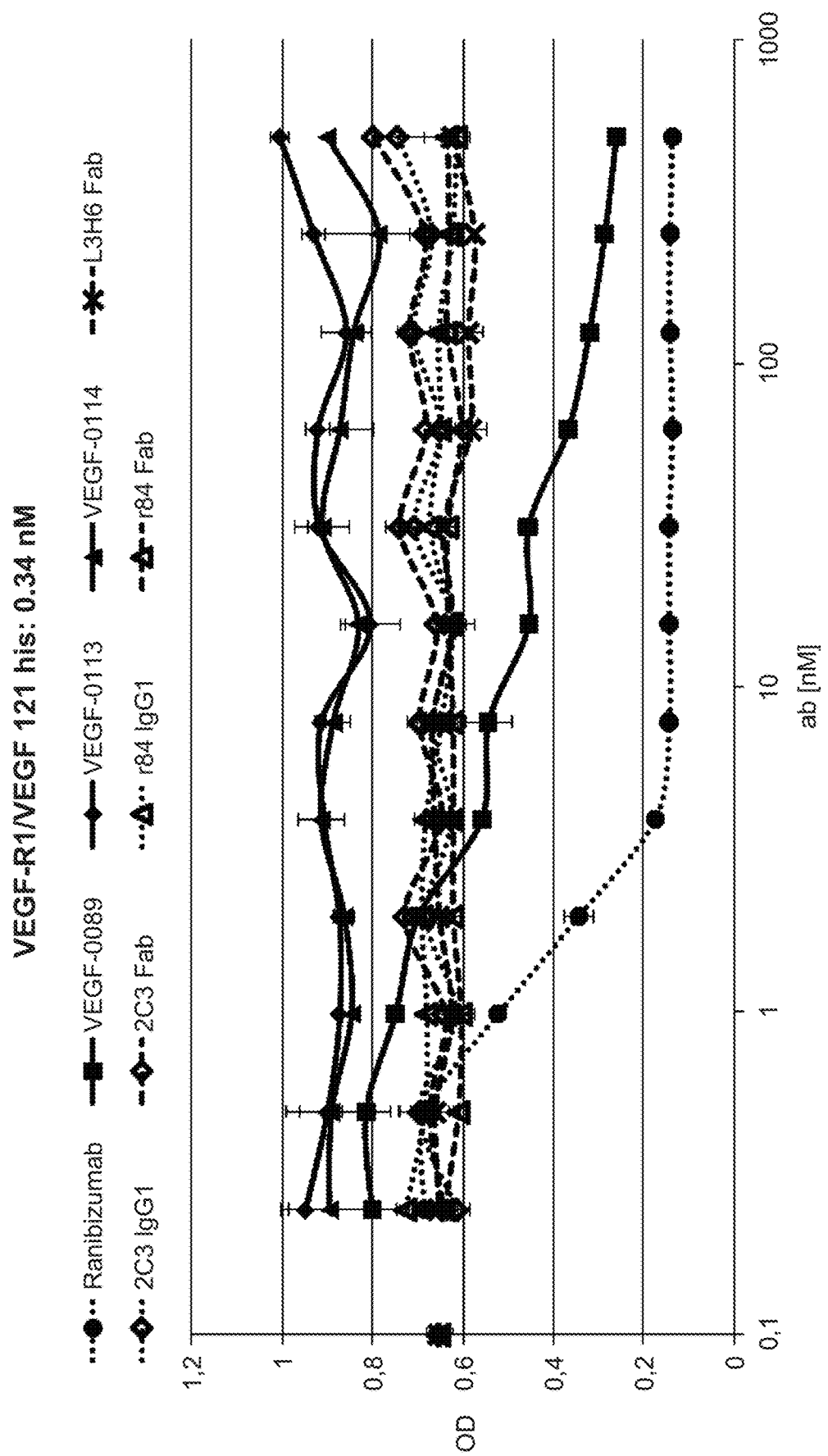
FIG. 6: Inhibition of VEGF binding to VEGF-R1 in presence of anti-VEGF antibodies as described in Example 6 (0.34 nM VEGF).

Binding of VEGF to VEGF-R1 in presence of antibody Fab fragments of the invention was tested as described in Example 6. All antibodies as listed in table 1 and table 2 were tested. Results are shown in FIG. 5.

No inhibition of VEGF-binding to VEGF-R1 was assessed in the experimental setup used for the tested prior art antibodies 2C3, r84 and L3H6.

The experiment was repeated under the same conditions as described above, however using 0.34 nM VEGF-121-His instead of 0.7 nM. Results are shown in FIG. 5.

Example 8

Assessment of IC50 of Anti-VEGF Antibodies Via Reporter Gene Assay (RGA)

The anti-VEGF antibodies of the invention (see table 1) were tested in nine concentrations ranging from 20 nM to 0.02 nM. Prior art antibody Ranibizumab (see table 2) was tested as a control.

Briefly, per well of a white 96 well multititerplate 37.5 µl of antibody solution/well were mixed with 37.5 µl VEGF- A121: 25 ng/ml/well and incubated for 30 min at room temperature. Subsequently, 75 µl/well HEK293-NFAT-RE-Luc2P/KDR_Suspension per 40000 cells/well was added and incubated for 5 hours at 37° C., 5% $CO_2$. Finally, 100 µl/well Bio-Glo™ reagent was added and Luminescence was determined using a Tecan infinite Reader. Results are shown in table 4:

TABLE 4

IC50 of anti-VEGF antibodies

|  | IC50 [nM] |
| --- | --- |
| VEGF-0089 | 0.59 |
| VEGF-0113 | 0.63 |
| VEGF-0114 | 1.34 |
| Ranibizumab | 0.81 |

The data confirm antagonistic binding to VEGF by all tested antibodies.

Example 9

Provision of Improved Variants of Human Anti-VEGF Antibody VEGF-0089

Additional improved antibody variants of antibody VEGF-0089 were generated, particularly to improve the preference to inhibit VEGF-binding to VEGF-R2 rather than VEGF-binding to VEGF-R1. From various antibody candidates, the three candidates listed in table 5 were selected. Antibody Fab fragments listed in table 5 were generated using the same methods as described in Example 1 (transient transformation of HEK-293 cells).

TABLE 5

Amino acid sequences of antibodies of the invention

|  | heavy chain | light chain |
| --- | --- | --- |
| VEGF-P1AD8675 | SEQ ID NO: 32 | SEQ ID NO: 14 |
| VEGF-P1AE3520 | SEQ ID NO: 41 | SEQ ID NO: 14 |
| VEGF-P1AE3521 | SEQ ID NO: 43 | SEQ ID NO: 14 |

Example 10

Binding Affinity of Antibodies of the Invention

The affinity of the antibodies was determined by SPR using the same methods as described in Example 2. All Fab fragments of antibodies of the invention as listed in table 1 and table 5 were tested. In addition, additional prior art antibodies HF2-1, HF2-5, HF2-9, and HF2-11 (disclosed in EP3006465), were assessed as described above. Amino acid sequences of those additional prior art antibodies are shown in table 6.

TABLE 6

Amino acid sequences of prior art antibodies disclosed in EP3006465

|  | heavy chain | light chain |
| --- | --- | --- |
| HF2-1 Fab | SEQ ID NO: 34 | SEQ ID NO: 35 |
| HF2-5 Fab | SEQ ID NO: 36 | SEQ ID NO: 35 |
| HF2-9 Fab | SEQ ID NO: 37 | SEQ ID NO: 38 |
| HF2-11 Fab | SEQ ID NO: 39 | SEQ ID NO: 40 |

Results are shown in table 7.

TABLE 7

Affinities of anti-VEGF antibodies

|  | KD [pM] at 25° C. | KD [pM] at 37° C. |
| --- | --- | --- |
| VEGF-0089 Fab | 143 | 110 |
| VEGF-0113 Fab | 22 | 29 |
| VEGF-0114 Fab | 50 | 54 |
| VEGF-P1AD8675 | 88 | 65 |
| VEGF-P1AE3520 | 31 | 39 |
| VEGF-P1AE3521 | 32 | 61 |
| HF2-1 Fab | 279 | 574 |
| HF2-5 Fab | 52 | 109 |
| HF2-9 Fab | 24 | 51 |
| HF2-11 Fab | 32 | 62 |

Example 11

Inhibition of VEGF-Binding to VEGF-R2 or VEGF-R1 in Presence of Anti-VEGF Antibodies Binding of VEGF to VEGF-R2 and VEGF-R2 in presence of antibody Fab fragments of the invention was tested as described in Example 2.

Figure 8:
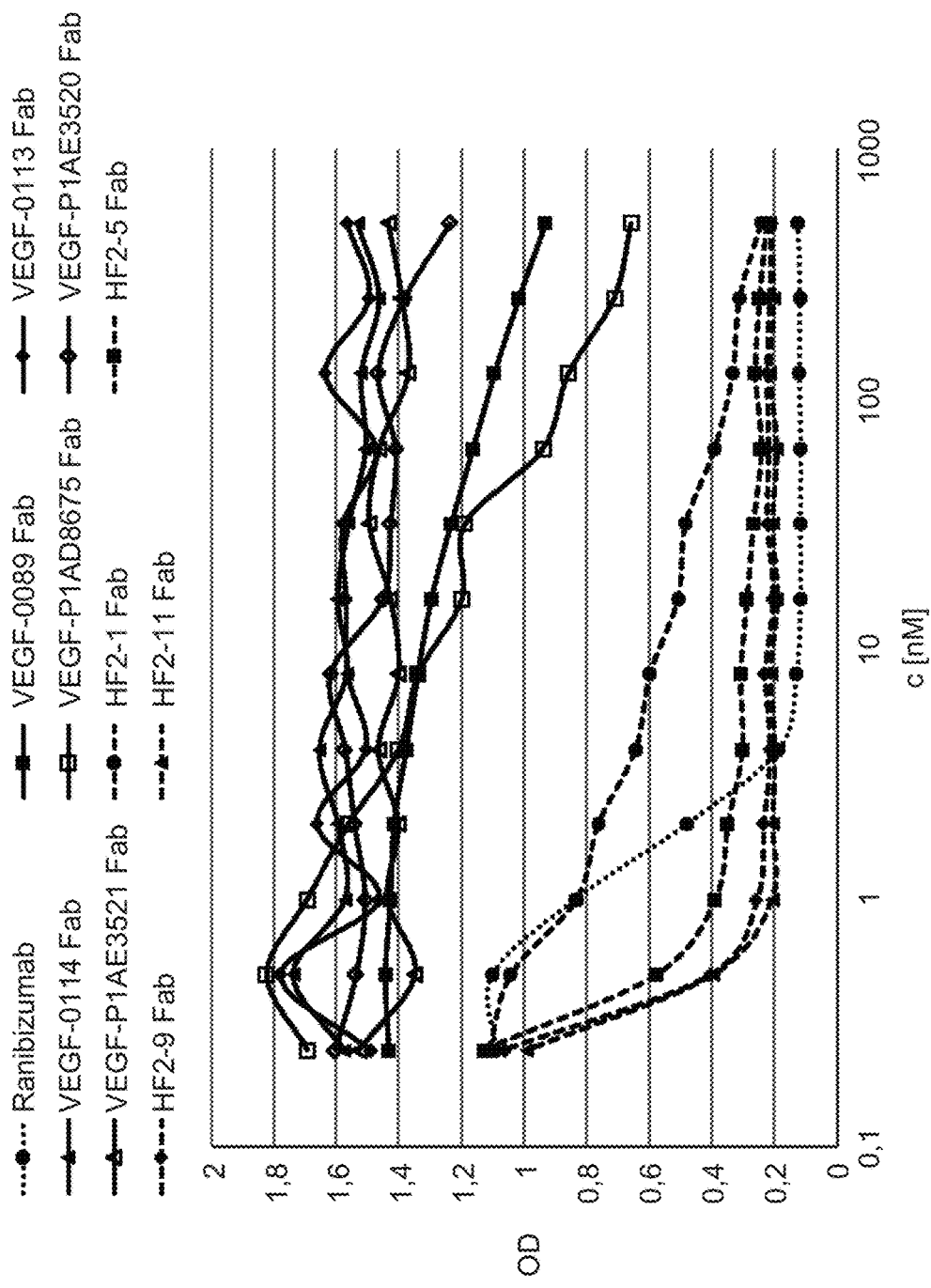
FIG. 8: Inhibition of VEGF binding to VEGF-R1 in presence of anti-VEGF antibodies as described in Example 11 (0.34 nM VEGF).
Figure 9:
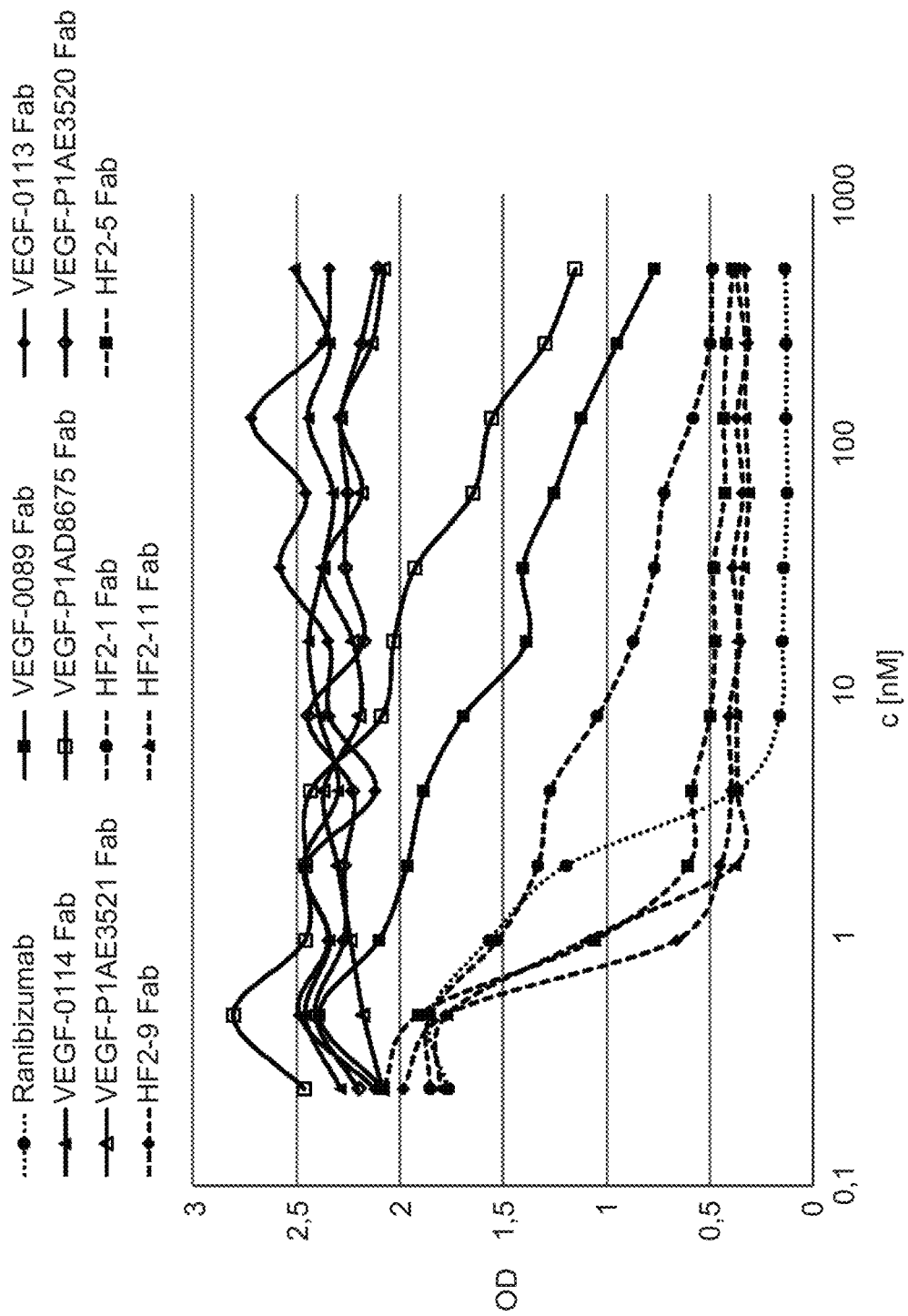
FIG. 9: Inhibition of VEGF binding to VEGF-R1 in presence of anti-VEGF antibodies as described in Example 11 (0.7 nM VEGF).
Figure 10:
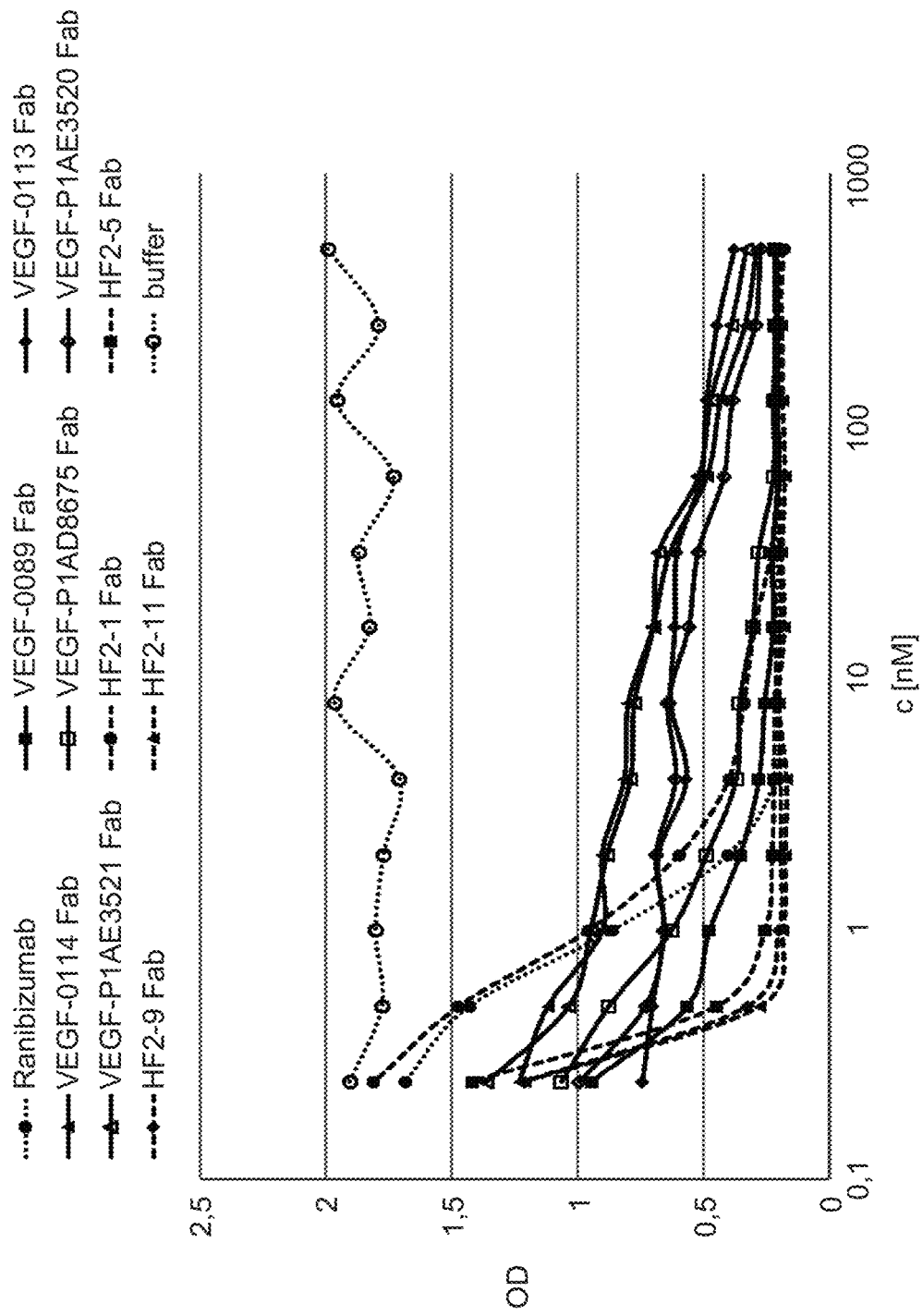
FIG. 10: Inhibition of VEGF binding to VEGF-R2 in presence of anti-VEGF antibodies as described in Example 11 (0.34 nM VEGF).
Figure 11:
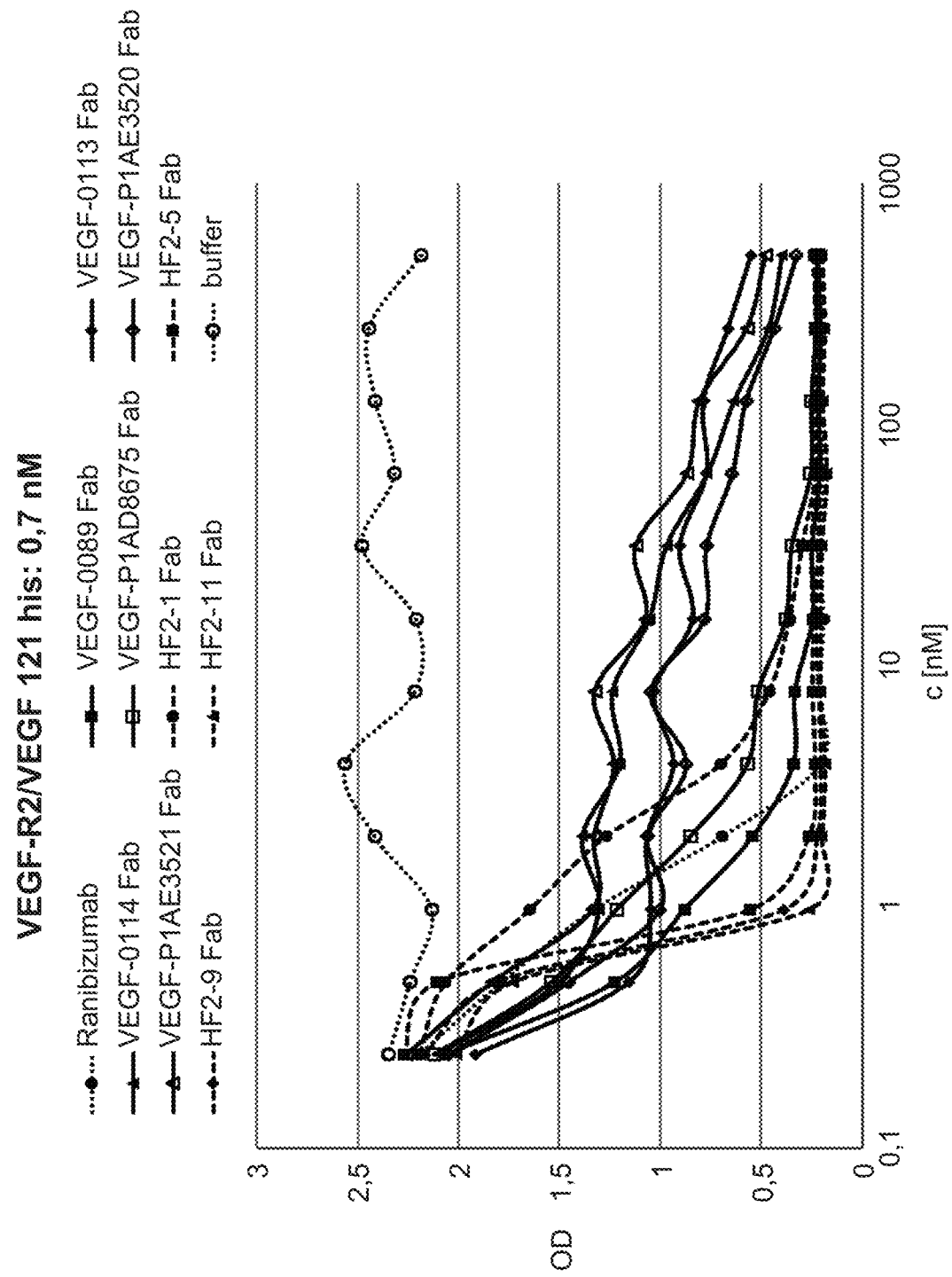
FIG. 11: Inhibition of VEGF binding to VEGF-R2 in presence of anti-VEGF antibodies as described in Example 11 (0.7 nM VEGF).

In these experiments, antibodies VEGF-0089, VEGF-0113, VEGF-0114, VEGF-P1AD8675, VEGF-P1AE3520 and VEGF-P1AE3521 of the invention were tested (see table 1 and table 5) and prior art antibodies 1-112-1, 1-112-5, 1-112-9, and 1-112-11 (see table 6) as well as Ranibizumab (see table 2) were analyzed in presence of VEGF. Results are shown in FIG. 8 and FIG. 10 (presence of 0.34 nM VEGF) and FIG. 9 and FIG. 11 (presence of 0.7 nm VEGF).

The tested prior art antibodies did not significantly inhibit VEGF-binding to VEGF receptor VEGF-R1. All tested antibodies of the invention preferentially inhibited VEGF-binding to VEGF-R2 rather than VEGF-binding to VEGF-R1.

Example 12

Chemical Stability of Exemplary Antibodies of the Invention

Chemical stability of exemplary antibody Fab fragments of the invention was tested as follows:
Chemical Degradation Test:
Antibody samples were formulated in 20 mM His/HisCl, 140 mM NaCl, pH 6.0, and were split into three aliquots: one aliquot was re-buffered into PBS, respectively, and two aliquots were kept in the original formulation. The PBS aliquot and one His/HisCl aliquot were incubated for 2 weeks (2 w) at 40° C. (His/NaCl) or 37° C. (PBS) in 1 mg/ml, the PBS sample was incubated further for total 4 weeks (4 w). The third control aliquot sample was stored at −80° C. After incubation ended, samples were analyzed for relative active concentration (Biacore; active concentration of both stressed aliquots of each binder is normalized to unstressed 4° C. aliquot), aggregation (SEC) and fragmentation (capillary electrophoresis or SDS-PAGE) and compared with the untreated control.

For Size Exclusion UHPLC (=SEC), proteins were separated depending on their molecular size in solution using a chromatographic gel like TSKgel UP-SW3000. With this method, protein solution was analyzed regarding their relative content of monomer, high molecular species (e.g. aggregates, dimers, impurities) and low molecular species (e.g. degradation products, impurities). 0.2 M Potassium phosphate, 0.25 M KCl, pH 6.2 was used as mobile phase. Protein solutions were diluted such as ~50μ of protein was injected in a volume of 5 μl, and analyzed with a flow rate of 0.3 ml/min at 25° C. Protein detection was done at 280 nm. Peak definition and peak integration were performed as demonstrated in the typical chromatograms in the product specific information document.

Fab fragments of antibodies VEGF-0089, VEGF-0113, VEGF-0114, VEGF-P1AD8675, VEGF-P1AE3520 and VEGF-P1AE3521 (see table 1 and table 5) were analysed. Results are shown in table 8 and table 9.

TABLE 8

VEGF-binding activity after stress of improved antibody Fab fragments

| | 2 w/40° C./ pH 6.0 | 2 w/37° C./ pH 7.4 | 4 w/37° C./ pH 7.4 |
|---|---|---|---|
| VEGF-0089 Fab | 101 | 102 | 101 |
| VEGF-0113 Fab | 103 | 103 | 101 |
| VEGF-0114 Fab | 99 | 102 | 99 |
| VEGF-P1AD8675 Fab | 101 | 102 | 109 |
| VEGF-P1AE3520 Fab | 100 | 102 | 101 |
| VEGF-P1AE3521 Fab | 101 | 103 | 99 |

TABLE 9

Molecular integrity after stress (4 weeks, pH 7.4, 37° C.) of improved antibody Fab fragments

| | Aggregation [% aggregates] | Main fraction [%] |
|---|---|---|
| VEGF-0089 Fab | 0.6 | 99.4 |
| VEGF-0113 Fab | 0.6 | 99.4 |
| VEGF-0114 Fab | 2 | 97.1 |
| VEGF-P1AD8675 Fab | 65.3 | 34.7 |
| VEGF-P1AE3520 Fab | 11.9 | 87.2 |
| VEGF-P1AE3521 Fab | 4.8 | 94.2 |

Example 13

X-Ray Crystallography of Generated Antibody VEGF-0089 in Complex with VEGF-Dimer and Epitope Determination The crystal structure of VEGF-0089 Fab fragment as described above was analyzed according to standard methods known in the art.

X-ray crystallography of VEGF-0089 Fab fragment in complex with VEGF-A121 was performed as follows:

Complex formation and purification of the dimeric complex VEGF-A121-VEGF-0089 Fab. For complex formation the VEGF-0089 Fab fragment and human VEGF-A121 (Peprotech) were mixed in a 1.1:1 molar ratio. After incubation for 16 hours overnight at 4° C. the complex was purified via gelfiltration chromatography on a Superdex200 (16/600) column in 20 mM MES, 150 mM NaCl, pH6.5. Fractions containing the dimeric complex were pooled and concentrated to 1.44 mg/ml.

Crystallization of dimeric VEGF-A121-VEGF-0089 Fab complex. Initial crystallization trials were performed in sitting drop vapor diffusion setups at 21° C. at a protein concentration of 11.5 mg/ml. Crystals appeared within 1 day out of 0.1 M Tris pH 8.5, 0.2 M LiSO4, 1.26 M $(NH_4)_2SO_4$. Plate shaped crystals grew in a week to a final size of 150×100×30 μm. The crystals were directly harvested from the screening plate without any further optimization steps.

Data collection and structure determination. For data collection crystals were flash cooled at 100K in precipitant solution with addition of 15% ethylene glycol as cryoprotectant. Diffraction data were collected at a wavelength of 1.0000 Å using a PILATUS 6M detector at the beamline X10SA of the Swiss Light Source (Villigen, Switzerland). Data have been processed with XDS (Kabsch, W. Acta Cryst. D66, 133-144 (2010)) and scaled with SADABS (BRUKER). The crystals belong to the space group C2 with cell axes of a=227.61 Å, b=66.97 Å, c=218.31 Å, β=104.54° and diffract to a resolution of 2.17 Å. The structure was determined by molecular replacement with PHASER (McCoy, A. J, Grosse-Kunstleve, R. W., Adams, P. D., Storoni, L. C., and Read, R. J. J. Appl. Cryst. 40, 658-674 (2007)) using the coordinates of a related in house structure of a Fab fragment and VEGF as search models. Programs from the CCP4 suite (Collaborative Computational Project, Number 4 Acta Cryst. D50, 760-763 (1994)) and Buster (Bricogne, G., Blanc, E., Brandl, M., Flensburg, C., Keller, P., Paciorek, W., Roversi, P., Sharff, A., Smart, O. S., Vonrhein, C., Womack, T. O. (2011). Buster version 2.9.5 Cambridge, United Kingdom: Global Phasing Ltd) have been used to subsequently refine the data. Manual rebuilding of protein using difference electron density was done with COOT (Emsley, P., Lohkamp, B., Scott, W. G. and Cowtan, K. Acta Cryst D66, 486-501 (2010)). Data collection and refinement statistics for both structures are summarized in table 10. All graphical presentations were prepared with PYMOL (DeLano Scientific, Palo Alto, C A, 2002).

TABLE 10

Data collection and structure refinement statistics

| Data Collection | |
|---|---|
| Wavelength (Å) | 1.0 |
| Resolution[1] (Å) | 49.49-2.17 (2.27-2.17) |
| Space group | C2 |
| Unit cell (Å, °) | 227.61 66.97 218.31, 90.00 104.54 90.00 |
| Unique reflections | 168745 (21164) |
| Multiplicity | 3.45 (3.43) |
| Completeness (%) | 99.8 (99.6) |
| Mean I/σ(I) | 8.36 (0.71) |
| R-meas | 0.073 (0.86) |
| CCI/2 | 0.999 (0.364) |
| Refinement | |
| Resolution[1] (Å) | 49.49-2.17 (2.23-2.17) |
| Reflections used in refinement | 168674 (12361) |
| Reflections used for R-free | 8487 (617) |
| R-work[3] | 0.185 (0.262) |
| R-free[4] | 0.227 (0.287) |
| Number of atoms | 16966 |
| Protein residues | 1466 |
| RMS bonds (Å) | 0.010 |

TABLE 10-continued

Data collection and structure refinement statistics

| | |
|---|---|
| RMS angles (°) | 1.20 |
| Ramachandran favored (%) | 97.85 |
| Ramachandran outliers (%) | 0.15 |
| Rotamer outliers (%) | 3.47 |
| Clashscore | 2.39 |
| Average B-factor (Å$^2$) | 65.89 |
| protein | 66.85 |
| solvent | 64.05 |

[1]Values in parentheses refer to the highest resolution bins.
[2]$R_{merge} = \Sigma |I - <I>|/\Sigma I$ where I is intensity.
[3]$R_{work} = \Sigma |F_o - <F_c>|/\Sigma P_o$ where $F_o$ is the observed and $F_c$ is the calculated structure factor amplitude.
[4]$R_{free}$ was calculated based on 5% of the total data omitted during refinement.

Figure 12:
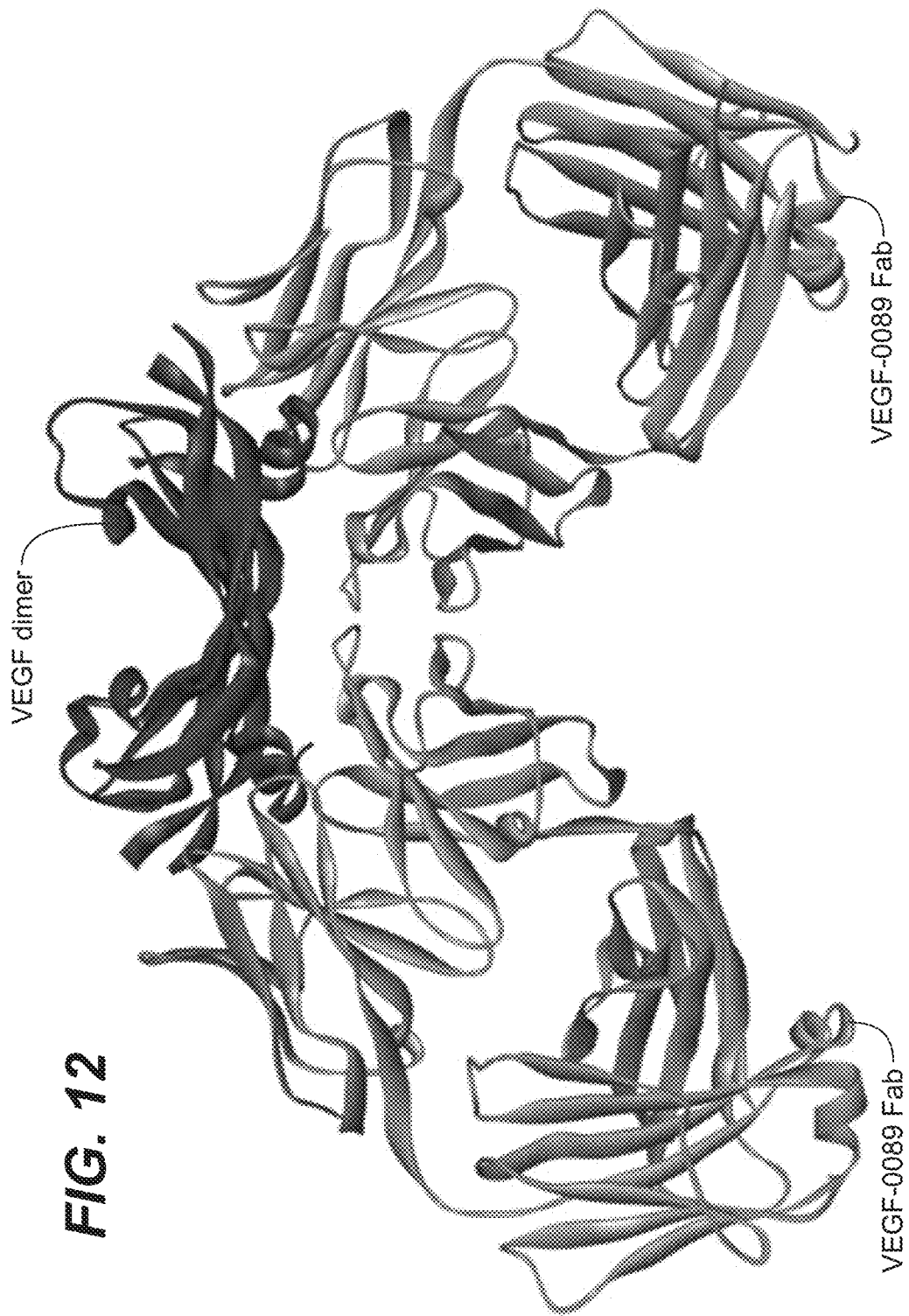
FIG. 12: Crystal structure of VEGF dimer in complex with anti-VEGF antibody VEGF-0089 as determined by X ray crystallography according to Example 13.

A schematic illustration of the crystal structure of two VEGF-0089 Fab fragments in complex with a human VEGF-A121 dimer is shown in FIG. 12. Amino acid residues in the VEGF-A121 dimer in contact within a distance of 5 Å with antibody VEGF-0089 Fab fragment form the conformational epitope bound by VEGF-0089 Fab on the VEGF-A121 dimer. The amino acid sequence of VEGF-A121 is SEQ ID NO: 45. An illustration of the amino acids comprised in the epitope on both VEGF-A121 molecules in the VEGF dimer is highlighted in FIG. 13.

Antibody VEGF-0089 Fab binds to the following epitope on the VEGF-A121 dimer:

in one of the individual VEGF-A121 molecules within the VEGF dimer amino acids F17, M18, D19, Y21, Q22, R23, Y25, H27, P28, I29, E30, M55, N62, L66, N100, K101, C102, E103, C104, R105 and P106; and in the other one of the individual VEGF-A121 molecules within the VEGF dimer amino acids E30, K48, M81 and Q87.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An antibody that binds to vascular endothelial growth factor (VEGF), the antibody comprising a pair of heavy chain variable domain (VH) and light chain variable domain (VL) amino acid sequences selected from the group consisting of:
   (a) a VH amino acid sequence of SEQ ID NO: 01 and a VL amino acid sequence of SEQ ID NO: 02,
   (b) a VH amino acid sequence of SEQ ID NO: 09 and a VL amino acid sequence of SEQ ID NO: 02,
   (c) a VH amino acid sequence of SEQ ID NO: 11 and a VL amino acid sequence of SEQ ID NO: 02,
   (d) a VH amino acid sequence of SEQ ID NO: 33 and a VL amino acid sequence of SEQ ID NO: 02,
   (e) a VH amino acid sequence of SEQ ID NO: 42 and a VL amino acid sequence of SEQ ID NO: 02, and
   (f) a VH amino acid sequence of SEQ ID NO: 44 and a VL amino acid sequence of SEQ ID NO: 02.

2. The antibody of claim 1, which is a Fab fragment.

3. An isolated nucleic acid encoding an antibody selected according to claim 1.

4. A host cell comprising the nucleic acid of claim 3.

5. A method of producing an antibody that binds to VEGF comprising culturing the host cell of claim 4 under conditions suitable for the expression of the antibody.

6. A pharmaceutical composition comprising the antibody of claim 1, and a pharmaceutically acceptable carrier.

7. The pharmaceutical composition of claim 6, further comprising an additional therapeutic agent.

8. An antibody of claim 1, wherein the antibody comprises the pair of VH and VL amino acid sequences set forth in (a).

9. An isolated nucleic acid encoding the antibody of claim 8.

\* \* \* \* \*